(12) United States Patent
Kwiatkowski

(10) Patent No.: US 10,806,796 B2
(45) Date of Patent: Oct. 20, 2020

(54) CONJUGATES OF BIOLOGICALLY ACTIVE MOLECULES TO FUNCTIONALIZED POLYMERS

(71) Applicant: QuiaPEG Pharmaceuticals AB, Uppsala (SE)

(72) Inventor: Marek Kwiatkowski, Uppsala (SE)

(73) Assignee: QuiaPEG Pharmaceuticals AB, Uppsala (SE)

( * ) Notice: Subject to any disclaimer, the term of this patent is extended or adjusted under 35 U.S.C. 154(b) by 0 days.

(21) Appl. No.: 16/544,823

(22) Filed: Aug. 19, 2019

(65) Prior Publication Data

US 2020/0222546 A1 Jul. 16, 2020

Related U.S. Application Data

(63) Continuation of application No. 16/024,993, filed on Jul. 2, 2018, now Pat. No. 10,383,946, which is a continuation of application No. 14/407,580, filed as application No. PCT/IB2013/001885 on Jun. 12, 2013, now Pat. No. 10,010,621.

(60) Provisional application No. 61/786,121, filed on Mar. 14, 2013, provisional application No. 61/786,265, filed on Mar. 14, 2013, provisional application No. 61/786,287, filed on Mar. 14, 2013, provisional application No. 61/786,221, filed on Mar. 14, 2013, provisional application No. 61/786,162, filed on Mar. 14, 2013, provisional application No. 61/786,237, filed on Mar. 14, 2013, provisional application No. 61/785,996, filed on Mar. 14, 2013, provisional application No. 61/658,853, filed on Jun. 12, 2012, provisional application No. 61/658,839, filed on Jun. 12, 2012, provisional application No. 61/658,835, filed on Jun. 12, 2012, provisional application No. 61/658,850, filed on Jun. 12, 2012, provisional application No. 61/658,856, filed on Jun. 12, 2012, provisional application No. 61/658,836, filed on Jun. 12, 2012, provisional application No. 61/658,827, filed on Jun. 12, 2012.

(51) Int. Cl.

| | |
|---|---|
| A61K 47/60 | (2017.01) |
| C07K 1/107 | (2006.01) |
| A61K 38/17 | (2006.01) |
| A61K 38/18 | (2006.01) |
| A61K 38/28 | (2006.01) |
| A61K 38/36 | (2006.01) |
| A61K 38/37 | (2006.01) |
| A61K 38/48 | (2006.01) |
| A61K 39/395 | (2006.01) |
| C12N 9/96 | (2006.01) |
| A61K 38/47 | (2006.01) |
| C07K 14/705 | (2006.01) |
| C07K 16/00 | (2006.01) |
| C07K 16/42 | (2006.01) |
| C07K 19/00 | (2006.01) |
| C12N 9/36 | (2006.01) |
| A61K 47/68 | (2017.01) |
| C07K 14/62 | (2006.01) |
| A61K 39/00 | (2006.01) |

(52) U.S. Cl.
CPC .......... *A61K 47/60* (2017.08); *A61K 38/1793* (2013.01); *A61K 38/1816* (2013.01); *A61K 38/28* (2013.01); *A61K 38/36* (2013.01); *A61K 38/37* (2013.01); *A61K 38/47* (2013.01); *A61K 38/4846* (2013.01); *A61K 38/4866* (2013.01); *A61K 39/395* (2013.01); *A61K 39/39566* (2013.01); *A61K 47/68* (2017.08); *C07K 1/1077* (2013.01); *C07K 14/62* (2013.01); *C07K 14/70578* (2013.01); *C07K 16/00* (2013.01); *C07K 16/4291* (2013.01); *C07K 19/00* (2013.01); *C12N 9/2462* (2013.01); *C12N 9/96* (2013.01); *C12Y 302/01017* (2013.01); *A61K 2039/505* (2013.01); *C07K 2319/30* (2013.01)

(58) Field of Classification Search
CPC .......................... A61K 47/60; A61K 39/39566
See application file for complete search history.

(56) References Cited

U.S. PATENT DOCUMENTS

| | | | |
|---|---|---|---|
| 4,647,447 | A | 3/1987 | Gries et al. |
| 5,922,897 | A | 7/1999 | Hu et al. |
| 6,165,501 | A | 12/2000 | Tirosh et al. |
| 6,180,095 | B1 | 1/2001 | Greenwald et al. |
| 6,211,244 | B1 | 4/2001 | Van Wagenen et al. |
| 6,267,958 | B1 | 7/2001 | Andya et al. |
| 6,320,041 | B1 | 11/2001 | Hogrefe et al. |

(Continued)

FOREIGN PATENT DOCUMENTS

| | | |
|---|---|---|
| JP | 10175987 | 6/1998 |
| WO | WO 1995/23160 | 8/1995 |

(Continued)

OTHER PUBLICATIONS

Collins et al. "Implications of coagulation factor VIII and IX pharmaco-kinetics in the prophylactic treatment of haemophilia" Haemophilia, 2011, vol. 17, pp. 2-10.*

(Continued)

*Primary Examiner* — Joseph R Kosack
(74) *Attorney, Agent, or Firm* — Fish & Richardson P.C.

(57) ABSTRACT

This document relates to conjugates of a biologically active molecule or a derivative thereof and functionalized (e.g., mono- or bi-functional) polymers (e.g., polyethylene glycol and related polymers) as well as methods and materials for making and using such conjugates.

23 Claims, 14 Drawing Sheets

Specification includes a Sequence Listing.

(56) References Cited

U.S. PATENT DOCUMENTS

| | | |
|---|---|---|
| 8,846,941 B2 | 9/2014 | Kwiatkowski |
| 9,220,789 B2 | 12/2015 | Kwiatkowski |
| 9,790,324 B2 | 10/2017 | Kwiatkowski |
| 9,849,187 B2 | 12/2017 | Kwiatkowski |
| 10,010,621 B2 | 7/2018 | Kwiatkowski |
| 2003/0165849 A1 | 9/2003 | Zhang et al. |
| 2006/0063147 A1 | 3/2006 | Chernov et al. |
| 2006/0079486 A1 | 4/2006 | Zalipsky |
| 2006/0275252 A1 | 12/2006 | Harris et al. |
| 2007/0276139 A1 | 11/2007 | Song et al. |
| 2009/0312236 A1 | 12/2009 | Beals et al. |
| 2010/0240730 A1 | 9/2010 | Beigelman et al. |
| 2012/0178940 A1 | 7/2012 | Kwiatkowski |
| 2014/0030278 A1 | 1/2014 | Kwiatkowski |
| 2015/0232615 A1 | 8/2015 | Kwiatkowski |
| 2016/0354477 A1 | 12/2016 | Kwiatkowski |
| 2018/0251598 A1 | 9/2018 | Kwiatkowski |
| 2019/0125887 A1 | 5/2019 | Kwiatkowski |

FOREIGN PATENT DOCUMENTS

| | | |
|---|---|---|
| WO | WO 02/083954 | 10/2002 |
| WO | WO 2002/083954 | 10/2002 |
| WO | WO 2004/030617 | 4/2004 |
| WO | WO 2004/073620 | 9/2004 |
| WO | WO 2007/059912 | 5/2007 |
| WO | WO 2010/014258 | 2/2010 |

OTHER PUBLICATIONS

Extended European Search Report in European Application No. 19189994.7 dated Feb. 28, 2020, 6 pages.

Ananda et al., "Analysis of functionalization of methoxy-PEG as maleimide-PEG," Anal. Biochem., 2008, 374:231-242.

Ansel Introduction to Pharmaceutical Dosage Forms, Fourth Edition 1985, 126.

Atherton et al., "The Fluorenylmethoxycarbonyl Amino Protecting Group," in The Peptides, S. Udenfriend and J. Meienhofer, Academic Press, New York, 1987, 40 pages.

Authorized Officer A. Van Der Heijden. International Search Report and Written Opinion in International Application No. PCT/IB2011/003206, dated Jun. 19, 2012, 18 pages.

Blom et al., "Preparative LC-MS Purification: Improved Compound Specific Method Optimization," J. Combi. Chem., 2004, 6:874-883.

Choi et al., "PEGylation of G-CSF using cleavable olgi-lactic acid linkage," Journal of Controlled Release, 2003, 271-284.

Conolly et al., "Chemical synthesis of oligonucleotides containing a free sulphydryl group and subsequent attachment of thiol specific probes," Nucleic Acids Res., 1985, 13(12):4485-4502.

Conrad et al., "Studies on the stability of trialkyl phosphates and di-(2' deoxythymidine) phosphotriesters in alkaline and neutral solution. A model study for hydrolysis of phosphotriesters in DNA and on the influence of a β hydroxyethyl ester group," Chem. Bio. Interactions, 1986, 60:57-65.

Dahlback, "Inherited thrombophilia: resistance to activated protein C as a pathogenic factor of venous thromboembolism," Blood, 1995, 85:607-614.

Drioli et al., "Pure, homo-bifunctional poly(ethylene glycol) orthogonally protected: synthesis and characterisation," Reactive & Functional Polymers, 2001, 48:119-128.

Ducreux et al., "The Inhibitory Potencies of Monoclonal Antibodies to the Macrophage Adhesion Molecule Sialoadhesin Are Greatly Increased Following PEGylation," Bioconjugate Chem., 2008, 19:2088-2094.

Esmon et al., "Isolation of a membrane-bound cofactor for thrombin-catalyzed activation of protein C," J Biol Chem., 1982, 257:859-864.

Fee et al., "PEG-proteins: Reaction engineering and separation issues," Chemical Engineering Science, 2006, 61:924-934.

Fidanza et al., "Functionalization of Oligonucleotides by the Incorporation of Thio-Specific Report Groups," Methods in Molecular Biology, 1994, 26, 121-143.

Fiore et al., "The biochemical basis for the apparent defect of soluble mutant tissue factor in enhancing the proteolytic activities of factor VIIa," J Biol Chem., 1994, 269:143-149.

Garegg et al., "Nucleoside hydrogenphosphonates in Oligonucleotide Synthesis," Chem. Scr., 1986, 26:59-62.

Gaur, "Introduction of 5'-Terminal Amino and Thiol Groups into Synthetic Oligonucleotides," Nucleosides, Nucleotides & Nucleic Acids, 1991, 10(4):895-909.

Gouy et al., "Special feature of mixed phosphotriester derivatives of cytarabine," Bioorganic & Medicinal Chemistry, 2009, 6340-6347.

Greenwald et al., "A New Aliphatic Amino Prodrug System for the Delivery of Small Molecules and Proteins Utilizing Novel PEG Derivatives," J. Med. Chem., 2004, 47:726-734.

Hann et al., "1,3-Anhydro-2,4-methylene-D,L-xylitol and Related Compounds," J. Am. Chem. Soc., 1950, 72:561-566.

Hatakeyama et al., "Development of a novel systemic gene delivery system for cancer therapy with a tumor-specific cleavable PEG-lipid," Gene Therapy, 2007, 14:68-77.

Hecker et al., "Prodrugs of Phosphates and Phosphonates," J. Med. Chem., 2008, 51:2328-2345.

Hoey et al., "Chemistry of X-Ray Contrast Media," Handbook of Experimental Pharmacology, 1984, 73:23-125.

Hovinen et al., "Versatile Strategy for Oligonucleotide Derivatization. Introduction of Lanthanide(III) Chelates to Oligonucleotides," Organic Lett., 2001, 3(16):2473-2476.

International Preliminary Report on Patentability in International Application No. PCT/IB2011/003206, dated Jun. 27, 2013, 12 pages.

International Preliminary Report on Patentability in International Application No. PCT/IB2013/001885, dated Dec. 16, 2014, 11 pages.

International Search Report and Written Opinion in International Application No. PCT/IB013/001885, dated Jun. 6, 2014, 17 pages.

Invitation to Pay Addition Fees and, Where Applicable, Protest Fee in International Application No. PCT/IB2013/001885, mailed Mar. 3, 2014, 7 pages.

Jagur-Grudzinski, "Biomedical application of functional polymers," Reactive & Functional Polymers, 1999, 39:99-138.

Kachalova et al., "A New and Efficient Method for Synthesis of 5'Conjugates of Oligonucleotides through Amide-Bond Formation on Solid Phase," Helv. Chim. Acta, 2002, 85:2409-2416.

Khomutov, "Derivatives of Hydroxylamine, Synthesis of o-substituted hydroxylamines," Journal of General Chemistry 1961, 31:1992-1995.

Koo et al., "Disulfide-cross-linked PEG-poly(amino acid)s copolymer micelles for glutathione-mediated intracellular drug delivery," Chem. Commun., 2008, 6570-6572.

Krempsky et al., "Biotin and fluorescein labeling of biomolecules by active esters of 1-phenypyrazolin-5-ones," Tet. Lett., 1996, 37(12):4313-4316.

Leisvuori et al., "Chemical and enzymatic stability of amino acid derived phosphoramidates of antiviral nucleoside 5'-monophosphates bearing a biodegradable protecting group," Organic & Biomolecular Chemistry, 2010, 8:2131-2141.

Liang et al. "PAMAM Dendrimers and Branched Polyethyleneglycol (Nanoparticles) Prodrugs of (+13-D-(2R, 4R)-dioxolanethymine (DOT) and Their Anti-HIV Activity", Antiviral Chemistry and Chemotherapy.,17:321-329, 2006.

Mackman and Cihlar, "Prodrug Strategies in the Design of Nucleoside and Nucleotide Antiviral Therapeutics," Annual Reports in Medicinal Chemistry, 2004, 39:306-321.

Marcus et al., "Turning Low-Molecular-Weight Drugs into Prolonged Acting Prodrugs by Reversible Pegylation: A Study with Gentamicin," J. Med. Chem, 2008, 51:4300-4305.

McGuigan et al., "Synthesis and biological evaluation of some phosphate triester derivatives of the anti-viral drug AraA," Nucl. Acids Res., 1989, 17(15):6065-6075.

Nesher et al., "Reversible Pegylation Prolongs the Hypotensive Effect of Atrial Natriuretic Peptide," Bioconjugate Chem, 2008, 19:342-348.

(56) References Cited

OTHER PUBLICATIONS

Oumzil et al., "Reduction-triggered delivery using nucleoside-lipid based carriers possessing a cleavable PEG coating," Journal of Controlled Release, 2011, 123-130.
Peng "Vaccines targeting IgE in the treatment of asthma and allergy" Human Vaccines, 2009, vol. 5, pp. 302-309.
Petursson et al., "Protecting Groups in Carbohydrate Chemistry," J. Chem. Educ., 1997, 74(11):1297.
Podyminogin et al., "Attachment of benzaldehyde-modified oligodeoxynucleotide probes to semicarbazide-coated glass,"Nucl. Acids Res., 2001, 29(24):5090-5098.
Raddetz et al., "Hydrazide oligonucleotides: new chemical modification for chip array attachment and conjugation," Nucleic Acids Res., 2002, 30(21):4793-4802.
Rayudu, Radiotracers for Medical Applications, vol. I, pp. 201.
Remington's Pharmaceutical Sciences, 19th Edition (Mack Publishing Company, 1995 (Table of Contents only).
Roberts et al., "Chemistry for peptide and protein PEGylation," Advanced Drug Delivery Reviews, 2002, 54:459-476.
Sakaitani et al., "One-pot Conversion of N-Benzyloxycarbonyl Group into N-Tert-Butoxycarbonyl Group," Tetrahedron Lett., 1988, 29:2983.
Sandstrom, "Omalizumab in the management of patients with allergic (IgE-mediated) asthma," J Asthma Allergy, 2009, 2:49-62.
Sebastian et al., "Catumaxomab: a bispecific trifunctional antibody," Drugs Today (Barc), 2009, 45(8):589-97 (Abstract Only).
Shechter et al., "Reversible pegylation of insulin facilitates its prolonged action in vivo," European Journal of Pharmaceutics and Biopharmaceutics, 2008, 70:19-28.
Singh et al. "New Method to Prepare Peptide-Oligonucleotide Conjugates through Glyoxylic Oxime Formation," J. Org. Chem., 2004, 69:8544-8546.
Spinelli et al. "Aldehydic Oligonucleotide: A Key Intermediate for the Preparation of Oligonucleotide Conjugates Through Oxime Bond Formation," Nucleosides, Nucleotides and Nucleic Acids, 2007, 26:883-887.
Stahl et al., "General Procedure for the Synthesis of Mono-N-acylated 1,6- Diaminohexanes," J. Org. Chem., 1978, 43:2285.
Storring et al., "Epoetin alfa and beta differ in their erythropoietin isoform compositions and biological properties," Br J Haematol., 1998, 100(1):79-89.
Suzawa et al., "Enhanced tumor cell selectivity of Adriamycin-monoclonal antibody conjugate via a poly(ethylene glycol)-based cleavable linker," Journal of Controlled Release, 2002, 229-242.
Suzawa et al., "Synthesis and HPLC analysis of enzymatically cleavable linker consisting of poly(ethylene glycol) and dipeptide for the development of immunoconjugate," Journal of Controlled Release, 2000, 27-41.
Swanson, "Enhancement Agents for Ultrasound: Fundamentals," Pharmaceuticals in Medical Imaging, 1990, pp. 682-687.
Tao et al., "α-Aldehyde Terminally Functional Methacrylic Polymers from Living Radical Polymerization: Application in Protein Conjugation 'Pegylation'," J. Am. Chem. Soc., 2004, 126:13220-13221.
Tjulandin et al., "Epoetin Theta with a New Dosing Schedule in Anaemic Cancer Patients Receiving Nonplatinum-Based Chemotherapy: A Randomised Controlled Trial," Arch Drug Inf., 2011, 4(3):33-41.
Tyler et al., "In Vivo Enhancement of Ultrasonic Image Luminance by Aqueous Solutions with High Speed of Sound," Ultrasonic Imaging, 1981, 3:323-29.
Wagner et al., "Pronucleotides: Toward the in Vivo Delivery of Antiviral and Anticancer Nucleotides," Med Res Rev, 2000, 6:417-451.
Werner and Chantelau, "Differences in bioactivity between human insulin and insulin analogues approved for therapeutic use—compilation of reports from the past 20 years," Diabetol Metab Syndr, 2011, 3:13, 10 pages.
Wong et al., "Acid cleavable PEG-lipids for applications in a ternary gene delivery vector," Mol. BioSyst., 2008, 532-541.
Xu et al., "Esterase-catalyzed dePEGylation of pH-sensitive vesicles modified with cleavable PEG-lipid derivatives," Journal of Controlled Release, 2008, 238-245.
Zalipsky et al., "Thiolytically Cleavable Dithiobenzyl Urethane-Linked Polymer-Protein Conjugates as Macromolecular Prodrugs: Reversible PEGylation of Proteins," Bioconjugate Chem, 2007, 18:1869-1878.
Zwierzak et al., "Phosphorous acid amides-II: Synthesis of momoalkyl phosphoroamidites (RO)(R2'N)P(0)H," Tetrahedron, 1967, 23:2243-2252.

* cited by examiner

>Anti IgE antibody VH domain chain 1
EVQLVESGGGLVQPGGSLRLSCAVSGYSITSGYSWNWIRQAPGKGLEWVASITYDGSTNY
ADSVKGRFTISRDDSKNTFYLQMNSLRAEDTAVYYCARGSHYFGHWHFAVWGQGTLVTVS
SGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKAEPKSCDKTHTCPPCPAPELLGGPSV
FLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTK
NQVSLTCLVKGFYPSDIAVEWESNGQPENNYKTTPPVLDSDGSFFLYSKLTVDKSRWQQG
NVFSCSVMHEALHNHYTQKSLSLSPGK >Anti IgE antibody VL domain chain 1
DIQLTQSPSSLSASVGDRVTITCRASQSVDYDGDSYMNWYQQKPGKAPKLLIYAASYLES
GVPSRFSGSGSGTDFTLTISSLQPEDFATYYCQQSHEDPYTFGQGTKVEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNR >Anti IgE antibody VH domain chain 2
EVQLVESGGGLVQPGGSLRLSCAVSGYSITSGYSWNWIRQAPGKGLEWVASITYDGSTNY
ADSVKGRFTISRDDSKNTFYLQMNSLRAEDTAVYYCARGSHYFGHWHFAVWGQGTLVTVS
SGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKAEPKSCDKTHTCPPCPAPELLGGPSV
FLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTK
NQVSLTCLVKGFYPSDIAVEWESNGQPENNYKTTPPVLDSDGSFFLYSKLTVDKSRWQQG
NVFSCSVMHEALHNHYTQKSLSLSPGK >Anti IgE antibody VL domain chain 2
DIQLTQSPSSLSASVGDRVTITCRASQSVDYDGDSYMNWYQQKPGKAPKLLIYAASYLES
GVPSRFSGSGSGTDFTLTISSLQPEDFATYYCQQSHEDPYTFGQGTKVEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNR

FIG. 1

P01308[25-54], Insulin, Homo sapiens (highlighted)

```
         10         20         30         40         50         60
MALWMRLLPL LALLALWGPD PAAAFVNQHL CGSHLVEALY LVCGERGFFY TPKTRREAED 70         80         90        100        110
LQVGQVELGG GPGAGSLQPL ALEGSLQKRG IVEQCCTSIC SLYQLENYCN
```

P01308[90-110], Insulin, Homo sapiens (highlighted)

```
         10         20         30         40         50         60
MALWMRLLPL LALLALWGPD PAAAFVNQHL CGSHLVEALY LVCGERGFFY TPKTRREAED 70         80         90        100        110
LQVGQVELGG GPGAGSLQPL ALEGSLQKRG IVEQCCTSIC SLYQLENYCN
```

FIG. 7

```
>DB00005 sequence

LPAQVAFTPYAPEPGSTCRLREYYDQTAQMCCSKCSPGQHAKVFCTKTSDTVCDSCEDST
YTQLWNWVPECLSCGSRCSSDQVETQACTREQNRICTCRPGWYCALSKQEGCRLCAPLRK
CRPGFGVARPGTETSDVVCKPCAPGTFSNTTSSTDICRPHQICNVVAIPGNASMDAVCTS
TSPTRSMAPGAVHLPQPVSTRSQHTQPTPEPSTAPSTSFLLPMGPSPPAEGSTGDEPKSC
DKTHTCPPCPAPELLGGPSVFLFPPKPKDTLMISRTPEVTCVVVDVSHEDPQVKFNWYVD
GVQVHNAKTKPREQQYNSTYRVVSVLTVLHQNWLDGKEYKCKVSNKALPAPIEKTISKAK
GQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK
```

FIG. 10

SEQUENCE LISTING

```
<160> NUMBER OF SEQ ID NOS: 4

<210> SEQ ID NO 1
<211> LENGTH: 447
<212> TYPE: PRT
<213> ORGANISM: Artificial Sequence
<220> FEATURE:
<223> OTHER INFORMATION: humanized antibody sequences

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Ala Asp Ser Val
    50                  55                  60

Lys Gly Arg Phe Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
            85                  90                  95

Ala Arg Gly Ser His Tyr Phe Gly His Trp His Phe Ala Val Trp Gly
            100                 105                 110
```

```
Gln Gly Thr Leu Val Thr Val Ser Ser Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 2
<211> LENGTH: 110
<212> TYPE: PRT
<213> ORGANISM: Homo sapiens

<400> SEQUENCE: 2

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45
```

```
Phe Tyr Thr Pro Lys Thr Arg Arg Glu Ala Glu Asp Leu Gln Val Gly
 50                  55                  60

Gln Val Glu Leu Gly Gly Gly Pro Gly Ala Gly Ser Leu Gln Pro Leu
 65                  70                  75                  80

Ala Leu Glu Gly Ser Leu Gln Lys Arg Gly Ile Val Glu Gln Cys Cys
                 85                  90                  95

Thr Ser Ile Cys Ser Leu Tyr Gln Leu Glu Asn Tyr Cys Asn
            100                 105                 110

<210> SEQ ID NO 3
<211> LENGTH: 467
<212> TYPE: PRT
<213> ORGANISM: Artificial Sequence
<220> FEATURE:
<223> OTHER INFORMATION: fusion protein of human soluble TNF receptor 2
      to the Fc component of human IgG1

<400> SEQUENCE: 3

Leu Pro Ala Gln Val Ala Phe Thr Pro Tyr Ala Pro Glu Pro Gly Ser
 1                5                  10                  15

Thr Cys Arg Leu Arg Glu Tyr Tyr Asp Gln Thr Ala Gln Met Cys Cys
                 20                  25                  30

Ser Lys Cys Ser Pro Gly Gln His Ala Lys Val Phe Cys Thr Lys Thr
             35                  40                  45

Ser Asp Thr Val Cys Asp Ser Cys Glu Asp Ser Thr Tyr Thr Gln Leu
 50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                 85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
            115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
            195                 200                 205

Pro Glu Pro Ser Thr Ala Pro Ser Thr Ser Phe Leu Leu Pro Met Gly
210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Gln Val Lys Phe Asn Trp Tyr Val Asp Gly Val Gln Val
```

```
            290                 295                 300

His Asn Ala Lys Thr Lys Pro Arg Glu Gln Gln Tyr Asn Ser Thr Tyr
305                 310                 315                 320

Arg Val Val Ser Val Leu Thr Val Leu His Gln Asn Trp Leu Asp Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
            450                 455                 460

Pro Gly Lys
465

<210> SEQ ID NO 4
<211> LENGTH: 215
<212> TYPE: PRT
<213> ORGANISM: Artificial Sequence
<220> FEATURE:
<223> OTHER INFORMATION: humanized antibody sequences

<400> SEQUENCE: 4

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
                20                  25                  30

Gly Asp Ser Tyr Met Asn Trp Tyr Gln Gln Lys Pro Gly Lys Ala Pro
                35                  40                  45

Lys Leu Leu Ile Tyr Ala Ala Ser Tyr Leu Glu Ser Gly Val Pro Ser
            50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
```

```
            180             185             190
His Lys Val Tyr Ala Cys Glu Val Thr His Gln Gly Leu Ser Ser Pro
        195                 200                 205
Val Thr Lys Ser Phe Asn Arg
    210             215
```

CONJUGATES OF BIOLOGICALLY ACTIVE MOLECULES TO FUNCTIONALIZED POLYMERS

CROSS-REFERENCE TO RELATED APPLICATIONS

This application is a divisional application of U.S. application Ser. No. 14/407,580, filed Dec. 12, 2014, which is a National Stage application under 35 U.S.C. § 371 of International Application No. PCT/IB2013/001885, having an international filing date of Jun. 12, 2013, which claims priority to U.S. Provisional Ser. Nos. 61/658,827, filed Jun. 12, 2012; 61/785,996, filed Mar. 14, 2013; 61/658,839, filed Jun. 12, 2012; 61/786,121, filed Mar. 14, 2013; 61/658,835, filed Jun. 12, 2012; 61/786,162, filed Mar. 14, 2013; 61/658,836, filed Jun. 12, 2012; 61/786,237, filed Mar. 14, 2013; 61/658,850, filed Jun. 12, 2012; 61/786,221, filed Mar. 14, 2013; 61/658,853, filed Jun. 12, 2012; 61/786,265, filed Mar. 14, 2013; 61/658,856, filed Jun. 12, 2012; and 61/786,287, filed Mar. 14, 2013; all of which are incorporated by reference in their entireties.

TECHNICAL FIELD

This document relates to conjugates of a biologically active molecule to a functionalized (e.g., mono- or bi-functional) polymers (e.g., polyethylene glycol and related polymers) as well as methods and materials for making and using such conjugates.

BACKGROUND

Pharmacokinetic and immune stimulating properties of proteins and synthetic drugs may be controlled by their conjugation to certain polymers. For example, polyethylene glycol (PEG) can be conjugated to proteins to achieve this effect (Fee and Van Alstine, *Chemical Engineering Science*, 61:924-934 (2006)). Such conjugation can take place if the relatively non-reactive hydroxyl groups present in PEG molecules are substituted by other, more reactive moieties (Jagur-Grudzinski, *Reactive & Functional Polymers*, 39:99-138 (1999)). A standard, linear PEG molecule is chemically a diol, which could suggest that the process of PEG derivatization and purification of products should be trivial. However, the polymeric nature of this diol, together with its amphiphilic properties can make these manipulations difficult. In some cases, the typical laboratory process for separation of difficult reaction mixtures, silica gel-based flash column chromatography, can fail for PEG with molecular weight higher than 1000. Neither crystallization nor precipitation appear adequate to achieve separation of PEG-containing materials, even if these methods can be used for efficient removal of other, contaminating substances with low molecular weight. Most reaction mixtures containing modified PEG molecules lack a reliable analytical method to control or to prove their composition. Polymers with functions that influence only minimally the hydrophobic properties of the polymer can be difficult to analyze by chromatography. The same applies for polymers with functions carrying only a minimal charge. This also applies for preparative chromatographic separation of charged polymers as described elsewhere for the separation of mono- and di-carboxyl modified PEG molecules (Drioli et al., *Reactive & Functional Polymers*, 48:119-128 (2001)).

Confirmation of results of the synthesis based on NMR can be useless, as long as one is not sure about the purity of the product, and this is typically only obtained by chromatographic methods. This unusual conclusion comes from observations that an equimolar mixture of non-derivatized polymer and bis-derivatized polymer will produce an NMR pattern identical to the pure mono-derivatized polymer. Mass spectrometry can be complicated since most PEG exists not in the form of a single component, but is rather a Gaussian population of different polymer lengths, centered on its average molecular weight. Thus, even if all distinct components of the same type should have their mass increased by the same factor, the presence of unreacted and bis-modified material can obscure the picture of the analysis. The literature discusses this problem only sporadically, and often nothing is mentioned about analysis of the product or its purification. Many authors make the impression that the process that they describe is ongoing with quantitative yield, and thus the quality of the product does not need to be analyzed or questioned. This non-scientific approach can be frequently encountered in the chemistry of PEG. There are many examples in the literature presenting synthetic procedures with four to five consecutive steps without a single analysis of the product at any of these steps, without any attempts to purifying the product, and assuming 100 percent purity at the end of the process. It is, therefore, not strange that researchers after closer testing question these products and their purity (Ananda et al., *Anal. Biochem.*, 374, 231-242 (2008)). A commonly accepted escape from the problem of selective modification is to work with a polymer that has one end blocked from the beginning by a stable chemical group, most often a methoxy group (mPEG). In theory, this blockage converts a PEG molecule to a monofunctional compound, and as such, it could be fully converted to the second derivatized form by increasing the amount of derivatizing reagent and/or time for reaction. Unfortunately, many of reactions commonly applied for derivatization of PEG are sluggish and only seldom go to completion. On the other hand, mPEG preparations contain significant percentages of PEG diol component. Moreover, the amount of this contamination increases with the length of mPEG, and this contamination can be hard to avoid. Consequently, derivatization will also result in formation of symmetrical, bis-derivatizated PEG, and its presence in the conjugating mixture results in formation of cross-linked products with unknown pharmacologic properties or a possible loss of protein activity. Therefore, pure, monofunctional polymers are usually preferred for protein modification, but one should be aware that purification of mPEG from its diol PEG contamination is practically impossible.

Nearly all of existing reactions, used today for derivatization of PEG, belong either to the alkylation-based or the acylation-based category. In the first case, the alkoxy anion, generated from PEG, is reacting with incoming electrophilic modifying reagent. Eventually, the activated PEG, subjected with a good leaving group, is itself an object of a nucleophilic attack. To this category belong processes resulting in thiolation, amination, azidation, and introduction of a carboxyl or an aldehyde group. Modified PEG's of this category will have their functional group connected directly to the PEG terminal carbon atom or these groups will be linked via an ether bond, a thioether bond, or a secondary amino group.

The second category, acylation, is based on a nucleophilic reaction of PEG's hydroxyl, (or another group present in a modified PEG—often an amino group), on an incoming acylating reagent. In many cases, this first acylation is followed by a second acylation that actually introduces the modification of interest to the PEG molecule. Functional groups incorporated by this method can be linked to the rest of PEG by an amido, a carbamido, urethane, thiourethane, or a simple ester group. These linking groups and the chemistry behind them belong to the very traditional methods of combining two chemical identities.

Polyethylene glycols (PEG) coupled to phosphoramidites are used for direct coupling of PEG molecules to synthetic nucleic acids. One example is 4,4'-dimethoxytrityl-polyethyleneglycol-[(2-cyanoethyl)-(N,N-diisopropyl)]-phosphoramidite. In these compounds, the phosphoramidite group is the part of the reactive functionality for linking the compound to a synthetic nucleic acid. It is designed to work in a completely water-free environment: In the presence of water, the phosphoramidite group can decompose instantaneously, making such PEG phosphoramidites inappropriate for conjugation to biological material in water-containing or aqueous solution. In particular, these PEG phosphoramidites can be inappropriate for conjugation to biological substances which are not soluble, stable or sufficiently reactive in non-aqueous media. Furthermore, already mildly acidic biological substances can decompose these PEG phosphoramidites. Finally, these PEG phosphoramidites contain a labile protecting group adjacent to the phosphorous atom which is specially designed to convert the intermediate phosphotriester to a phosphodiester. Phosphodiesters can be readily degraded enzymatically in vivo.

SUMMARY

This document provides conjugates of a biologically active molecule (e.g., TNF inhibitors, insulin, omalizumab, clotting factors, polypeptides that boost red or whit blood cell production, an antibody), or derivatives thereof to functionalized (e.g., mono- or bi-functional) polymers (e.g., polyethylene glycol and related polymers) as well as methods and materials for making and using such conjugates. The conjugates described herein can have an altered pharmacokinetic and pharmacodynamic profile, including, for example, one or more of reduced dosage frequency, extended circulation time, and reduced antigenic properties. The functionalized polymers include one or more linking groups selected from a phosphotriester, a phosphoramidate, a thiophosphotriester, and a thiophosphoramidate. For example, a biologically active molecule or a derivative thereof can be conjugated to a PEG polymer having at least one functional group at one terminus covalently bound to the rest of the polymer via a phosphotriester or phosphoramidate linking group. A biologically active molecule or a derivative thereof can be conjugated to a functionalized polymer provided herein that includes different linking groups at each of its termini. Also provided herein is a biologically active molecule or a derivative thereof conjugated to a functionalized polymer in which at least one terminus is modified with a blocking group (e.g., methoxy group) and at least another terminus is functionalized with a linking group as described herein.

As described herein, preparations of a functionalized polymer having one or more functional groups linked as described herein can be obtained in a manner where greater than 50 percent by weight (e.g., greater than 75 percent, greater than 80 percent, greater than 90 percent, greater than 95 percent, greater than 98 percent, and greater than 99 percent by weight) of the preparation is the desired functionalized polymer free from contaminants and can be used to conjugate to a biologically active molecule or a derivative thereof. As a person of ordinary skill in the art would understand, a functionalized polymer preparation includes a Gaussian population of different polymer lengths centered on an average molecular weight, and such a functionalized population would not be considered contaminating. For example, a mono-functionalized PEG population can be separated nearly quantitatively from contaminants of PEG functionalization (e.g., unreacted PEG and poly-functionalized PEG populations). The separation of a functionalized polymer provided herein can be facilitated through the use of a removable hydrophobic separation handle (e.g., a substituted or unsubstituted trityl group) which upon removal allows for preparative isolation of product (e.g., pure product), free or substantially free from unreacted polymer and poly-functionalized polymer.

Having the ability to isolate functionalized polymers in high purity can allow chemists to more easily control subsequent reactions or the purity of the downstream products, e.g., conjugates to a biologically active molecule or a derivative thereof. In some cases, having the ability to introduce all functional groups through a unified process using similar, mild reagents and reaction conditions can allow for the production of a functionalized polymer through a fast and nearly quantitative reaction.

The ability to isolate functionalized polymers quantitatively can allow chemists to more easily control subsequent reactions or the purity of conjugates of a biologically active molecule such as a TNF inhibitor, insulin, omalizumab, a clotting factor, a polypeptide that boosts red or white cell production, or an antibody, coupled to a functionalized polymer provided herein.

A linking group, in addition to linking the functional group or separation handle, can act as a linker between the polymer and a biologically active molecule or derivative thereof. For instance, a functionalized polymer of high purity can be coupled to a biologically active molecule or derivative thereof. In such conjugates, the linker can form covalent bonds to the polymer and a biologically active molecule or derivative thereof. The coupling can take place in an aqueous reaction medium.

Furthermore, the linking groups provided herein are generally resistant to chemical and enzymatic degradation, providing for stable storage and increased safety and efficacy in vivo.

In one aspect, this document features a method of making a biologically active molecule conjugate. The method includes reacting a biologically active molecule or a derivative thereof with a preparation comprising a water-soluble, non-peptidic, and non-nucleotidic polymer backbone having at least one terminus covalently bonded to a structure of formula (1) under conditions suitable for group M to react with a biologically active molecule or the derivative thereof:

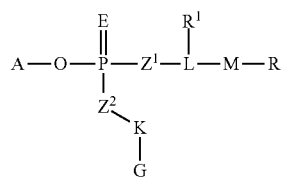

or a salt thereof, wherein A is the point of covalent bonding to the terminus of the polymer backbone; E is O or S; K is selected from the group consisting of: alkylene, alkyleneoxyalkylene, and oligomeric alkyleneoxyalkylene; G is selected from the group consisting of: hydrogen, alkoxy, and a hydrophobic separation handle; $Z^1$ and $Z^2$ are independently selected from O and NH, wherein only one of $Z^1$ and $Z^2$ can be NH; L is selected from the group consisting of: a divalent radical of a nucleoside, alkylene, alkyleneoxyalkylene, oligomeric alkyleneoxyalkylene, and unsubstituted and substituted arylene; M is a protected group that when deprotected is reactive with a biologically active molecule or derivative thereof or is a group reactive with a biologically active molecule or derivative thereof; R is absent or selected from the group consisting of: hydrogen, a protecting group, a hydrophobic separation handle, or an activating group; $R^1$ is absent or a hydrophobic separation handle; wherein when M is a protected group that when deprotected is reactive with a biologically active molecule or derivative thereof, then R is a protecting group or a hydrophobic separation handle; wherein when M is a group reactive with a biologically active molecule or derivative thereof, R is absent, hydrogen, or an activating group; and wherein only one of R, $R^1$, and G can be a hydrophobic separation handle. In some embodiments, the polymer backbone has from 2 to 100 termini. In some embodiments, only one termini of the polymer backbone is covalently bonded to the structure of formula (1). In some embodiments, only one termini of the polymer backbone is covalently bonded. In some embodiments, the polymer backbone has two termini. In some embodiments, only one termini of the polymer backbone is covalently bonded to the structure of formula (1). In some embodiments, both termini of the polymer backbone are covalently bonded to the structure of formula (1).

A polymer backbone can be selected from the group consisting of poly(alkylene glycol), poly(oxyethylated polyol), poly(olefinic alcohol), poly(α-hydroxy acid), poly(vinyl alcohol), polyoxazoline, and copolymers. For example, a polymer backbone can be poly(ethylene glycol). In some cases, a poly(ethylene glycol) has an average molecular weight from about 500 Da to about 100,000 Da.

In some embodiments, one of $Z^1$ and $Z^2$ is NH and the other is O. In some embodiments, $Z^1$ is O and $Z^2$ is NH. In some embodiments, $Z^1$ is NH and $Z^2$ is O. In some embodiments, both $Z^1$ and $Z^2$ are O.

The group reactive with a biologically active molecule or the derivative can be selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, and iodoacetamide.

In some embodiments, K is selected from the group consisting of: methylene, ethylene, propylene, isopropylene, butylene, isobutylene, sec-butylene, tert-butylene, and hexylene, or a residue from diethylene glycol, triethylene glycol, tetraethylene glycol or hexaethylene glycol.

In some embodiments, G is a substituted or unsubstituted trityloxy.

In some embodiments, L is a substituted or unsubstituted $C_1$-$C_{12}$ alkylene.

In some embodiments, R is selected from the group consisting of: trityl, monoalkoxytrityl, dialkoxytrityl, pixyl, alkoxypixyl, fluorenylmethyloxycarbonyl, trifluoroacetyl, acetal, and cyclic acetal.

In some embodiments, a group reactive with a biologically active molecule or the derivative is carboxyl and R is absent or selected from the group consisting of N-hydroxysuccinimidyl, p-nitrophenyl, or pentachlorophenyl.

In some embodiments, the preparation includes at least 50% by weight (e.g., at least 60%, 70%, 80%, 90%, 95%, or 98% by weight) of the water-soluble, non-peptidic, and non-nucleotidic polymer backbone having at least one terminus covalently bonded to a structure of formula (1).

In some embodiments, the method further can include (i) removing the hydrophobic separation handle(s) from the structure of formula (1) and (ii) optionally reacting the compound obtained in step (i) with an activating agent before reacting with a biologically active molecule or the derivative.

In some embodiments, the method further can include removing the hydrophobic separation handle(s) from the structure of formula (1) after reacting with a biologically active molecule or the derivative.

This document also features a conjugate, or a pharmaceutically acceptable salt thereof, that includes a water-soluble, non-peptidic, and non-nucleotidic polymer backbone as in a structure of formula (9):

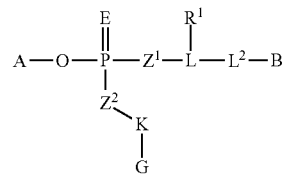

or a salt thereof,
wherein A is the point of covalent bonding to the terminus of the polymer backbone; E is O or S; K is selected from the group consisting of: alkylene, alkyleneoxyalkylene, and oligomeric alkyleneoxyalkylene; G is selected from the group consisting of: hydrogen, alkoxy, and a hydrophobic separation handle; $Z^1$ and $Z^2$ are independently selected from O and NH, wherein only one of $Z^1$ and $Z^2$ can be NH; L is selected from the group consisting of: a divalent radical of a nucleoside, alkylene, alkyleneoxyalkylene, oligomeric alkyleneoxyalkylene, and unsubstituted and substituted arylene; $R^1$ is absent or a hydrophobic separation handle, wherein only one of $R^1$ and G can be a hydrophobic separation handle; $L^2$ is a covalent linking moiety between L on the polymer backbone and B; and B is a biologically active molecule or a derivative thereof.

This document also features a method of making a biologically active molecule conjugate. The method includes reacting a biologically active molecule or a derivative thereof with a preparation that includes a compound of formula (2) under conditions suitable for group M to react with a biologically active molecule or the derivative thereof:

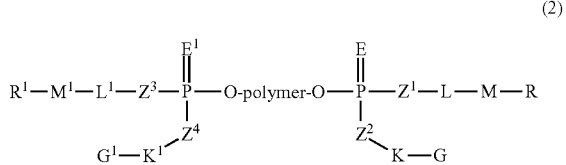

(2)

or a salt form thereof, wherein polymer is a linear, water-soluble, non-peptidic, and non-nucleotidic polymer backbone, wherein each linking group is bonded at a different terminus of the polymer; E and $E^1$ are independently O or S; K and $K_1$ are independently selected from the group consisting of: alkylene, alkyleneoxyalkylene, and oligomeric alkyleneoxyalkylene; G and $G_1$ are independently absent or are selected from the group consisting of: alkoxy and a hydrophobic separation handle; each pair of $Z^1$ and $Z^2$ and $Z^3$ and $Z^4$ are independently selected from O and NH, wherein only one of each pair of $Z^1$ and $Z^2$ and $Z^3$ and $Z^4$ can be NH; L and $L^1$ are independently selected from the group consisting of: a divalent radical of a nucleoside, alkylene, alkyleneoxyalkylene, oligomeric alkyleneoxyalkylene, and unsubstituted and substituted arylene; M and $M^1$ are independently selected from a protected group that when deprotected is reactive with a biologically active molecule or the derivative or a group reactive with a biologically active molecule or the derivative, wherein M and $M^1$ are different; and R and $R^1$ are independently absent, hydrogen, a protecting group, or an activating group; wherein when M is a protected group that when deprotected is reactive with a biologically active molecule or the derivative, then R is a protecting group or a hydrophobic separation handle; wherein when M is a group reactive with a biologically active molecule or the derivative, R is absent, hydrogen, or an activating group; wherein when $M^1$ is a protected group that when deprotected is reactive with a biologically active molecule or the derivative, then $R^1$ is a protecting group or a hydrophobic separation handle; and wherein when $M^1$ is a group reactive with a biologically active molecule or the derivative, $R^1$ is absent, hydrogen, or an activating group.

In some embodiments, one of $Z^1$ and $Z^2$ is NH and the other is O. In some embodiments, $Z^1$ is O and $Z^2$ is NH. In some embodiments, $Z^1$ is NH and $Z^2$ is O. In some embodiments, both $Z^1$ and $Z^2$ are O. In some embodiments, one of $Z^3$ and $Z^4$ is NH and the other is O. In some embodiments, $Z^3$ is O and $Z^4$ is NH. In some embodiments, $Z^3$ is NH and $Z^4$ is O. In some embodiments, both $Z^3$ and $Z^4$ are O.

In some embodiments, the group reactive with a biologically active molecule or the derivative thereof is selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, and iodoacetamide.

In some embodiments, K and $K^1$ are independently selected from the group consisting of: methylene, ethylene, propylene, isopropylene, butylene, isobutylene, sec-butylene, tert-butylene, and hexylene, or a residue from diethylene glycol, triethylene glycol, tetraethylene glycol or hexaethylene glycol.

In some embodiments, G and $G^1$ is independently seleceted from a substituted or unsubstituted trityloxy.

In some embodiments, L and $L^1$ is independently a substituted or unsubstituted $C_1$-$C_{12}$ alkylene.

In some embodiments, R or $R^1$ is independently selected from the group consisting of: trityl, monoalkoxytrityl, dialkoxytrityl, pixyl, alkoxypixyl, fluorenylmethyloxycarbonyl, trifluoroacetyl, acetal, cyclic acetal, and combinations of thereof.

In some embodiments, the polymer is poly(ethylene glycol). For example, a poly(ethylene glycol) having an average molecular weight from about 500 Da to about 100,000 Da.

In some embodiments, the preparation includes at least 50% by weight (e.g., at least 60%, 70%, 80%, 90%, 95%, or 98% by weight) of the water-soluble, non-peptidic, and non-nucleotidic polymer backbone having at least one terminus covalently bonded to a structure of formula (2).

In some embodiments, the method further can include (i) removing the hydrophobic separation handle(s) from the structure of formula (1) and (ii) optionally reacting the compound obtained in step (i) with an activating agent before reacting with a biologically active molecule or the derivative.

This document also features a conjugate, or a pharmaceutically acceptable salt thereof, including a structure of formula (10):

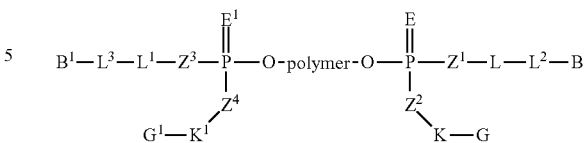

(10)

or a salt form thereof, wherein: polymer is a linear, water-soluble, non-peptidic, and non-nucleotidic polymer backbone, wherein each linking group is bonded at a different terminus of the polymer; E and $E^1$ are independently O or S; K and $K_1$ are independently selected from the group consisting of: alkylene, alkyleneoxyalkylene, and oligomeric alkyleneoxyalkylene; G and $G_1$ are independently absent or are selected from the group consisting of: alkoxy and a hydrophobic separation handle; each pair of $Z^1$ and $Z^2$ and $Z^3$ and $Z^4$ are independently selected from O and NH, wherein only one of each pair of $Z^1$ and $Z^2$ and $Z^3$ and $Z^4$ can be NH; L and $L^1$ are independently selected from the group consisting of: a divalent radical of a nucleoside, alkylene, alkyleneoxyalkylene, oligomeric alkyleneoxyalkylene, and unsubstituted and substituted arylene; $L^2$ is a covalent linking moiety between L on the polymer backbone and B; $L^3$ is a covalent linking moiety between L on the polymer backbone and $B^1$; and B and $B^1$ are independently a biologically active molecule or a derivative of a biologically active molecule (e.g., a TNF inhibitor, a derivative of a TNF inhibitor, insulin, a derivative of insulin, omalizumab, a derivative of omalizumab, a clotting factor, a derivative of a clotting factor, a polypeptide that boosts red or white cell production, a derivative of a polypeptide that boosts red or white cell production, an antibody, or a derivative of an antibody), a drug, a detectable group, a separation moiety, wherein at least one of B and $B^1$ is a biologically active molecule or a derivative of a biologically active molecule. For example, B and $B^1$ each can be selected from the group consisting of: a TNF inhibitor, insulin, omalizumab, a clotting factor, a polypeptide that boosts red or white cell production, and an antibody.

This document also features a method of making a biologically active molecule conjugate. The method includes reacting a biologically active molecule or a derivative thereof with a preparation that includes a compound of formula (3):

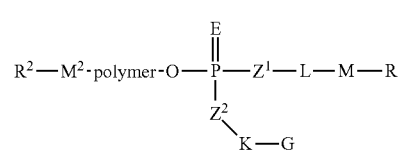

(3)

or a salt form thereof,
wherein: polymer is a linear, water-soluble, non-peptidic, and non-nucleotidic polymer backbone, wherein $M^2$ and the phosphonate-derived functional group are bonded at a different terminus of the polymer; E and $E^1$ are independently O or S; K is selected from the group consisting of: alkylene, alkyleneoxyalkylene, and oligomeric alkyleneoxyalkylene; G is selected from the group consisting of: hydrogen, alkoxy, and a hydrophobic separation handle; $Z^1$ and $Z^2$ are independently selected from O and NH, wherein only one of $Z^1$ and $Z^2$ can be NH; L is selected from the group consisting of: a divalent radical of nucleoside, alkylene, alkyleneoxyalkylene, oligomeric alkyleneoxyalkylene, and unsubstituted and substituted arylene; M is selected from a protected group that when deprotected is reactive with a biologically active molecule or the derivative or a group reactive with a biologically active molecule or the derivative; $M^2$ is selected from O, S or NH; and R is absent, a protecting group, a hydrophobic separation handle, or an activating group; $R^2$ is hydrogen or a protecting group; wherein when M is a protected group that when deprotected is reactive with a biologically active molecule or the derivative, then R is a protecting group or a hydrophobic separation handle; and wherein when M is a group reactive with a biologically active molecule or the derivative, R is absent, hydrogen, or an activating group.

In some embodiments, one of $Z^1$ and $Z^2$ is NH and the other is O. In some embodiments, $Z^1$ is O and $Z^2$ is NH. In some embodiments, $Z^1$ is NH and $Z^2$ is O. In some embodiments, both $Z^1$ and $Z^2$ are O.

A group reactive with a biologically active molecule or the derivative can be selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, and iodoacetamide.

In some embodiments, K is selected from the group consisting of: methylene, ethylene, propylene, isopropylene, butylene, isobutylene, sec-butylene, tert-butylene, and hexylene, or a residue from diethylene glycol, triethylene glycol, tetraethylene glycol or hexaethylene glycol.

In some embodiments, G is a substituted or unsubstituted trityloxy. For example, G can be a monoalkoxy substituted trityloxy group or a dialkoxy substituted trityloxy group.

In some embodiments, $R^2$ is absent or selected from the group consisting of trityl, monoalkoxytrityl, dialkoxytrityl, pixyl, alkoxypixyl, fluorenylmethyloxycarbonyl, alkylcarboxyl, benzoyl, tetrahydropyranyl, and methyl.

In some embodiments, the polymer is poly(ethylene glycol).

In some embodiments, the preparation includes at least 50% by weight (e.g., at least 60%, 70%, 80%, 90%, 95%, or 98% by weight) of the water-soluble, non-peptidic, and non-nucleotidic polymer backbone having at least one terminus covalently bonded to a structure of formula (3).

In some embodiments, the method further can include (i) removing the hydrophobic separation handle(s) from the structure of formula (1) and (ii) optionally reacting the compound obtained in step (i) with an activating agent before reacting with a biologically active molecule or the derivative.

In some embodiments, the method further can include removing the hydrophobic separation handle(s) from the structure of formula (1) after reacting with a biologically active molecule or the derivative.

This document also features a conjugate, or a pharmaceutically acceptable salt thereof, that includes a compound of formula (11):

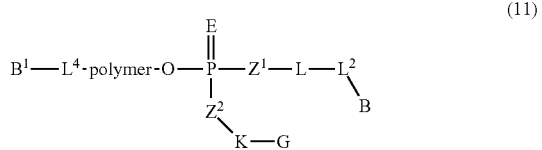

(11)

or a salt form thereof, wherein: polymer is a linear, water-soluble, non-peptidic, and non-nucleotidic polymer backbone, wherein $M^2$ and the phosphonate-derived functional group are bonded at a different terminus of the polymer; E and $E^1$ are independently O or S; K is selected from the group consisting of: alkylene, alkyleneoxyalkylene, and oligomeric alkyleneoxyalkylene; G is selected from the group consisting of: hydrogen, alkoxy, and a hydrophobic separation handle; $Z^1$ and $Z^2$ are independently selected from O and NH, wherein only one of $Z^1$ and $Z^2$ can be NH; L is selected from the group consisting of: a divalent radical of nucleoside, alkylene, alkyleneoxyalkylene, oligomeric alkyleneoxyalkylene, and unsubstituted and substituted arylene; $L^2$ is a covalent linking moiety between L on the polymer backbone and B; $L^4$ is a covalent linking moiety between L on the polymer backbone and $B^1$; and B and $B^1$ are independently a biologically active molecule or a derivative of a biologically active molecule (e.g., a TNF inhibitor, a derivative of a TNF inhibitor, insulin, a derivative of insulin, omalizumab, a derivative of omalizumab, a clotting factor, a derivative of a clotting factor, a polypeptide that boosts red or white cell production, a derivative of a polypeptide that boosts red or white cell production, an antibody, or a derivative of an antibody), a biologic other than the biologically active molecule, a drug, a detectable group, a separation moiety, wherein at least one of B and $B^1$ is a biologically active molecule or a derivative of a biologically active molecule. For example, B and $B^1$ each can be selected from the group consisting of: a TNF inhibitor, insulin, omalizumab, a clotting factor, a polypeptide that boosts red or white cell production, an antibody, This document also features a method of preparing a compound that includes a water-soluble, non-peptidic, and non-nucleotidic polymer backbone having at least one terminus covalently bonded to a structure of formula (9):

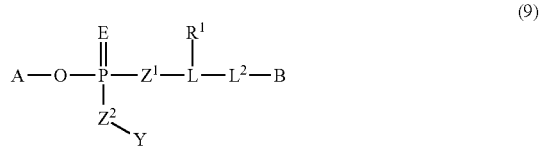

(9)

or a salt thereof, wherein: A is the point of covalent bonding to the terminus of the polymer backbone; E is O or S; Y represents an optionally substituted residue selected from alkyl, cycloalkyl, heterocyclyl, aryl, and heteroaryl; $Z^1$ and $Z^2$ are independently selected from O and NH, wherein only one of $Z^1$ and $Z^2$ can be NH; L is selected from the group consisting of: a divalent radical of a nucleoside, alkylene, alkyleneoxyalkylene, oligomeric alkyleneoxyalkylene, and unsubstituted and substituted arylene; L2 is a covalent linking moiety between L on the polymer backbone and B; and B is a biologically active molecule or a derivative thereof. The method includes (a) providing a composition comprising a compound of formula (8):

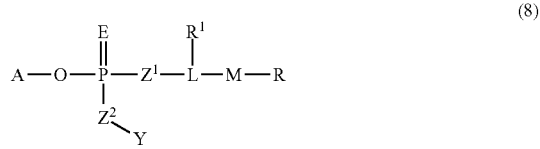

(8)

wherein: A is the point of covalent bonding to the terminus of the polymer backbone; E is O or S; Y represents an optionally substituted residue selected from alkyl, cycloalkyl, heterocyclyl, aryl, and heteroaryl; $Z^1$ and $Z^2$ are independently selected from O and NH, wherein only one of $Z^1$ and $Z^2$ can be NH; L is selected from the group consisting of: a divalent radical of a nucleoside, alkylene, alkyleneoxyalkylene, oligomeric alkyleneoxyalkylene, and unsubstituted and substituted arylene; M is a protected group that when deprotected is reactive with a biologically active molecule or a derivative thereof; R is a hydrophobic separation handle; $R^1$ is absent or a hydrophobic separation handle; and (b) removing the hydrophobic separation handle(s);

(c) optionally reacting the compound obtained in step (b) with an activating agent; and (d) reacting the compound obtained in step (b), or, optionally in step (c), with a biologically active molecule or a derivative thereof.

In some embodiments, one of $Z^1$ and $Z^2$ is NH and the other is O. In some embodiments, $Z^1$ is O and $Z^2$ is NH. In some embodiments, $Z^1$ is NH and $Z^2$ is O. In some embodiments, both $Z^1$ and $Z^2$ are O.

The protected group M can be, when deprotected, selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, and iodoacetamide.

In some embodiments, R is selected from the group consisting of: trityl, monoalkoxytrityl, dialkoxytrityl, pixyl, alkoxypixyl, fluorenylmethyloxycarbonyl, trifluoroacetyl, acetal, and cyclic acetal.

In some embodiments, the polymer backbone is selected from the group consisting of poly(alkylene glycol), poly(oxyethylated polyol), poly(olefinic alcohol), poly(α-hydroxy acid), poly(vinyl alcohol), polyoxazoline, and copolymers. For example, the polymer backbone can be poly(ethylene glycol).

In some embodiments, reaction step (d) is carried out in the presence of water or a protic solvent. In some embodiments, the compound of formula (8) is essentially pure.

In some embodiments, the compound of formula (8) comprises at least 98% by weight of the composition.

In one aspect, this document features a composition that includes any of the conjugates described herein and a pharmaceutically acceptable excipient. The polymer backbone of the conjugate can be poly(ethylene glycol).

In yet another aspect, this document features a method of treating a patient diagnosed with a disease selected from the group consisting of: an inflammatory disease; diabetes; asthma; hemophilia, factor VII deficiency, or other clotting disorder; The method includes administering to the patient an effective amount of any of the conjugates described herein. The polymer backbone of the conjugate can be poly(ethylene glycol).

This disclosure utilizes phosphoramidites as reagents interacting with polymers to form a phosphotriester-type of linker between a polymer and linking group. A similar process is used commonly in the chemistry of nucleic acids. Formation of a phosphotriester bond, in the chemistry of nucleic acids, is often followed by its partial hydrolysis (deprotection) to the phosphodiester bond, because phosphodiester bonds are naturally occurring. The present disclosure provides an uncommon and unnatural phosphotriester linkage which is enzymatically resistant, offering a stable linker between a polymer and a biologically active molecule such as a TNF inhibitor, insulin, omalizumab, a clotting factor, a polypeptide that boosts red or white cell production, an antibody, or a derivative thereof.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 shows SEQ ID NO.1, the amino acid sequence omalizumab (XOLAIR™).

FIG. 7 shows SEQ ID NO.2, the amino acid sequence of insulin.

FIG. 10 shows SEQ ID NO.3, the amino acid sequence etanercept (ENBREL®).

DETAILED DESCRIPTION

Figure 2:
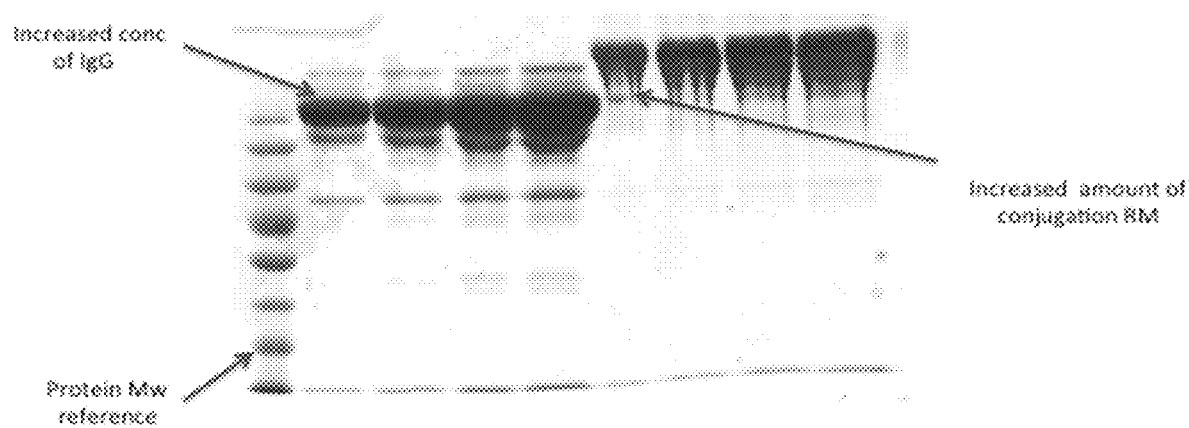
FIG. 2 provides a photograph of a SDS electrophoresis gel of the product of the conjugation of omalizumab to a PEG reagent as provided herein stained with Coomassie blue.

This document provides conjugates of a biologically active molecule (e.g., a TNF inhibitor, insulin, omalizumab, a clotting factor, a polypeptide that boosts red or white cell production, or an antibody) or a derivative thereof and functionalized (e.g., mono- or bi-functional) polymers (e.g., polyethylene glycol and related polymers) as well as methods and materials for making and using such conjugates.

Non-limiting examples of a biologically active molecule include a TNF inhibitor, insulin, omalizumab, a clotting factor, a polypeptide that boosts red or white cell production, and an antibody.

As used herein, the term "TNF inhibitor" includes antibodies or fusion proteins that bind to TNF alpha. Non-limiting examples of TNF inhibitors include etanercept (Enbrel®, sold by Amgen and Pfizer); infliximab (Remicade®, sold by Janssen Biotech, Inc.); adalimumab (Humira®, sold by Abbott Laboratories); certolizumab pegol (Cimzia®); and Golimumab (Simponi®, sold by Janssen Biotech, Inc.).

Etanercept (Enbrel®) is a fusion protein of human soluble TNF receptor 2 to the Fc component of human IgG$_1$. It is a TNF inhibitor that binds to TNF alpha and is used to treat inflammatory diseases e.g., rheumatoid arthritis, plaque psoriasis, psoriatic arthritis, juvenile idiopathic arthritis (JIA), and ankylosing spondylitis (AS)).

Infliximab (Remicade®) is a chimeric mouse-human monoclonal antibody that specifically binds TNF alpha. It is used for the treatment of psoriasis, Crohn's disease, ankylosing spondylitis, psoriatic arthritis, rheumatoid arthritis, and ulcerative colitis.

Adalimumab (Humira®) is a fully human monoclonal antibody that binds TNF alpha and is used for the treatment of rheumatoid arthritis, psoriatic arthritis, ankylosing spondylitis, Crohn's disease, moderate to severe chronic psoriasis, and juvenile idiopathic arthritis.

Certolizumab pegol (Cimzia®) is a pegylated fragment Fab' of humanized TNF inhibitor monoclonal antibody.

Golimumab (Simponi®) is a human monoclonal antibody that targets TNF alpha, and is used to treat severely active rheumatoid arthritis, psoriatic arthritis, and ankylosing spondylitis.

As used herein, the term "insulin" includes human and other mammalian insulin polypeptides as well as insulin analogs that have one or more amino acid substitutions. Human insulin is composed of A and B polypeptide chains bound together by disulfide bonds, where the A chain is 21 amino acids in length and the B chain is 30 amino acids in length, 51 amino acids in total. Insulin and analogs can be recombinantly produced (e.g., in a non-pathogenic organism). Non-limiting examples of suitable insulin analogs include insulin lispro (HUMALOG, Eli Lilly), insulin aspart (NovoLog/NovoRapid, Novo Nordisk), insulin detemir (Levemir®, Novo Nordisk), Insulin glargine (Lantus®, Sanofi-Aventis), and insulin glulisine (Apidra®, Sanofi-Aventis). See Werner and Chantelau, *Diabetol Metab Syndr.* 3: 13 (2011) for a comparison of the bioactivity of human insulin and insulin analogs.

Insulin lispro is a rapid-acting human insulin analog used to lower blood glucose levels, and contains a substitution of lysine for proline at position B28, and a substitution of proline for lysine at position B29.

Insulin aspart is a rapid-acting human insulin analog used to lower blood glucose levels, and contains a substitution of an aspartic acid for proline at position B28.

Insulin detemir is a long-acting insulin analog used for maintaining the basal level of insulin. Insulin determir contains myristic acid is bound to the lysine at position B29.

Insulin glargine is a long-acting insulin analog used for lower blood glucose, and contains a substitution of a glycine for asparagine at position A21 and contains two arginines added to the C-terminus of the B-chain.

Insulin glulisine is a rapid acting human insulin analog used to lower blood glucose levels, and contains a substitution of a lysine for asparagine at position B3 and the substitution of a glutamic acid for lysine at position B29.

Omalizumab (Xolair®, Novartis Pharmaceuticals, East Hanover, N.J.; Genentech Inc., South San Francisco, Calif.) is a recombinant humanized monoclonal antibody (rhuMAb-E25) for treatment of moderate to severe persistent asthma. Omalizumab inhibits the binding of IgE to the high-affinity IgE receptor FcεRI by binding to an epitope on IgE that overlaps with the site to which FcεRI binds. Consequently, circulating free IgE is reduced, IgE is prevented from attaching to mast cells and basophils, and FcεRI receptor expression is down-regulated. See, e.g., Sandstrom, *J Asthma Allergy*, 2: 49-62 (2009).

As used herein, the term "clotting factor" includes human or other mammalian clotting factors such as factor VII and activated factor VII (factor VIIa), factor VIII and activated factor VIII (factor VIIIa), factor IX and activated factor IX (factor IXa), antithrombin, human fibrinogen/human thrombin, and protein C and activated protein C (APC). Such clotting factors can be recombinantly produced.

Factor VII functions in the initial stage of blood clotting and is a key element in forming blood clots. The inactive precursor has low enzyme activity that is increased by proteolytic cleavage to form factor VIIa. This activation can be catalyzed by factor Xa as well as by VIIa-tissue factor, an integral membrane protein found in a number of cell types. See Fiore, et al., *J. Biol. Chem.*, 269:143-149 (1994). Factor VIIa can activate blood clotting factors IX and X. Eptacog alfa (activated) (sold by Novo Nordisk) can be used to replace missing factor VII in patients with factor VII deficiency and also can be used in haemophilia patients who have developed inhibitors to factor VIII or IX.

Factor VIII is activated by thrombin (Factor IIa), and then can interact with Factor IXa in the coagulation cascade. It is a cofactor to Factor IXa in the activation of Factor X, which, in turn, with its cofactor Factor Va, activates more thrombin. Thrombin cleaves fibrinogen into fibrin which polymerizes and crosslinks (using Factor XIII) into a blood clot. Factor VIII deficiency results in hemophilia A and Factor IX deficiency causes hemophilia B. Moroctocog alfa (glycoprotein (trade name ReFacto®, Xyntha®) are commercially available for Factor VIII replacement therapy. Factor VIII replacement therapy is limited due to development of high-titer inhibitory factor VIII antibodies in some patients. Nonacog alfa (Benefix®) is a human recombinant factor IX product used in treating hemophilia B patients.

Antithrombin is a small glycoprotein that inactivates several enzymes of coagulation system. Its activity enhanced by heparin. Antithrombin alfa (e.g., ATryn®) is commercially available.

Protein C is activated by thrombin in the presence of thrombomodulin, an integral membrane protein of endothelial cells. Esmon, et al., *J. Biol. Chem.*, 257:859-864 (1982). Activated protein C (APC) degrades factors Va and VIIIa in combination with its cofactor, protein S. Resistance to APC is the most common form of inherited thrombosis disease. Dahlback, *Blood,* 85:607-614 (1995).

As used herein, the term "polypeptide that boosts red blood cell production" includes human erythropoietin (e.g., epoetin alpha (Epogen®, Amgen), epoetin beta (NeoRecormon®, Roche), epoetin theta (Eporatio®), or epoetin zeta) and other mammalian erythropoetin polypeptides as well as analogs that have one or more amino acid substitutions (e.g., darbepoetin alpha (Aranesp®, Amgen)) or other chemical modifications. As used herein, the term "polypeptide that boosts white blood cell production" includes granulocyte colony-stimulating factor (G-CSF) analogs such as filgrastim (e.g., Neupogen®), which is identical to human G-CSF except for the addition of an N-terminal methionine necessary for expression in *E. coli*. Figrastim is nonglycosylated. Such polypeptides can be recombinantly produced.

Epoetin alpha, beta, theta, and zeta are structurally similar and have the same polypeptide receptor binding sites. However, there are subtle differences in the glycosylation patterns of different types of epoetins. See Sergei et al., *Arch Drug Inf.,* 4(3): 33-41 (2011); and Storring et al., *Br J Haematol.* 100(1):79-89 (1998). Darbepoetin is a 165-amino acid protein that differs from recombinant human erythropoietin in containing 5 N-linked oligosaccharide chains, whereas recombinant human erythropoietin contains 3 chains. The two additional N-glycosylation sites result from amino acid substitutions in the erythropoietin peptide backbone. The additional carbohydrate chains increase the approximate molecular weight of the glycoprotein from 30,000 to 37,000 daltons.

Non-limiting examples of antibodies that can be conjugated to a functionalized polymer include, abatacept (Orencia®), alemtuzumab (marketed as Campath, MabCampath or Campath-1H); basiliximab (Simulect®), belimumab (Benlysta®), besilesomab (Scintimun®), bevacizumab (Avastin®), canakinumab (Ilaris®), catumaxomab (Removab®), cetuximab (Erbitux®), denosumab (Prolia®, Xgeva®), eculizumab (Soliris®), ipilimumab (also known as MDX-010 or MDX-101, Yervoy®), natalizumab (Tysabri®), ofatumumab (Arzerra®), palivizumab (Synagis®), panitumumab (Vectibix®), ranibizumab (Lucentis®), rituximab (Rituxan®, MabThera®), tocilizumab (Actemra®, RoActemra®), trastuzumab (Herceptin®), and ustekinumab (Stelara®).

The antibody also can be an antibody drug conjugate (ADC). An ADC can include, for example, an antibody such as a monoclonal antibody, or antibody fragment such as a single-chain variable fragment, linked to a drug (e.g., a cytotoxic drug). In some embodiments, the antibody or fragment and drug can be linked via a cleavable linker (e.g., a disulfide-based linker or peptide linker). In some embodiments, the antibody or fragment and drug can be linked via a noncleavable linker.

For example, this document provides an antibody or a derivative thereof such as abatacept (Orencia®), alemtuzumab (marketed as Campath, MabCampath or Campath-1H); basiliximab (Simulect®), belimumab (Benlysta®), besilesomab (Scintimun®), bevacizumab (Avastin®), canakinumab (Ilaris®), catumaxomab (Removab®), cetuximab (Erbitux®), denosumab (Prolia®, Xgeva®), eculizumab (Soliris®), ipilimumab (also known as MDX-010 or MDX-101, Yervoy®), natalizumab (Tysabri®), ofatumumab (Arzerra®), palivizumab (Synagis®), panitumumab (Vectibix®), ranibizumab (Lucentis®), rituximab (Rituxan®, MabThera®), tocilizumab (Actemra®, RoActemra®), trastuzumab (Herceptin®), or ustekinumab (Stelara®) conjugated to functionalized PEG polymers.

In some embodiments, a biologically active molecule can be agalsidase alfa (Replagal®), agalsidase beta (Fabrazyme®), alglucosidase alfa (Myozyme®), anakinra (Kineret®), bortezomib (Velcade®), conestat alfa (Ruconest®), choriogonadotropin alfa (e.g., Ovidrel®), cinacalcet (Sensipar®), Corifollitropin alfa (Elonva®), dibotermin alfa (InductOs®), eltrombopag (Promacta®), eptotermin alfa (Osigraft®), erlotinib (Tarceva®), follitropin alfa/lutropin alfa, follitropin beta, galsulfase (Naglazyme®), Gefitinib (Iressa®), Human normal immunoglobulin, human normal immunoglobulin (ivig), human normal immunoglobulin (SCIg), idursulfase (Elaprase®), Imiglucerase (Cerezyme®), interferon alfa-2b, interferon beta-1a, interferon beta-1b, Lapatinib (Tykerb®, Tyverb®), Laronidase (Aldurazyme®), Pazopanib (Votrient), pegaptanib, pegfilgrastim, peginterferon alfa-2b, Rasburicase (Elitek®), Reteplase (Retavase®), Somatropin, Sorafenib (Nexavar®), Tenecteplase (TNKase), thyrotropin alfa, Vandetanib (Caprelsa®), or Vemurafenib (Zelboraf®).

The conjugates described herein can have an altered pharmacokinetic and pharmacodynamic profile, including, for example, one or more of reduced dosage frequency, extended circulation time, and reduced antigenic properties. As described herein, a biologically active molecule or a derivative thereof can be is conjugated to a functionalized polymer that includes one or more linking groups selected from a phosphotriester, a phosphoramidate, a thiophosphotriester, and a thiophosphoramidate. Suitable functionalized polymers can include different linking groups at each of its termini. A suitable functionalized polymer also can be modified at at least one terminus with a blocking group (e.g., methoxy group) and functionalized at at least another terminus with a linking group as described herein.

For example, this document provides a biologically active molecule or a derivative thereof conjugated to functionalized PEG polymers. In some cases, a functionalized PEG polymer has one terminus containing a functional group covalently bound via a phosphotriester, a phosphoramidate, a thiophosphotriester, and a thiophosphoramidate linking group.

In some cases, a PEG polymer is a linear PEG polymer (i.e., having two termini). A linear PEG polymer can be functionalized as described herein at one or both termini with the same or different functional group linked via the same or different linking groups. In some cases, one of the termini of a linear PEG polymer is blocked with a blocking group (e.g., methoxy or a protecting group) and the other termini is functionalized with a functional group linked as described herein. In some cases, one of the termini of a linear PEG polymer is functionalized with a phosphotriester linking group and the other termini is functionalized with a phosphoramidate linking group. In other cases, both termini are functionalized with the same or different phosphotriester linking groups. In yet other cases, both termini are functionalized with the same or different phosphoramidate linking groups.

Definitions

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

The term "alkyl" includes straight-chain alkyl groups (e.g., methyl, ethyl, propyl, butyl, pentyl, hexyl, heptyl, octyl, nonyl, decyl, etc.) and branched-chain alkyl groups (e.g., isopropyl, tert-butyl, isobutyl, etc.). In certain embodiments, a straight chain or branched chain alkyl has twelve or fewer carbon atoms in its backbone (e.g., $C_{1-12}$ for straight chain; $C_{3-12}$ for branched chain). The term $C_{1-12}$ includes alkyl groups containing 1 to 12 carbon atoms.

The term "alkenyl" includes aliphatic groups that may or may not be substituted, as described above for alkyls, containing at least one double bond and at least two carbon atoms. For example, the term "alkenyl" includes straight-chain alkenyl groups (e.g., ethenyl, propenyl, butenyl, pentenyl, hexenyl, heptenyl, octenyl, nonenyl, and decenyl) and branched-chain alkenyl groups. In certain embodiments, a straight chain or branched chain alkenyl group has twelve or fewer carbon atoms in its backbone (e.g., $C_{2-12}$ for straight chain; $C_{3-12}$ for branched chain). The term $C_{2-12}$ includes alkenyl groups containing 2 to 12 carbon atoms.

The term "alkynyl" includes unsaturated aliphatic groups analogous in length and possible substitution to the alkyls described above, but which contain at least one triple bond and two carbon atoms. For example, the term "alkynyl" includes straight-chain alkynyl groups (e.g., ethynyl, propynyl, butynyl, pentynyl, hexynyl, heptynyl, octynyl, nonynyl, and decynyl) and branched-chain alkynyl groups. In certain embodiments, a straight chain or branched chain alkynyl group has twelve or fewer carbon atoms in its backbone (e.g., $C_{2-12}$ for straight chain; $C_{3-12}$ for branched chain). The term $C_{2-6}$ includes alkynyl groups containing 2 to 12 carbon atoms.

The term "alkylene" by itself or as part of another molecule means a divalent radical derived from a linear or branched alkane, as exemplified by $(-CH_2-)_n$, wherein n may be 1 to 24 (e.g., 1 to 20, 1 to 18, 1 to 16, 1 to 15, 1 to 12, 1 to 10, 1 to 8, 1 to 6, 1 to 5, 1 to 4, 1 to 3, 1 to 2, 2 to 24, 2 to 12, 2 to 8). By way of example only, such groups include, but are not limited to, groups having 10 or fewer carbon atoms such as the structures $-CH_2CH_2-$ and $-CH_2CH_2CH_2CH_2-$. A "lower alkyl" or "lower alkylene" is a shorter chain alkyl or alkylene group, generally having eight or fewer carbon atoms.

The term "alkoxy" is used in its conventional sense, and refers to alkyl groups linked to molecules via an oxygen atom. In some embodiments, an alkoxy has twelve or fewer carbon atoms in its backbone (e.g., a $C_{1-12}$ alkoxy). For example, $C_{1-10}$, $C_{1-8}$, $C_{1-6}$, $C_{1-4}$, $C_{1-3}$, or $C_{1-2}$. Non-limiting examples of an alkoxy group include methoxy, ethoxy, propoxy, butoxy, and hexoxy.

The term "alkyleneoxyalkylene," as used herein, refers to a divalent radical derived from a linear or branched alkyloxyalkane, as exemplified, but not limited by, $-CH_2-CH_2-O-CH_2-CH_2-$ and $-CH_2-CH_2-O-$. By way of example only, such groups include, but are not limited to, groups having the formula $-(CH_2)_n-O-(CH_2)_m-$, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18) and m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18).

The term "oligomeric alkyleneoxyalkylene" refers to p-repetitive alkyleneoxyalkylene wherein p is an integer of between 2 and 24 (e.g., 2 to 20, 2 to 18, 2 to 16, 2 to 15, 2 to 12, 2 to 10, 2 to 8, 2 to 6, 2 to 5, 2 to 4, 2 to 3). By way of example only, such groups include, but are not limited to, groups having the formula $-((CH_2)_n-O-(CH_2)_m)_p-$, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In general, the term "arylene" by itself or as part of another molecule means a divalent radical derived from an aryl, including, for example, 5- and 6-membered single-ring aromatic groups, such as benzene and phenyl. Furthermore, the term "arylene" includes a divalent radical derived from a multicyclic aryl group, e.g., tricyclic, bicyclic, such as naphthalene and anthracene.

The term "substituted" means that an atom or group of atoms replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. In some cases, two sites of substitution may come together to form a 3-10 membered cycloalkyl or heterocycloalkyl ring.

Substituents include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, substituted phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, $-(CH_2)_m-O-(C_1$-$C_{10}$ alkyl) wherein m is from 1 to 8, aryl, substituted aryl, substituted alkoxy, fluoroalkyl, heterocyclic radical, substituted heterocyclic radical, nitroalkyl, $-NO_2$, $-CN$, $-NR^9C(O)-(C_1$-$C_{10}$ alkyl), $-C(O)-(C_1$-$C_{10}$ alkyl), $C_2$-$C_{10}$ alkthioalkyl, $-C(O)O-(C_1$-$C_{10}$ alkyl), $-OH$, $-SO_2$, $=S$, $-COOH$, $-NR^9_2$, carbonyl, $-C(O)-(C_1$-$C_{10}$ alkyl)-$CF_3$, $-C(O)-CF_3$, $-C(O)NR^9_2$, $-(C_1$-$C_{10}$ aryl)-S$-(C_6$-$C_{10}$ aryl), $-C(O)-(C_6$-$C_{10}$ aryl), $-(CH_2)_m-O-(CH_2)_m-O-(C_1$-$C_{10}$ alkyl) wherein each m is from 1 to 8, $-C(O)NR^9_2$, $-C(S)NR^9_2$, $-SO_2NR^9_2$, $-NR^9C(O)NR^9_2$, $-NR^9C(S)NR^9_2$, salts thereof, and the like. Each $R^9$ group in the preceding list independently includes, but is not limited to, H, alkyl or substituted alkyl, aryl or substituted aryl, or alkylaryl. Where substituent groups are specified by their conventional chemical formulas, written from left to right, they equally encompass the chemically identical substituents that would result from writing the structure from right to left, for example, $-CH_2O-$ is equivalent to $-OCH_2-$.

The term "polymer backbone" refers to the main chain of a linear or branched polymer.

The term "water-soluble polymer backbone" refers to a polymer backbone having water-solubility or dispersibility in water at ambient temperatures and a pH of about 7. For instance, a polyethylene glycol backbone is considered to be water-soluble if the corresponding polyethylene glycol can be solubilized or dispersed in water at ambient temperatures and a pH of about 7.

The term "nucleotidic polymer" refers to a single- or double-stranded polymer chain composed of two or more nucleic acids. The term "nucleic acid" refers to deoxyribonucleotides or ribonucleotides. By way of example only, such nucleic acids and nucleic acid polymers include, but are not limited to, (i) analogues of natural nucleotides which have similar binding properties as a reference nucleic acid and are metabolized in a manner similar to naturally occurring nucleotides; (ii) oligonucleotide analogs including, but are not limited to, PNA (peptidonucleic acid), analogs of DNA used in antisense technology (phosphorothioates, phosphoroamidites, and the like); (iii) conservatively modified variants thereof (including but not limited to, degenerate codon substitutions) and complementary sequences.

The term "peptidic polymer" refers to a polymer of two or more amino acid residues. The term applies to naturally occurring amino acid polymers as well as amino acid polymers in which one or more amino acid residues is a non-natural amino acid.

As used herein, a "biologically active molecule" includes any molecule which can have a biological effect. Examples of biologically active molecules include therapeutic agents, small molecules, oligo- and polypeptides, oligonucleotides, coding DNA sequences, antisense DNA sequences, mRNAs, antisense RNA sequences, RNAis, and siRNAs, carbohydrates, lipids, growth factors, enzymes, transcription factors, toxins, antigenic peptides (as for vaccines), antibodies, and antibody fragments.

The term "group reactive with a biologically active molecule" refers to a functional group that can be covalently bound to a functional group of a biologically active molecule.

The terms "protecting group" and "protective group" refer to a moiety that reversibly chemically modifies a functional group in order to obtain chemoselectivity or in order to reduce degradation in one or more subsequent chemical reactions. Suitable protecting groups are well known in the art (see, e.g., Greene and Wuts, *Protective Groups in Organic Synthesis*, 3rd Ed., John Wiley & Sons, New York, N.Y., 1999, which is incorporated herein by reference in its entirety).

The term "detectable functional group" refers a functional group that physically or chemically interacts with its environment to produce a signal or product that can be detected by analytical and/or imaging methods such as visible, UV-, IR-, NIR-light, X-Ray, and NMR-based imaging methods, enzymatic assays, and UV-, IR-, NMR-, X-ray-, and mass spectrometry-based analytics.

As used herein, a "fluorophore" is a chemical group that can be excited by light to emit fluorescence. Some suitable fluorophores may be excited by light to emit phosphorescence. As used herein, a "dye" may include a fluorophore. Non-limiting examples of a fluorophore include: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMIA (5-Carboxytetranethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy F1-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18 (3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; Eukolight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 1OGF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, WV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag- Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3. As used herein, a "fluorophore" may include a salt of the fluorophore.

Fluorophores may include derivatives that have been modified to facilitate conjugation to another reactive molecule. As such, fluorophores may include amine-reactive derivatives such as isothiocyanate derivatives and/or succinimidyl ester derivatives of the fluorophore.

The term "hydrophobic separation handle" refers to a moiety that when attached to or part of a compound reduces the hydrophilicity of that compound, i.e. reduces its tendency to be solved or dispersed in water. The term "separation handle" refers to a moiety that when attached to or part of a compound alters the mobility of that compound in a chromatographic method such that its separation from contaminants is improved. Alternatively, the term "separation handle" refers to a moiety that when attached to or part of a compound improves the yield of the compound in a chromatographic method in comparison to a hydrogen substituent.

The term "hydrophobicity" refers to the relative degree with which a compound or moiety is solved or dispersed in a non-aqueous solvent such as n-octanol. The degree of hydrophobicity or hydrophilicity of a compound or moiety can be measured using methods known in the art, such as, reversed phase chromatography and other chromatographic methods, partitioning, accessible surface area methods, and measurement of physical properties such as partial molar heat capacity, transition temperature and surface tension.

The term "activating group" refers to a moiety that increases the capability of the group reactive with a biologically active molecule to form a covalent bond with a biologically active molecule. Usually these groups increase or decrease the electronegativity of a selected moiety so it becomes more nucleophilic or more electrophilic. Non-limiting examples of an activating group include: lower alkylamino, diloweralkylamino, amino, halo, aryl, lower alkoxy, lower aralkoxy, aryloxy, mercapto, lower alkylthio, nitro, monophaloalkyl, dihaloalkyl, trihaloalkyl (e.g., $CF_3$), halo, formyl, lower alkanoyl, lower alkylsulfonyl, lower alkylsulfinyl, and the like.

The term "essentially pure" refers to chemical purity of a compound provided herein that may be substantially or essentially free of other components which normally accompany or interact with the compound prior to purification. By way of example only, a compound may be "essentially pure" when the preparation of the compound contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, an "essentially pure" compound may have a purity level of about 70%, about 75%, about 80%, about 85%, about 90%, about 95%, about 96%, about 97%, about 98%, about 99% or greater. For the purposes of this document, preparations of functionalized polymers or conjugates differing only in the length of their polymer chain are considered to be essentially pure. By way of example a preparation of a mono-functionalized compound may be "essentially pure" when the preparation contains less than about 30%, less than about 25%, less than about 20%, less than about 15%, less than about 10%, less than about 5%, less than about 4%, less than about 3%, less than about 2%, or less than about 1% (by dry weight) of contaminating unfunctionalized and/or poly-functionalized polymers. An essentially pure compound may be obtained using chromatographic purification methods.

The term "protic solvent" is used herein to refer to solvents which comprise dissociable hydrogen ions. Examples of protic solvents include alcohols, such as ethanol, and methanol.

The phrase "pharmaceutically acceptable" is used herein to refer to those inhibitors, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Some of the compounds provided herein are acidic and may form a salt with a pharmaceutically acceptable cation. Some of the compounds herein can be basic and accordingly, may form a salt with a pharmaceutically acceptable anion. All such salts, including di-salts are within the scope of the compositions described herein and they can be prepared by conventional methods. For example, salts can be prepared by contacting the acidic and basic entities, in either an aqueous, non-aqueous or partially aqueous medium. The salts are recovered by using at least one of the following techniques: filtration, precipitation with a non-solvent followed by filtration, evaporation of the solvent, or, in the case of aqueous solutions, lyophilization.

Salts, for example, include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

Compounds

The following compounds are suitable for conjugating to a biologically active molecule or a derivative thereof.

Compounds of Formula (1)

Provided herein is a compound comprising a water-soluble, non-nucleotidic and non-peptidic polymer backbone having at least one terminus covalently bonded to a structure of formula (1):

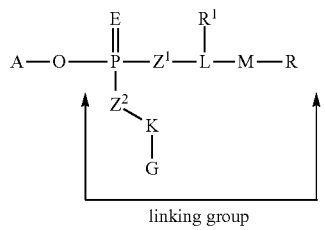

linking group or pharmaceutical salt thereof wherein: A is the point of bonding to a terminus of the polymer backbone, E is an oxygen or sulfur atom, K is selected from the group consisting of alkylene, alkyleneoxyalkylene, or an oligomeric form of alkyleneoxyalkylene, G is selected from the group consisting of hydrogen, an alkoxy, or a hydrophobic separation handle, $Z^1$ and $Z^2$ can be oxygen or nitrogen, in such way that both $Z^1$ and $Z^2$ may be oxygen, but when $Z^1$ is NH then $Z^2$ is oxygen, and when $Z^2$ is NH then $Z^1$ is oxygen, L is selected from the group consisting of a divalent radical of a nucleoside, linear alkylene, branched alkylene, alkyleneoxyalkylene, oligomeric form of alkyleneoxyalkylene, arylene, and substituted arylene, M is a protected group that when deprotected is reactive with a biologically active molecule or a derivative thereof, a group reactive with a biologically active molecule or a derivative thereof, or detectable functional group, R is a protecting group, activating group, hydrogen or absent.

A polymer backbone, as provided herein, can be branched or linear. For example, a polymer backbone can have from 2 to 100 termini (e.g., 2 to 80, 2 to 75, 2 to 60, 2 to 50, 2 to 40, 2 to 35, 2 to 25, 2 to 10, 2 to 5, 4 to 20, 5 to 25, 10 to 50, 25 to 75, 3 to 6, 5 to 15 termini). In some embodiments, a polymer is linear and therefore has 2 termini. In some embodiments, only one termini of a polymer backbone is covalently bonded to the structure of formula (1). In some embodiments, wherein a polymer has two termini, both termini of the polymer backbone are covalently bonded to the structure of formula (1).

A polymer backbone can be, for example, poly(alkylene glycol), poly(oxyethylated polyol), poly(olefinic alcohol), poly(α-hydroxy acid), poly(vinyl alcohol), polyoxazoline, or a copolymer thereof. A polyalkylene glycol includes linear or branched polymeric polyether polyols. Such polyalkylene glycols, include, but are not limited to, polyethylene glycol, polypropylene glycol, polybutylene glycol, and derivatives thereof. Other exemplary embodiments are listed, for example, in commercial supplier catalogs, such as Shearwater Corporation's catalog "Polyethylene Glycol and Derivatives for Biomedical Applications" (2001). By way of example only, such polymeric polyether polyols have average molecular weights between about 0.1 kDa to about 100 kDa. By way of example, such polymeric polyether polyols include, but are not limited to, between about 500 Da and about 100,000 Da or more. The molecular weight of the polymer may be between about 500 Da and about 100,000 Da. For example, a polymer used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, and 500 Da. In some embodiments, the molecular weight of the polymer is between about 500 Da and about 50,000 Da. In some embodiments, the molecular weight of the polymer is between about 500 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

In some embodiments, a polymer backbone is a linear or branched poly(ethylene glycol).

In some embodiments, the poly(ethylene glycol) molecule is a linear polymer. The molecular weight of the linear chain PEG may be between about 1,000 Da and about 100,000 Da. For example, a linear chain PEG used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the linear chain PEG is between about 1,000 Da and about 50,000 Da. In some embodiments, the molecular weight of the linear chain PEG is between about 1,000 Da and about 40,000 Da. In some embodiments, the molecular weight of the linear chain PEG is between about 5,000 Da and about 40,000 Da. In some embodiments, the molecular weight of the linear chain PEG is between about 5,000 Da and about 20,000 Da.

In some embodiments, the poly(ethylene glycol) molecule is a branched polymer. The molecular weight of the branched chain PEG may be between about 1,000 Da and about 100,000 Da. For example, a branched chain PEG used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da.

In some embodiments, E is oxygen. In some embodiments, E is sulfur.

In some embodiments, K is a linear or branched alkylene. For example, K can be selected from the group consisting of: methylene, ethylene, propylene, isopropylene, butylene, isobutylene, sec-butylene, tert-butylene, and hexylene. In some embodiments, K can be an alkyleneoxyalkylene or an oligomeric alkyleneoxyalkylene. For example, K can be a residue from diethylene glycol, triethylene glycol, tetraethylene glycol, or hexaethylene glycol. In some embodiments, K is selected from the group consisting of —$(CH_2)_n$— and —$((CH_2)_n$—O—$(CH_2)_m)_p$—, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In some embodiments, G is a hydrophobic separation handle. For example, G can be a substituted or unsubstituted trityloxy group. In some embodiments, G is selected from the group consisting of monoalkoxy substituted trityloxy group or dialkoxy substituted trityloxy group.

In some embodiments, one of $Z^1$ and $Z^2$ is NH and the other is O. For example, $Z^1$ is O and $Z^2$ is NH; $Z^1$ is NH and $Z^2$ is O. In some embodiments, both $Z^1$ and $Z^2$ are O.

In some embodiments, L is a linear or branched alkylene. For example, L can be selected from the group consisting of: methylene, ethylene, propylene, isopropylene, butylene, isobutylene, sec-butylene, tert-butylene, and hexylene. In some embodiments, L can be an alkyleneoxyalkylene or an oligomeric alkyleneoxyalkylene. For example, L can be a residue from diethylene glycol, triethylene glycol, tetraethylene glycol or hexaethylene glycol. In some embodiments, L is selected from the group consisting of —$(CH_2)_n$— and —$((CH_2)_n$—O—$(CH_2)_m)_p$—, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In some embodiments, L is a substituted or unsubstituted arylene. For example, L can be a structure with the formula:

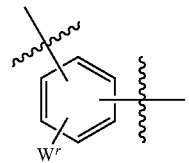

where W is a substituent and r is an integer from 0 to 4. For example, W can be selected from the group consisting of: halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, substituted phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —$NR^9C(O)$—($C_1$-$C_{10}$ alkyl), —$C(O)$—($C_1$-$C_{10}$ alkyl), $C_2$-$C_{10}$ alkthioalkyl, —$C(O)O$—($C_1$-$C_{10}$ alkyl), —OH, —$SO_2$, =S, —COOH, —$NR^9_2$, carbonyl, —$C(O)$—($C_1$-$C_{10}$ alkyl)-$CF_3$, —$C(O)$—$CF_3$, —$C(O)NR^9_2$, —($C_1$-$C_{10}$ aryl)-S—($C_6$-$C_{10}$ aryl), —$C(O)$—($C_6$-$C_{10}$ aryl), —$(CH_2)_m$—O—$(CH_2)_m$—O—($C_1$-$C_{10}$ alkyl) wherein each m is from 1 to 8, —$C(O)NR^9_2$, —$C(S)NR^9_2$, —$SO_2NR^9_2$, —$NR^9C(O)NR^9_2$, —$NR^9C(S)NR^9_2$, salts thereof, and the like. Each $R^9$ group in the preceding list independently includes, but is not limited to, H, alkyl or substituted alkyl, aryl or substituted aryl, or alkylaryl. In some embodiments, W is $R^1$ as described above.

Non-limiting examples of L include:

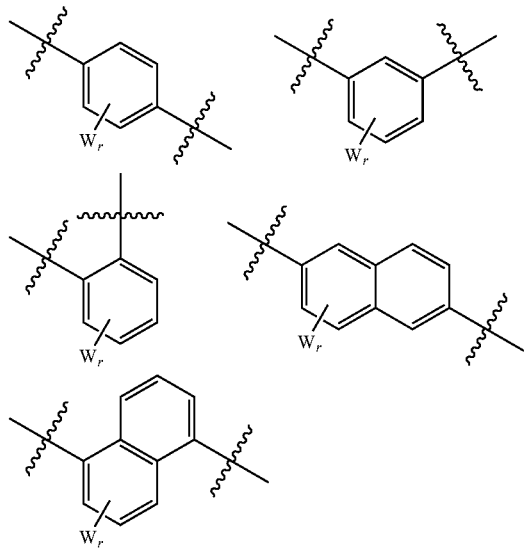

In some cases, L can also be a divalent radical of a nucleoside. For example, L can be a divalent radical of a natural nucleoside, such as adenosine, deoxyadenosine, guanosine, deoxyguanosine, 5-methyluridine, thymidine, uridine, deoxyuridine, cytidine, and deoxycytidine.

M is a group reactive with a biologically active molecule or a derivative thereof and can be selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, and iodoacetamide. In some embodiments, the group is protected or further reacted with a group R as shown in the structure of formula (1). The point of attachment of such a group is well understood by those of skill in the art.

In some embodiments, R is absent. In some embodiments, R is a protecting group. For this purpose, R may include any suitable protecting group based on the group to be protected. For example, R may include any suitable hydroxyl functional group including, but not limited to, ether, ester, carbonate, or sulfonate protecting groups.

In particular, the ether protecting group may include benzyloxymethyl (BOM), methylthiomethyl (MTM), phenylthiomethyl (PTM), cyanoethyl, 2,2-dichloro-1,1-difluoroethyl, 2-chloroethyl, 2-bromoethyl, tetrahydropyranyl (THP), phenacyl, 4-bromophenacyl, allyl, propargyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylemethyl, 4-picolyl, heptafluoro-p-tolyl, tetrafluoro-4-pyridyl, trimethylsilyl (TMS), and protecting groups.

The ester protecting group may include acetoxy (OAc), aryl formate, acetate, levulinate, pivaloate, benzoate, and 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC-OAr), 4-methylsulfinylbenzyl carbonate (Msz-OAr), 2,4-dimethylpent-3-yl carbonate (Doc-OAr), aryl 2,2,2-trichloroethyl carbonate.

The sulfonate protecting groups may include aryl methanesulfonate, aryl toluenesulfonate, and aryl 2-formylbenzenesulfonate.

In some embodiments, R may include any suitable amino protecting group, including, but not limited to, carbamate, amide, N-alkyl, or N-aryl-derived protecting groups.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzol[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)] methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N,N-dicycloheylcarboxamido)ethyl carbamate, 1-adamanyl carbamate (1-Adoc), cinyl carbamate (Voc), 1-isopropylallyl carbamate (Ipaoc), 4-nicrocinnamyl carbamate (Noc), 3-(3'pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methyl sulfinylbenzyl carbamate (Msz), diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In some embodiments, the carbamate protecting group is chosen from 9-fluorenylmethyl carbamate (Fmoc), t-butyl carbamate (Boc), and carboxybenzyl carbamate (cbz).

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide.

Examples of suitable protecting groups also include tert-butyl, benzyl, 4-methoxybenzyl, benzyloxymethyl, phenacyl, allyl, trimethylsilyl, benzyloxycarbonyl, tert-butoxycarbonyl, and acetal and ketal derivatives. In some embodiments, R is selected from trityls, substituted trityls (e.g., monomethoxytrityl (MMTr), dimethoxytrityl (DMTr), trimethoxytrityl (TMTr), 2-chlorotrityl (ClTr) and p-bromophenacyloxytrityl (BPTr), pixyls and substituted pixyls (see, for example, U.S. Publication No. 2007/0276139). In some embodiments, R is selected from trityl, monoalkoxytrityl, dialkoxytrityl, pixyl, alkoxypixyl, fluorenylmethyloxycarbonyl, trifluoroacetyl, acetal, and cyclic acetal.

In some embodiments, $R^1$ is a hydrophobic separation handle.

A hydrophobic separation handle is as described herein. In some embodiments, the hydrophobic separation handle is also a protecting group as described herein. In some embodiments, at least one of R, $R^1$, and G is a hydrophobic separation handle. For example, only one of R, $R^1$, and G is a hydrophobic separation handle.

In some embodiments, only one of $R^1$, R and G is a hydrophobic separation handle (e.g., a trityl group) as provided herein. For example, if R is a hydrophobic separation handle, then $R^1$ is absent and G is hydrogen or an alkoxy. In some embodiments, R is absent or a protecting group, $R^1$ is a hydrophobic separation handle, and G is hydrogen or an alkoxy. In some embodiments, wherein more than one of R, $R^1$ and G is a hydrophobic separation handle, one of R, $R^1$ and G is more hydrophobic than the others (e.g., substantially more hydrophobic). In some embodiments, the hydrophobic separation handle is a substituted or unsubstituted trityl or trityloxy group. For example, only one of R, $R^1$ and G is a substituted or unsubstituted trityl or trityloxy group.

A compound as described above can be prepared, for example, by contacting a water-soluble, non-peptidic and non-nucleotidic polymer, in a water-free solvent (e.g., an organic solvent), with a reagent of formula (4):

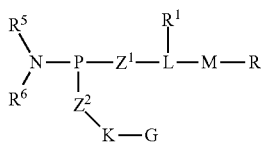

wherein:

$R^5$ and $R^6$ independently from each other represent $C_1$-$C_6$-alkyl or $R^5$ and $R^6$ jointly form a 5- or 6-membered ring with the N to which they are bonded. In some embodiments, $R^5$ and $R^6$ are independently a $C_1$-$C_6$-alkyl. For example, $R^5$ and $R^6$ can be independently selected from the group consisting of methyl, ethyl, propyl, isopropyl, butyl, isobutyl, sec-butyl, tert-butyl, and hexyl. In some embodiments, $R^5$ and $R^6$ are isopropyl. In some embodiments, $R^5$ and $R^6$ can jointly form a 5- or 6-membered ring with the N to which they are bonded. For example, $R^5$ and $R^6$ jointly form a pyrrolidine, pyrroline, imidazoline, pyrazolidine, piperidine, 1,2,3,6-tetrahydropyridine, 1,4-dihydropyridine, piperazine, morpholine, thiomorpholine, pyridyl, pyrazinyl, pyrimidinyl, particularly 2- and 4-pyrimidinyl, pyridazinyl, pyrrolyl, particularly 2-pyrrolyl, imidazolyl, thiazolyl, oxazolyl, or pyrazolyl, particularly 3- and 5-pyrazolyl. In some embodiments, $R^5$ and $R^6$ can jointly form a morpholine ring.

The ratio of a polymer to a reagent of formula (4) can range from about 1:10 to about 10:1 (e.g., about 2:1, about 3:1, about 4:1, about 5:1, about 6:1, about 7:1, about 8:1, about 9:1, about 1:2, about 1:3, about 1:4, about 1:5, about 1:6, about 1:7, about 1:81 about 1:9, about 2:8, about 3:7, about 4:6 about 5:10, and about 4:8). In some embodiments, the ratio of a polymer to a reagent of formula (4) is from about 1:1 to about 1:10, for example, about 2:1.

An activating reagent can then be added to the mixture of the polymer and the reagent of formula (4). An activating reagent can be any group suitable to initiate coupling of the polymer and the reagent of formula (4). Suitable activating reagents include, for example, 1H-tetrazole, 5-(ethylthio)-1H-tetrazole (ETT), 5-(benzylthio)-1H-tetrazole (BTT), Activator 42 (5-(3,5-bis(trifluoromethyl)phenyl)-1H-tetrazole), 2-ethylthiotetrazole, 2-bezylthiotetrazole, 4,5-dicyanoimidazole and 4,5-dicyanoimidazole (DCI). In some embodiments, an activating agent can be selected from pyridinium hydrochloride, pyridinium trifluoroacetage, and buffered carboxylic acids.

An oxidizing agent can then be added to oxidize $P^{+3}$ to $P^{-5}$. Suitable oxidizing agents and conditions can be readily determined by those of ordinary skill in the art. For example, an oxidant such as $RuO_4^-$/NMO, Dess-Martin's reagent, DMSO/triflic anhydride, PDC, hydrogen peroxide, inorganic peroxides, nitric acid, nitrates, chlorite, chlorate, perchlorate, hypochlorite, peroxides, iodine, ozone, nitrous oxide, silver oxide, permanganate salts, hexavalent chromium compounds, chromic acid, dichromic acids, chromium trioxide, pyridinium chlorochromate, persulfuric acid, sulfoxides, sulfuric acid, Tollens' reagent, 2,2'-dipyridiyldisulfide (DPS), and osmium tetroxide may be used.

In some embodiments, iodine can be used as an oxidizing agent. For example, a solution of iodine can be used and prepared by dissolving iodine in a mixture of pyridine, tetrahydrofuran and water. Elemental sulfur can be used for phosphite oxidation combined with formation of sulfurized product. In some embodiments, other more soluble and more reactive reagents, such as 3H-1,2-benzothiazol-3-one 1,1-dioxide (Beaucage reagent), phenylacetyl disulfide (PADS), or dimethylthiuram (DTD) can be used. Alternatively, peroxides exemplified by t-butyl hydrogen peroxide or m-chlorobenzoyl peroxide may be used for $P^{+3}$ to $P^{+5}$ oxidations.

In some embodiments, an oxidizing reagent is selected from a group consisting of: iodine, hydrogen peroxide, t-butyl hydrogen peroxide, acetone peroxide, sulfur, and thiuram disulfide.

In some embodiments, R is a protecting group or a hydrophobic separation handle and the method can include purifying the compound using chromatography (e.g., reverse phase chromatography). In some embodiments, the method also includes removing the protecting group.

For the methods provided above, the deprotection may involve, for example, either sequential or one-pot deprotection of certain protecting groups. Suitable reagents and conditions for the deprotection can be readily determined by those of ordinary skill in the art. For example, deprotection may be achieved upon treatment of the protected compound under conditions so that hydroxyl protecting groups, such as acetate, isopropylidine, benzylidine, trityl, and/or pixyl protecting groups, are removed from the protected compound. The acetate group can be cleaved under mild conditions, for example, by diluted solution of ammonia or by solution of potassium carbonate. The benzylidene and isopropylidene groups can be cleaved by hydrogenation or using acidic hydrolysis as described elsewhere by R. M. Hann et al., *J. Am. Chem. Soc.*, 72, 561 (1950). In yet another example, the deprotection can be performed so that amino protecting groups, such as 9-fluorenylmethyl carbamate (Fmoc), t-butyl carbamate (Boc), and carboxybenzyl carbamate (cbz) protecting groups are cleaved from the protected compound. 9-fluorenylmethyl carbamate (FMOC) can be removed under mild conditions with an amine base (e.g., piperidine) to afford the free amine and dibenzofulvene, as described by E. Atherton et al., "*The Fluorenylmethoxycarbonyl Amino Protecting Group*," in The Peptides, S. Udenfriend and J. Meienhofer, Academic Press, New York, 1987, p. 1. t-butyl carbamate (Boc) can be removed, as reported by G. L. Stahl et al., *J. Org. Chem.*, 43, 2285 (1978), under acidic conditions (e.g., 3 M HCl in EtOAc). Hydrogenation can be used to cleave the carboxybenzyl carbamate (cbz) protecting group as described by J. Meienhofer et al., *Tetrahedron Lett.*, 29, 2983 (1988).

In some embodiments, deprotection may be performed under anaerobic conditions. The deprotection may also be performed at ambient temperature or at temperatures of from about 20-60° C. (e.g., 25, 30, 35, 40, 45, 50, or 55° C.).

In some cases, a compound as described above can be further purified using precipitation and/or crystallization.

Compounds of Formula (2)

Also provided herein are compounds of formula (2):

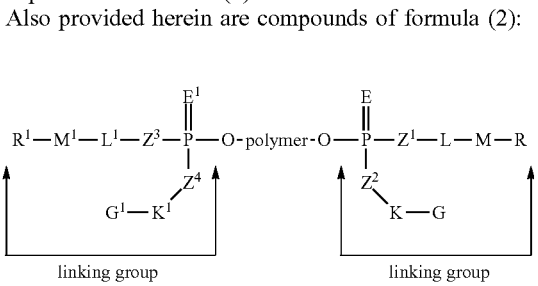

or a salt form thereof,
wherein:
polymer is a linear, water-soluble, non-peptidic, and non-nucleotidic polymer backbone, wherein each linking group is bonded at a different terminus of said polymer;
E and $E^1$ are independently O or S;

K and $K_1$ are independently selected from the group consisting of: alkylene, alkyleneoxyalkylene, and oligomeric alkyleneoxyalkylene;

G and $G_1$ are independently absent or are selected from the group consisting of: alkoxy and a hydrophobic separation handle;

each pair of $Z^1$ and $Z^2$ and $Z^3$ and $Z^4$ are independently selected from O and NH, wherein only one of each pair of $Z^1$ and $Z^2$ and $Z^3$ and $Z^4$ can be NH;

L and $L^1$ are independently selected from the group consisting of: a divalent radical of a nucleoside, alkylene, alkyleneoxyalkylene, oligomeric alkyleneoxyalkylene, and unsubstituted and substituted arylene;

M and $M^1$ are independently selected from a protected group that when deprotected is reactive with a biologically active molecule or a derivative thereof, a group reactive with a biologically active molecule or a derivative thereof, or is a detectable functional group, wherein M and $M^1$ are different, and wherein at least one of M and M1 is a protected group that when deprotected is reactive with a biologically active molecule or a derivative thereof or a group reactive with a biologically active molecule or a derivative thereof; and R and $R^1$ are independently absent, hydrogen, a protecting group, or an activating group;

wherein when M is a protected group that when deprotected is reactive with a biologically active molecule or a derivative thereof, then R is a protecting group or a hydrophobic separation handle;

wherein when M is a group reactive with a biologically active molecule or a derivative thereof, R is absent, hydrogen, or an activating group;

wherein when M is a detectable functional group, R is absent or hydrogen;

wherein when $M^1$ is a protected group that when deprotected is reactive with a biologically active molecule or a derivative thereof, then $R^1$ is a protecting group or a hydrophobic separation handle;

wherein when $M^1$ is a group reactive with a biologically active molecule or a derivative thereof, $R^1$ is absent, hydrogen, or an activating group; and wherein when $M^1$ is a detectable functional group, $R^1$ is absent or hydrogen.

A polymer can be, for example, poly(alkylene glycol), poly(oxyethylated polyol), poly(olefinic alcohol), poly($\alpha$-hydroxy acid), poly(vinyl alcohol), polyoxazoline, or a copolymer thereof. Such polyalkylene glycols, include, but are not limited to, polyethylene glycol, polypropylene glycol, polybutylene glycol, and derivatives thereof. Other exemplary embodiments are listed, for example, in commercial supplier catalogs, such as Shearwater Corporation's catalog "Polyethylene Glycol and Derivatives for Biomedical Applications" (2001). By way of example only, such polymeric polyether polyols have average molecular weights between about 0.1 kDa to about 100 kDa. By way of example, such polymeric polyether polyols include, but are not limited to, between about 500 Da and about 100,000 Da or more. The molecular weight of the polymer may be between about 500 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, and 500 Da. In some embodiments, the molecular weight of the polymer is between about 500 Da and about 50,000 Da. In some embodiments, the molecular weight of the polymer is between about 500 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

In some embodiments, the polymer is a poly(ethylene glycol) polymer. The molecular weight of the PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the PEG is between about 1,000 Da and about 50,000 Da. In some embodiments, the molecular weight of the n PEG is between about 1,000 Da and about 40,000 Da. In some embodiments, the molecular weight of the PEG is between about 5,000 Da and about 40,000 Da. In some embodiments, the molecular weight of the PEG is between about 5,000 Da and about 20,000 Da.

In some embodiments, $E^1$ is oxygen. In some embodiments, $E^1$ is sulfur. In some embodiments, $E^2$ is oxygen. In some embodiments, $E^2$ is sulfur. In some embodiments, both of $E^1$ and $E^2$ are oxygen.

In some embodiments, K and $K^1$ are independently selected from a linear or branched alkylene. For example, K and $K^1$ can be independently selected from the group consisting of: methylene, ethylene, propylene, isopropylene, butylene, isobutylene, sec-butylene, tert-butylene, and hexylene. In some embodiments, K and $K^1$ are independently an alkyleneoxyalkylene or an oligomeric alkyleneoxyalkylene. For example, K and $K^1$ can be independently a residue from diethylene glycol, triethylene glycol, tetraethylene glycol or hexaethylene glycol. In some embodiments, K and $K^1$ are independently selected from the group consisting of —$(CH_2)_n$— and —$((CH_2)_n$—O—$(CH_2)_m)_p$—, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In some embodiments, G and $G^1$ are independently a hydrophobic separation handle. For example, G and $G^1$ are independently a substituted or unsubstituted trityloxy group. In some embodiments, G and $G^1$ are independently selected from the group consisting of monoalkoxy substituted trityloxy group or dialkoxy substituted trityloxy group.

In some embodiments, one of $Z^1$ and $Z^2$ is NH and the other is O. For example, $Z^1$ is O and $Z^2$ is NH; $Z^1$ is NH and $Z^2$ is O. In some embodiments, both $Z^1$ and $Z^2$ are O. In some embodiments, one of $Z^1$ and $Z^2$ is NH and the other is O. For example, $Z^3$ is O and $Z^4$ is NH; $Z^3$ is NH and $Z^4$ is O. In some embodiments, both $Z^3$ and $Z^4$ are O. In some embodiments, one of $Z^1$ and $Z^2$ and $Z^3$ and $Z^4$ is NH and the other is O. For example, $Z^1$ and $Z^3$ are O and $Z^2$ and $Z^4$ are NH; $Z^1$ and $Z^3$ are NH and $Z^2$ and $Z^4$ O. In some embodiments, $Z^1$ and $Z^3$ are O and $Z^2$ and $Z^4$ are O.

In some embodiments, L and $L^1$ are independently selected from a linear or branched alkyl. For example, L and $L^1$ can be independently selected from the group consisting of: methylene, ethylene, propylene, isopropylene, butylene, isobutylene, sec-butylene, tert-butylene, and hexylene. In some embodiments, L and $L^1$ are independently an alkyleneoxyalkylene or an oligomeric alkyleneoxyalkylene. For example, L and $L^1$ can be independently a residue from diethylene glycol, triethylene glycol, tetraethylene glycol or hexaethylene glycol. In some embodiments, L and $L^1$ are independently selected from the group consisting of —$(CH_2)_n$— and —$((CH_2)_n$—O—$(CH_2)_m)_p$—, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In some embodiments, L and $L^1$ are independently a substituted or unsubstituted arylene. For example, L and $L^1$ can be independently a structure with the formula:

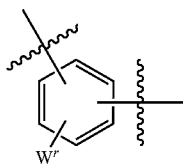

wherein W is a substituent and r is an integer from 0 to 4. For example, W can be selected from the group consisting of: halo, $C_1$-$C_{10}$ alkyl, $C_2$-$C_{10}$ alkenyl, $C_2$-$C_{10}$ alkynyl, alkoxy, $C_5$-$C_{12}$ aralkyl, $C_3$-$C_{12}$ cycloalkyl, $C_4$-$C_{12}$ cycloalkenyl, phenyl, substituted phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—$(C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —$NR^9C(O)$—$(C_1$-$C_{10}$ alkyl), —C(O)—$(C_1$-$C_{10}$ alkyl), $C_2$-$C_{10}$ alkthioalkyl, —C(O)O—$(C_1$-$C_{10}$ alkyl), —OH, —$SO_2$, =S, —COOH, —$NR^9_2$, carbonyl, —C(O)—$(C_1$-$C_{10}$ alkyl)-$CF_3$, —C(O)—$CF_3$, —C(O)$NR^9_2$, —$(C_1$-$C_{10}$ aryl)-S—$(C_6$-$C_{10}$ aryl), —C(O)—$(C_6$-$C_{10}$ aryl), —$(CH_2)_m$—O—$(CH_2)_m$—O—$(C_1$-$C_{10}$ alkyl) wherein each m is from 1 to 8, —C(O)$NR^9_2$, —C(S)$NR^9_2$, —$SO_2NR^9_2$, —$NR^9C(O)NR^9_2$, —$NR^9C(S)NR^9_2$, salts thereof, and the like. Each $R^9$ group in the preceding list independently includes, but is not limited to, H, alkyl or substituted alkyl, aryl or substituted aryl, or alkylaryl. In some embodiments, W is $R^1$ as described above.

Non-limiting examples of L and $L^1$ include:

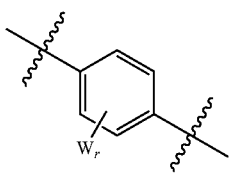 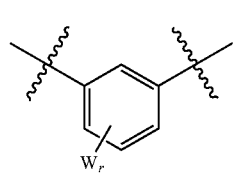

-continued

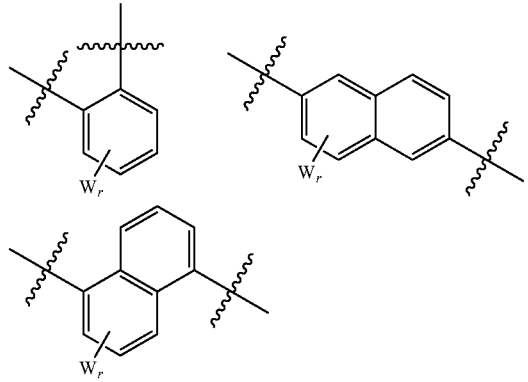

L and $L^1$ can also independently be a divalent radical of a nucleoside. For example, L and $L^1$ can be a divalent radical of a natural nucleoside, such as adenosine, deoxyadenosine, guanosine, deoxyguanosine, 5-methyluridine, thymidine, uridine, deoxyuridine, cytidine, and deoxycytidine.

M is a group reactive with a biologically active molecule or a derivative thereof and can be selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, and iodoacetamide. In some embodiments, the group is protected or further reacted with a group R and $R^1$ as shown in the formula (2). The point of attachment of such a group is well understood by those of skill in the art.

In some embodiments, M or $M^1$ is a detectable functional group. A detectable functional group, as used herein, can be any chemical or substance which is used to provide a signal or contrast in imaging. The signal enhancing domain can be an organic molecule, metal ion, salt or chelate, particle (particularly iron particle), or labeled peptide, protein, polymer or liposome. For example, a detectable functional group can include one or more of a radionuclide, a paramagnetic metal, a fluorophore, a dye, and an enzyme substrate. In some embodiments, a detectable functional group is biotin or a fluorophore.

In some embodiments, the detectable functional group is a physiologically compatible metal chelate compound consisting of one or more cyclic or acyclic organic chelating agents complexed to one or more metal ions with atomic numbers 21-29, 42, 44, or 57-83.

For x-ray imaging, the detectable functional group may consist of iodinated organic molecules or chelates of heavy metal ions of atomic numbers 57 to 83. In some embodiments, the detectable functional group is $^{125}$I-IgG. Examples of suitable compounds are described in M. Sovak, ed., "Radiocontrast Agents," *Springer-Verlag*, pp. 23-125 (1984) and U.S. Pat. No. 4,647,447.

For ultrasound imaging, the detectable functional group can consist of gas-filled bubbles such as Albunex, Echovist, or Levovist, or particles or metal chelates where the metal ions have atomic numbers 21-29, 42, 44 or 57-83. Examples of suitable compounds are described in Tyler et al., *Ultrasonic Imaging*, 3, pp. 323-29 (1981) and D. P. Swanson, "Enhancement Agents for Ultrasound: Fundamentals," *Pharmaceuticals in Medical Imaging*, pp. 682-87. (1990).

For nuclear radiopharmaceutical imaging or radiotherapy, the detectable functional group can consist of a radioactive molecule. In some embodiments, the chelates of Tc, Re, Co, Cu, Au, Ag, Pb, Bi, In, and Ga can be used. In some embodiments, the chelates of Tc-99m can be used. Examples of suitable compounds are described in Rayudu GVS, *Radiotracers for Medical Applications*, I, pp. 201 and D. P. Swanson et al., ed., *Pharmaceuticals in Medical Imaging*, pp. 279-644 (1990).

For ultraviolet/visible/infrared light imaging, the detectable functional group can consist of any organic or inorganic dye or any metal chelate.

For MRI, the detectable functional group can consist of a metal-ligand complex of a paramagnetic form of a metal ion with atomic numbers 21-29, 42, 44, or 57-83. In some embodiments, the paramagnetic metal is chosen from: Gd(III), Fe(III), Mn(II and III), Cr(III), Cu(II), Dy(III), Tb(III), Ho(III), Er(III) and Eu(III). Many suitable chelating ligands for MRI agents are known in the art. These can also be used for metal chelates for other forms of biological imaging. For example, an imaging agent can include: Gadovist, Magnevist, Dotarem, Omniscan, and ProHance.

In some embodiments, R and/or $R^1$ is absent. In some embodiments, R and/or $R^1$ is a protecting group. For this purpose, R and/or $R^1$ may include any suitable protecting group based on the group to be protected. For example, R and/or $R^1$ may include any suitable hydroxyl functional group including, but not limited to, ether, ester, carbonate, or sulfonate protecting groups.

In particular, the ether protecting group may include benzyloxymethyl (BOM), methylthiomethyl (MTM), phenylthiomethyl (PTM), cyanoethyl, 2,2-dichloro-1,1-difluoroethyl, 2-chloroethyl, 2-bromoethyl, tetrahydropyranyl (THP), phenacyl, 4-bromophenacyl, allyl, propargyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylemethyl, 4-picolyl, heptafluoro-p-tolyl, tetrafluoro-4-pyridyl, trimethylsilyl (TMS), and protecting groups.

The ester protecting group may include acetoxy (OAc), aryl formate, acetate, levulinate, pivaloate, benzoate, and 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC-OAr), 4-methylsulfinylbenzyl carbonate (Msz-OAr), 2,4-dimethylpent-3-yl carbonate (Doc-OAr), aryl 2,2,2-trichloroethyl carbonate.

The sulfonate protecting groups may include aryl methanesulfonate, aryl toluenesulfonate, and aryl 2-formylbenzenesulfonate.

In some embodiments, R may include any suitable amino protecting group, including, but not limited to, carbamate, amide, N-alkyl, or N-aryl-derived protecting groups.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzol[a,c,g,i]fluorenylmethyl carbamate (Tbfmoc), 2-chloro-3-indenylmethyl carbamate (Climoc), 2,7-di-t-butyl[9-(10,10-dioxo-10,10,10-tetrahydrothioxanthyl)]methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N,N-dicycloheylcarboxamido)ethyl carbamate, 1-adamanyl carbamate (1-Adoc), cinyl carbamate (Voc), 1-isopropylallyl carbamate (Ipaoc), 4-nicrocinnamyl carbamate (Noc), 3-(3'pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methyl sulfinylbenzyl carbamate (Msz), diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In some embodiments, the carbamate protecting group is chosen from 9-fluorenylmethyl carbamate (Fmoc), t-butyl carbamate (Boc), and carboxybenzyl carbamate (cbz).

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide.

Examples of suitable protecting groups also include tert-butyl, benzyl, 4-methoxybenzyl, benzyloxymethyl, phenacyl, allyl, trimethylsilyl, benzyloxycarbonyl, tert-butoxycarbonyl, and acetal and ketal derivatives. In some embodiments, R is selected from trityls, substituted trityls (e.g., monomethoxytrityl (MMTr), dimethoxytrityl (DMTr), trimethoxytrityl (TMTr), 2-chlorotrityl (ClTr) and p-bromophenacyloxytrityl (BPTr), pixyls and substituted pixyls (see, for example, U.S. Publication No. 2007/0276139). In some embodiments, R is selected from trityl, monoalkoxytrityl, dialkoxytrityl, pixyl, alkoxypixyl, fluorenylmethyloxycarbonyl, trifluoroacetyl, acetal, and cyclic acetal.

In some embodiments, R and/or $R^1$ is a hydrophobic separation handle.

A hydrophobic separation handle is as described herein. In some embodiments, the hydrophobic separation handle is also a protecting group as described herein. In some embodiments, at least one of R, $R^1$, G, and $G^1$ is a hydrophobic separation handle.

In some embodiments, only one of R and G and $R^1$ and $G^1$ is a hydrophobic separation handle (e.g., a trityl group) as provided herein. For example, if R is a hydrophobic separation handle, then G is hydrogen or an alkoxy. Alternatively, if $R^1$ is a hydrophobic separation handle, then $G^1$ is absent or an alkoxy. In some embodiments, R is absent or a protecting group, $R^1$ is a hydrophobic separation handle, and G and $G^1$ are independently absent or an alkoxy, wherein $R^1$ is more hydrophobic than R. In some embodiments, $R^1$ is absent or a protecting group, R is a hydrophobic separation handle, and G and $G^1$ are independently absent or an alkoxy, wherein R is more hydrophobic than $R^1$. In some embodiments, the hydrophobic separation handle is a substituted or unsubstituted trityl or trityloxy group. For example, only one of R, $R^1$, G, and $G^1$ is a substituted or unsubstituted trityl or trityloxy group.

A compound as described above can be prepared, for example, by contacting a water-soluble, non-peptidic and non-nucleotidic polymer, in a water-free solvent (e.g., an organic solvent), with a reagent selected from formula (5):

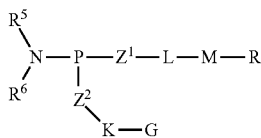

wherein:

$R^5$ and $R^6$ independently from each other represent $C_1$-$C_6$-alkyl or $R^5$ and $R^6$ jointly form a 5- or 6-membered ring with the N to which they are bonded, and formula (6):

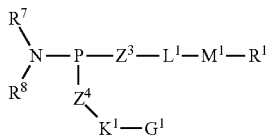

wherein:

$R^7$ and $R^8$ independently from each other represent $C_1$-$C_6$-alkyl or $R^7$ and $R^8$ jointly form a 5- or 6-membered ring with the N to which they are bonded;

under conditions that facilitate formation of monoderivatized product.

In some embodiments, $R^5$ and $R^6$ are independently a $C_1$-$C_6$-alkyl. For example, $R^5$ and $R^6$ can be independently selected from the group consisting of methyl, ethyl, propyl, isopropyl, butyl, isobutyl, sec-butyl, tert-butyl, and hexyl. In some embodiments, $R^5$ and $R^6$ are isopropyl. In some embodiments, $R^5$ and $R^6$ jointly form a 5- or 6-membered ring with the N to which they are bonded. For example, $R^5$ and $R^6$ jointly form a pyrrolidine, pyrroline, imidazoline, pyrazolidine, piperidine, 1,2,3,6-tetrahydropyridine, 1,4-dihydropyridine, piperazine, morpholine, thiomorpholine, pyridyl, pyrazinyl, pyrimidinyl, particularly 2- and 4-pyrimidinyl, pyridazinyl, pyrrolyl, particularly 2-pyrrolyl, imidazolyl, thiazolyl, oxazolyl, and pyrazolyl, particularly 3- and 5-pyrazolyl. In some embodiments, $R^5$ and $R^6$ jointly form a morpholine ring.

In some embodiments, $R^7$ and $R^8$ are independently a $C_1$-$C_6$-alkyl. For example, $R^7$ and $R^8$ can be independently selected from the group consisting of methyl, ethyl, propyl, isopropyl, butyl, isobutyl, sec-butyl, tert-butyl, and hexyl. In some embodiments, $R^7$ and $R^8$ are isopropyl. In some embodiments, $R^7$ and $R^8$ jointly form a 5- or 6-membered ring with the N to which they are bonded. For example, $R^7$ and $R^8$ jointly form a pyrrolidine, pyrroline, imidazoline, pyrazolidine, piperidine, 1,2,3,6-tetrahydropyridine, 1,4-dihydropyridine, piperazine, morpholine, thiomorpholine, pyridyl, pyrazinyl, pyrimidinyl, particularly 2- and 4-pyrimidinyl, pyridazinyl, pyrrolyl, particularly 2-pyrrolyl, imidazolyl, thiazolyl, oxazolyl, and pyrazolyl, particularly 3- and 5-pyrazolyl. In some embodiments, $R^7$ and $R^8$ jointly form a morpholine ring.

The ratio of a polymer to a reagent of formula (5) or (6) can range from about 1:10 to about 10:1 (e.g., about 2:1, about 3:1, about 4:1, about 5:1, about 6:1, about 7:1, about 8:1, about 9:1, about 1:2, about 1:3, about 1:4, about 1:5, about 1:6, about 1:7, about 1:81 about 1:9, about 2:8, about 3:7, about 4:6 about 5:10, and about 4:8). In some embodiments, the ratio of a polymer to a reagent of formula (5) or (6) is from about 1:1 to about 1:10. In some embodiments, the ratio of a polymer to a reagent of formula (5) or (6) is about 2:1.

In some embodiments, conditions that facilitate formation of a monoderivatized product include the addition of an activating reagent. An activating reagent is then added to the mixture of the polymer and the reagent of formula (4) or (5). An activating reagent can be any group suitable to initiate coupling of the polymer and the reagent of formula (4). Suitable activating reagents include, for example, 1H-tetrazole, 5-(ethylthio)-1H-tetrazole (ETT), 5-(benzylthio)-1H-tetrazole (BTT), Activator 42 (5-(3,5-bis(trifluoromethyl)phenyl)-1H-tetrazole), 2-ethylthiotetrazole, 2-bezylthiotetrazole, 4,5-dicyanoimidazoleand 4,5-dicyanoimidazole (DCI). In some embodiments, an activating agent can be selected from pyridinium hydrochloride, pyridinium trifluoroacetage, and buffered carboxylic acids.

In some embodiments, conditions that facilitate formation of a monoderivatized product include addition of an oxidizing agent to oxidize $P^{+3}$ to $P^{+5}$. Suitable oxidizing agents and conditions can be readily determined by those of ordinary skill in the art. For example, an oxidant such as $RuO_4^-$/NMO, Dess-Martin's reagent, DMSO/triflic anhydride, PDC, hydrogen peroxide, inorganic peroxides, nitric acid, nitrates, chlorite, chlorate, perchlorate, hypochlorite, peroxide, iodine, ozone, nitrous oxide, silver oxide, permanganate salts, hexavalent chromium compounds, chromic acid, dichromic acids, chromium trioxide, pyridinium chlorochromate, persulfuric acid, sulfoxides, sulfuric acid, Tollens' reagent, 2,2'-dipyridiyldisulfide (DPS), and osmium tetroxide may be used.

In some embodiments, iodine can be used as an oxidizing agent. For example, a solution of iodine can be used and prepared by dissolving iodine in a mixture of pyridine, tetrahydrofuran and water. Elemental sulfur can be used for phosphite oxidation combined with formation of sulfurized product. In some embodiments, other more soluble and more reactive reagents, such as 3H-1,2-benzothiazol-3-one 1,1-dioxide (Beaucage reagent), phenylacetyl disulfide (PADS) or dimethylthiuram (DTD) can be used. Alternatively, peroxides exemplified by t-butyl hydrogen peroxide or m-chlorobenzoyl peroxide may be used for $P^{+3}$ to $P^{+5}$ oxidations.

In some embodiments, an oxidizing reagent is selected from a group consisting of: iodine, hydrogen peroxide, t-butyl hydrogen peroxide, acetone peroxide, sulfur, and thiuram disulfide.

In some embodiments, R and/or $R^1$ is a protecting group or a hydrophobic separation handle. In some embodiments, the method can further include purifying the monoderivatized compound using chromatography (e.g., reverse phase chromatography).

To the monoderivatized product, a reagent of formula (4) or formula (5) is added under conditions that facilitate the conversion of the monoderivatized product to a compound of formula (2). In some embodiments, the reagent is different from the reagent used to prepare the monoderivatized product. In some embodiments, the reagent is the same as that used to prepare the monoderivatized product.

In some embodiments, the conditions are such that conversion of the monoderivatized product to the compound of formula (2) is quantitative.

In some embodiments, conditions that facilitate formation of a compound of formula (2) include the addition of an activating reagent. An activating reagent is then added to the mixture of the monoderivatized product and the reagent of formula (5) or (6). An activating reagent can be any group suitable to initiate coupling of the polymer and the reagent of formula (5) or (6). Suitable activating reagents include, for example, 1H-tetrazole, 5-(ethylthio)-1H-tetrazole (ETT), 5-(benzylthio)-1H-tetrazole (BTT), Activator 42 (5-(3,5-bis (trifluoromethyl)phenyl)-1H-tetrazole), 2-ethylthiotetrazole, 2-bezylthiotetrazole, 4,5-dicyanoimidazoleand 4,5-dicyanoimidazole (DCI). In some embodiments, an activating agent can be selected from pyridinium hydrochloride, pyridinium trifluoroacetate, and buffered carboxylic acids.

In some embodiments, conditions that facilitate formation of a compound of formula (2) include addition of an oxidizing agent to oxidize $P^{+3}$ to $P^{+5}$. Suitable oxidizing agents and conditions can be readily determined by those of ordinary skill in the art. For example, an oxidant such as $RuO_4^-/NMO$, Dess-Martin's reagent, DMSO/triflic anhydride, PDC, hydrogen peroxide, inorganic peroxides, nitric acid, nitrates, chlorite, chlorate, perchlorate, hypochlorite, peroxide, iodine, ozone, nitrous oxide, silver oxide, permanganate salts, hexavalent chromium compounds, chromic acid, dichromic acids, chromium trioxide, pyridinium chlorochromate, persulfuric acid, sulfoxides, sulfuric acid, Tollens' reagent, 2,2'-dipyridiyldisulfide (DPS), and osmium tetroxide may be used.

In some embodiments, iodine can be used as an oxidizing agent. For example, a solution of iodine can be used and prepared by dissolving iodine in a mixture of pyridine, tetrahydrofuran and water. Elemental sulfur can be used for phosphite oxidation combined with formation of sulfurized product. In some embodiments, other more soluble and more reactive reagents, such as 3H-1,2-benzothiazol-3-one 1,1-dioxide (Beaucage reagent), phenylacetyl disulfide (PADS) or dimethylthiuram (DTD) can be used. Alternatively, peroxides exemplified by t-butyl hydrogen peroxide or m-chlorobenzoyl peroxide may be used for $P^{+3}$ to $P^{+5}$ oxidations.

In some embodiments, an oxidizing reagent is selected from a group consisting of: iodine, hydrogen peroxide, t-butyl hydrogen peroxide, acetone peroxide, sulfur, and thiuram disulfide.

In some embodiments, R and/or $R^1$ is a protecting group or a hydrophobic separation handle. In some embodiments, the method can further include purifying the monoderivatized compound using chromatography (e.g., reverse phase chromatography). In some embodiments, the method further includes removal of one or more of the protecting groups. In some embodiments, the method further includes removal of one or more of the hydrophobic separation handles.

For the methods provided above, the deprotection may involve, for example, either sequential or one-pot deprotection of certain protecting groups. Suitable reagents and conditions for the deprotection can be readily determined by those of ordinary skill in the art. For example, deprotection may be achieved upon treatment of the protected compound under conditions so that hydroxyl protecting groups, such as acetate, isopropylidine, benzylidine, trityl, and pixyl protecting groups, are removed from the protected compound. The acetate group can be cleaved under mild conditions, for example, by diluted solution of ammonia or by solution of potassium carbonate. The benzylidene and isopropylidene groups can be cleaved by hydrogenation or using acidic hydrolysis as reported by R. M. Hann et al., *J. Am. Chem. Soc.*, 72, 561 (1950). In yet another example, the deprotection can be performed so that amino protecting groups, such as 9-fluorenylmethyl carbamate (Fmoc), t-butyl carbamate (Boc), and carboxybenzyl carbamate (cbz) protecting groups are cleaved from the protected compound. 9-fluorenylmethyl carbamate (FMOC) can be removed under mild conditions with an amine base (e.g., piperidine) to afford the free amine and dibenzofulvene, as described by E. Atherton et al., "*The Fluorenylmethoxycarbonyl Amino Protecting Group*," in The Peptides, S. Udenfriend and J. Meienhofer, Academic Press, New York, 1987, p. 1. t-butyl carbamate (Boc) can be removed, as reported by G. L. Stahl et al., *J. Org. Chem.*, 43, 2285 (1978), under acidic conditions (e.g., 3 M HCl in EtOAc). Hydrogenation can be used to cleave the carboxybenzyl carbamate (cbz) protecting group as described by J. Meienhofer et al., *Tetrahedron Lett.*, 29, 2983 (1988).

In some embodiments, deprotection may be performed under anaerobic conditions. The deprotection may also be performed at ambient temperature or at temperatures of from about 20-60° C. (e.g., 25, 30, 35, 40, 45, 50, or 55° C.).

In some embodiments, the method can also include isolating the compound by precipitation or crystallization.

Compounds of Formula (3)

Also provided herein is a compound of formula (3):

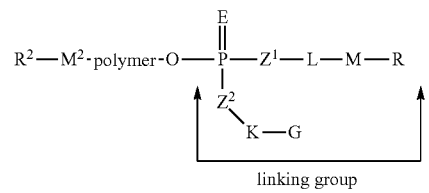

linking group or a salt form thereof, wherein:

polymer is a linear, water-soluble, non-peptidic, and non-nucleotidic polymer backbone, wherein $M^2$ and the phosphonate-derived functional group are bonded at a different terminus of said polymer;

E and $E^1$ are independently O or S;

K is selected from the group consisting of: alkylene, alkyleneoxyalkylene, and oligomeric alkyleneoxyalkylene;

G is selected from the group consisting of hydrogen, alkoxy and a hydrophobic separation handle;

$Z^1$ and $Z^2$ are independently selected from O and NH, wherein only one of $Z^1$ and $Z^2$ can be NH;

L is selected from the group consisting of: a divalent radical of a nucleoside, alkylene, alkyleneoxyalkylene, oligomeric alkyleneoxyalkylene, and unsubstituted and substituted arylene;

M is selected from a protected group that when deprotected is reactive with a biologically active molecule or a derivative thereof or a group reactive with a biologically active molecule;

$M^2$ is selected from O, S or NH; and

R is absent, a protecting group, a hydrophobic separation handle, or an activating group;

$R^2$ is hydrogen or a protecting group;

wherein when M is a protected group that when deprotected is reactive with a biologically active molecule or a derivative thereof, then R is a protecting group or a hydrophobic separation handle; and wherein when M is a group reactive with a biologically active molecule or a derivative thereof, R is absent, hydrogen, or an activating group; and A polymer can be, for example, poly(alkylene glycol), poly(oxyethylated polyol), poly(olefinic alcohol), poly (α-hydroxy acid), poly(vinyl alcohol), polyoxazoline, or a copolymer thereof. Such polyalkylene glycols, include, but are not limited to, polyethylene glycol, polypropylene glycol, polybutylene glycol, and derivatives thereof. Other exemplary embodiments are listed, for example, in commercial supplier catalogs, such as Shearwater Corporation's catalog "Polyethylene Glycol and Derivatives for Biomedical Applications" (2001). By way of example only, such polymeric polyether polyols have average molecular weights between about 0.1 kDa to about 100 kDa. By way of example, such polymeric polyether polyols include, but are not limited to, between about 500 Da and about 100,000 Da or more. The molecular weight of the polymer may be between about 500 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, and 500 Da. In some embodiments, the molecular weight of the polymer is between about 500 Da and about 50,000 Da. In some embodiments, the molecular weight of the polymer is between about 500 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

In some embodiments, the polymer is a poly(ethylene glycol) polymer. The molecular weight of the PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the PEG is between about 1,000 Da and about 50,000 Da. In some embodiments, the molecular weight of the n PEG is between about 1,000 Da and about 40,000 Da. In some embodiments, the molecular weight of the PEG is between about 5,000 Da and about 40,000 Da. In some embodiments, the molecular weight of the PEG is between about 5,000 Da and about 20,000 Da.

In some embodiments, E is oxygen. In some embodiments, E is sulfur.

In some embodiments, K is a linear or branched alkylene. For example, K can be selected from the group consisting of: methylene, ethylene, propylene, isopropylene, butylene, isobutylene, sec-butylene, tert-butylene, and hexylene. In some embodiments, K can be an alkyleneoxyalkylene or an oligomeric alkyleneoxyalkylene. For example, K can be a residue from diethylene glycol, triethylene glycol, tetraethylene glycol or hexaethylene glycol. In some embodiments, K is selected from the group consisting of $-(CH_2)_n-$ and $-((CH_2)_n-O-(CH_2)_m)_p-$, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In some embodiments, G is a hydrophobic separation handle. For example, G can be a substituted or unsubstituted trityloxy group. In some embodiments, G is selected from the group consisting of monoalkoxy substituted trityloxy group or dialkoxy substituted trityloxy group.

In some embodiments, one of $Z^1$ and $Z^2$ is NH and the other is O. For example, $Z^1$ is O and $Z^2$ is NH; $Z^1$ is NH and $Z^2$ is O. In some embodiments, both $Z^1$ and $Z^2$ are O.

In some embodiments, L is a linear or branched alkyl. For example, L can be selected from the group consisting of: methylene, ethylene, propylene, isopropylene, butylene, isobutylene, sec-butylene, tert-butylene, and hexylene. In some embodiments, L can be an alkyleneoxyalkylene or an oligomeric alkyleneoxyalkylene. For example, L can be a residue from diethylene glycol, triethylene glycol, tetraethylene glycol or hexaethylene glycol. In some embodiments, L is selected from the group consisting of $-(CH_2)_n-$ and $-((CH_2)_n-O-(CH_2)_m)_p-$, wherein n is an integer from 1 to 50 (e.g., 1 to 40, 1 to 30, 1 to 25, 1 to 20, 1 to 18, 1 to 15, 1 to 12, 1 to 10, 1 to 6, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), m is an integer from 0 to 50 (e.g., 1 to 40, 1 to 30, 1 to 25, 1 to 20, 1 to 18, 1 to 15, 1 to 12, 1 to 10, 1 to 6, 1 to 2, 1 to 3, 1 to 4, 2 to 50, 5 to 50, 10 to 50, 15 to 50, 25 to 50, 5 to 15, 2 to 12, 20 to 30, and 6 to 18), and each p is independently an integer from 1 to 10 (e.g., 1 to 8, 1 to 6, 1 to 5, 1 to 3, 2 to 10, 4 to 10, 6 to 10, 2 to 8, and 3 to 6).

In some embodiments, L is a substituted or unsubstituted arylene. For example, L can be a structure with the formula:

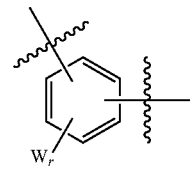

wherein W is a substituent and r is an integer from 0 to 4. For example, W can be selected from the group consisting of: halo, $C_1$-$C_{10}$ alkyl, $C_2$-$C_{10}$ alkenyl, $C_2$-$C_{10}$ alkynyl, alkoxy, $C_5$-$C_{12}$ aralkyl, $C_3$-$C_{12}$ cycloalkyl, $C_4$-$C_{12}$ cycloalkenyl, phenyl, substituted phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, $-(CH_2)_m-O-(C_1$-$C_{10}$ alkyl) wherein m is from 1 to 8, aryl, substituted aryl, substituted alkoxy, fluoroalkyl, heterocyclic radical, substituted heterocyclic radical, nitroalkyl, $-NO_2$, $-CN$, $-NR^9C(O)-(C_1$-$C_{10}$ alkyl), $-C(O)-(C_1$-$C_{10}$ alkyl), $C_2$-$C_{10}$ alkthioalkyl, $-C(O)O-(C_1$-$C_{10}$ alkyl), $-OH$, $-SO_2$, $=S$, $-COOH$, $-NR^9_2$, carbonyl, $-C(O)-(C_1$-$C_{10}$ alkyl)-$CF_3$, $-C(O)-CF_3$, $-C(O)NR^9_2$, $-(C_1$-$C_{10}$ aryl)-S-$(C_6$-$C_{10}$ aryl), $-C(O)-(C_6$-$C_{10}$ aryl), $-(CH_2)_m-O-(CH_2)_m-O-(C_1$-$C_{10}$ alkyl) wherein each m is from 1 to 8, $-C(O)NR^9_2$, $-C(S)NR^9_2$, $-SO_2NR^9_2$, $-NR^9C(O)NR^9_2$, $-NR^9C(S)NR^9_2$, salts thereof, and the like. Each $R^9$ group in the preceding list independently includes, but is not limited to, H, alkyl or substituted alkyl, aryl or substituted aryl, or alkylaryl. In some embodiments, W is $R^1$ as described above.

Non-limiting examples of L include:

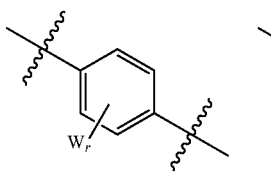 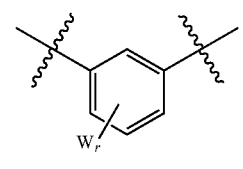

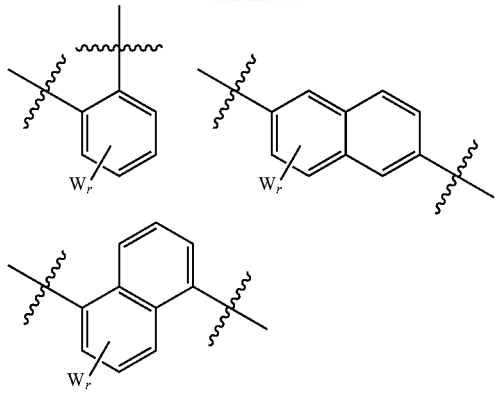

L can also be a divalent radical of a nucleoside. For example, L can be a divalent radical of a natural nucleoside, such as adenosine, deoxyadenosine, guanosine, deoxyguanosine, 5-methyluridine, thymidine, uridine, deoxyuridine, cytidine, and deoxycytidine.

A group reactive with a biologically active molecule or a derivative thereof can be selected from the group consisting of: hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide. In some embodiments, the group is protected or further reacted with a group R as shown in the structure of formula (3). The point of attachment of such a group is well understood by those of skill in the art.

In some embodiments, R is absent.

In some embodiments, $R^2$ is hydrogen.

In some embodiments, R and/or $R^2$ is a protecting group. For this purpose, R and/or $R^2$ may include any suitable protecting group based on the group to be protected. For example, R and/or $R^2$ may include any suitable hydroxyl functional group including, but not limited to, ether, ester, carbonate, or sulfonate protecting groups.

In particular, the ether protecting group may include benzyloxymethyl (BOM), methylthiomethyl (MTM), phenylthiomethyl (PTM), cyanoethyl, 2,2-dichloro-1,1-difluoroethyl, 2-chloroethyl, 2-bromoethyl, tetrahydropyranyl (THP), phenacyl, 4-bromophenacyl, allyl, propargyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylemethyl, 4-picolyl, heptafluoro-p-tolyl, tetrafluoro-4-pyridyl, trimethylsilyl (TMS), and protecting groups.

The ester protecting group may include acetoxy (OAc), aryl formate, acetate, levulinate, pivaloate, benzoate, and 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC-OAr), 4-methylsulfinylbenzyl carbonate (Msz-OAr), 2,4-dimethylpent-3-yl carbonate (Doc-OAr), aryl 2,2,2-trichloroethyl carbonate.

The sulfonate protecting groups may include aryl methanesulfonate, aryl toluenesulfonate, and aryl 2-formylbenzenesulfonate.

In some embodiments, R may include any suitable amino protecting group, including, but not limited to, carbamate, amide, N-alkyl, or N-aryl-derived protecting groups.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzol[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)]methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N,N-dicycloheylcarboxamido)ethyl carbamate, 1-adamanyl carbamate (1-Adoc), cinyl carbamate (Voc), 1-isopropylallyl carbamate (Ipaoc), 4-nicrocinnamyl carbamate (Noc), 3-(3'pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methyl sulfinylbenzyl carbamate (Msz), diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In some embodiments, the carbamate protecting group is chosen from 9-fluorenylmethyl carbamate (Fmoc), t-butyl carbamate (Boc), and carboxybenzyl carbamate (cbz).

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide.

Examples of suitable protecting groups also include tert-butyl, benzyl, 4-methoxybenzyl, benzyloxymethyl, phenacyl, allyl, trimethylsilyl, benzyloxycarbonyl, tert-butoxycarbonyl, and acetal and ketal derivatives. In some embodiments, R is selected from trityls, substituted trityls (e.g., monomethoxytrityl (MMTr), dimethoxytrityl (DMTr), trimethoxytrityl (TMTr), 2-chlorotrityl (ClTr) and p-bromophenacyloxytrityl (BPTr), pixyls and substituted pixyls (see, for example, U.S. Publication No. 2007/0276139). In some embodiments, R is selected from trityl, monoalkoxytrityl, dialkoxytrityl, pixyl, alkoxypixyl, fluorenylmethyloxycarbonyl, trifluoroacetyl, acetal, and cyclic acetal.

In some embodiments, R is a hydrophobic separation handle.

A hydrophobic separation handle is as described herein. In some embodiments, the hydrophobic separation handle is also a protecting group as described herein. In some embodiments, at least one of R and G is a hydrophobic separation handle.

In some embodiments, only one of R and G is a hydrophobic separation handle (e.g., a trityl group) as provided herein. For example, if R is a hydrophobic separation handle, then G is hydrogen or an alkoxy. In some embodiments, R is a protecting group and G is hydrogen or an alkoxy. In some embodiments, R is absent and G is a trityloxy group. In some embodiments, the hydrophobic separation handle is a substituted or unsubstituted trityl or trityloxy group. For example, only one of R and G is a substituted or unsubstituted trityl or trityloxy group.

In some embodiments, $R^2$ is absent or is selected from the group consisting of: trityl, monoalkoxytrityl, dialkoxytrityl, pixyl, alkoxypixyl, fluorenylmethyloxycarbonyl, alkylcarboxyl, benzoyl, tetrahydropyranyl, and methyl.

A compound of formula (3) can be prepared, for example, by contacting a monosubstituted polymer comprising a linear, water-soluble, non-peptidic and non-nucleotidic polymer backbone bonded at the first terminus with the functional group $M^2$-$R^2$, with a reagent of formula (5):

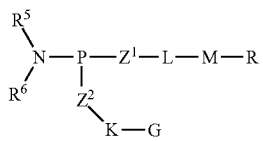

wherein:

$R^5$ and $R^6$ independently from each other represent $C_1$-$C_6$-alkyl or $R^5$ and $R^6$ jointly form a 5- or 6-membered ring with the N to which they are bonded; under conditions facilitating the conversion of the monosubstituted polymer to a compound of formula (3).

In some embodiments, $R^5$ and $R^6$ are independently a $C_1$-$C_6$-alkyl. For example, $R^5$ and $R^6$ can be independently selected from the group consisting of methyl, ethyl, propyl, isopropyl, butyl, isobutyl, sec-butyl, tert-butyl, and hexyl. In some embodiments, $R^5$ and $R^6$ are isopropyl. In some embodiments, $R^5$ and $R^6$ jointly form a 5- or 6-membered ring with the N to which they are bonded. For example, $R^5$ and $R^6$ jointly form a pyrrolidine, pyrroline, imidazoline, pyrazolidine, piperidine, 1,2,3,6-tetrahydropyridine, 1,4-dihydropyridine, piperazine, morpholine, thiomorpholine, pyridyl, pyrazinyl, pyrimidinyl, particularly 2- and 4-pyrimidinyl, pyridazinyl, pyrrolyl, particularly 2-pyrrolyl, imidazolyl, thiazolyl, oxazolyl, and pyrazolyl, particularly 3- and 5-pyrazolyl. In some embodiments, $R^5$ and $R^6$ jointly form a morpholine ring.

The ratio of a monosubstituted polymer to a reagent of formula (5) can range from about 1:10 to about 10:1 (e.g., about 2:1, about 3:1, about 4:1, about 5:1, about 6:1, about 7:1, about 8:1, about 9:1, about 1:2, about 1:3, about 1:4, about 1:5, about 1:6, about 1:7, about 1:81 about 1:9, about 2:8, about 3:7, about 4:6 about 5:10, and about 4:8). In some embodiments, the ratio of a polymer to a reagent of formula (5) is from about 1:1 to about 1:10. In some embodiments, the ratio of a polymer to a reagent of formula (5) is about 2:1.

In some embodiments, the conversion of a monosubstituted polymer to a compound of formula (3) is quantitative.

In some embodiments, conditions that facilitate formation of a compound of formula (3) include the addition of an activating reagent. An activating reagent is then added to the mixture of the monoderivatized product and the reagent of formula (5) or (6). An activating reagent can be any group suitable to initiate coupling of the polymer and the reagent of formula (5) or (6). Suitable activating reagents include, for example, 1H-tetrazole, 5-(ethylthio)-1H-tetrazole (ETT), 5-(benzylthio)-1H-tetrazole (BTT), Activator 42 (5-(3,5-bis(trifluoromethyl)phenyl)-1H-tetrazole), 2-ethylthiotetrazole, 2-bezylthiotetrazole, 4,5-dicyanoimidazole and 4,5-dicyanoimidazole (DCI). In some embodiments, an activating agent can be selected from pyridinium hydrochloride, pyridinium trifluoroacetage, and buffered carboxylic acids.

In some embodiments, conditions that facilitate formation of a compound of formula (3) include addition of an oxidizing agent to oxidize $P^{+3}$ to $P^{+5}$. Suitable oxidizing agents and conditions can be readily determined by those of ordinary skill in the art. For example, an oxidant such as $RuO_4^-$/NMO, Dess-Martin's reagent, DMSO/triflic anhydride, PDC, hydrogen peroxide, inorganic peroxides, nitric acid, nitrates, chlorite, chlorate, perchlorate, hypochlorite, peroxide, iodine, ozone, nitrous oxide, silver oxide, permanganate salts, hexavalent chromium compounds, chromic acid, dichromic acids, chromium trioxide, pyridinium chlorochromate, persulfuric acid, sulfoxides, sulfuric acid, Tollens' reagent, 2,2'-dipyridiyldisulfide (DPS), and osmium tetroxide may be used.

In some embodiments, iodine can be used as an oxidizing agent. For example, a solution of iodine can be used and prepared by dissolving iodine in a mixture of pyridine, tetrahydrofuran and water. Elemental sulfur can be used for phosphite oxidation combined with formation of sulfurized product. In some embodiments, other more soluble and more reactive reagents, such as 3H-1,2-benzothiazol-3-one 1,1-dioxide (Beaucage reagent), phenylacetyl disulfide (PADS) or dimethylthiuram (DTD) can be used. Alternatively, peroxides exemplified by t-butyl hydrogen peroxide or m-chlorobenzoyl peroxide may be used for $P^{+3}$ to $P^{+5}$ oxidations.

In some embodiments, an oxidizing reagent is selected from a group consisting of: iodine, hydrogen peroxide, t-butyl hydrogen peroxide, acetone peroxide, sulfur, and thiuram disulfide.

In some embodiments, R and/or $R^1$ is a protecting group or a hydrophobic separation handle. In some embodiments, the method can further include purifying the monoderivatized compound using chromatography (e.g., reverse phase chromatography). In some embodiments, the method further includes removal of one or more of the protecting groups. In some embodiments, the method further includes removal of one or more of the hydrophobic separation handles.

For the methods provided above, the deprotection may involve, for example, either sequential or one-pot deprotection of certain protecting groups. Suitable reagents and conditions for the deprotection can be readily determined by those of ordinary skill in the art. For example, deprotection may be achieved upon treatment of the protected compound under conditions so that hydroxyl protecting groups, such as acetate, isopropylidine, benzylidine, trityl, and pixyl protecting groups, are removed from the protected compound. The acetate group can be cleaved under mild conditions, for example, by diluted solution of ammonia or by solution of potassium carbonate. The benzylidene and isopropylidene groups can be cleaved by hydrogenation or using acidic hydrolysis as reported by R. M. Hann et al., *J. Am. Chem. Soc.*, 72, 561 (1950). In yet another example, the deprotection can be performed so that amino protecting groups, such as 9-fluorenylmethyl carbamate (Fmoc), t-butyl carbamate (Boc), and carboxybenzyl carbamate (cbz) protecting groups are cleaved from the protected compound. 9-fluorenylmethyl carbamate (FMOC) can be removed under mild conditions with an amine base (e.g., piperidine) to afford the free amine and dibenzofulvene, as described by E. Atherton et al., "*The Fluorenylmethoxycarbonyl Amino Protecting Group*," in The Peptides, S. Udenfriend and J. Meienhofer, Academic Press, New York, 1987, p. 1. t-butyl carbamate (Boc) can be removed, as reported by G. L. Stahl et al., *J.*

*Org. Chem.*, 43, 2285 (1978), under acidic conditions (e.g., 3 M HCl in EtOAc). Hydrogenation can be used to cleave the carboxybenzyl carbamate (cbz) protecting group as described by J. Meienhofer et al., *Tetrahedron Lett.*, 29, 2983 (1988).

In some embodiments, deprotection may be performed under anaerobic conditions. The deprotection may also be performed at ambient temperature or at temperatures of from about 20-60° C. (e.g., 25, 30, 35, 40, 45, 50, or 55° C.).

In some embodiments, the method can also include isolating the compound of formula (3) by precipitation or crystallization.

Non-limiting examples of linking groups for use in the compounds provided herein include:

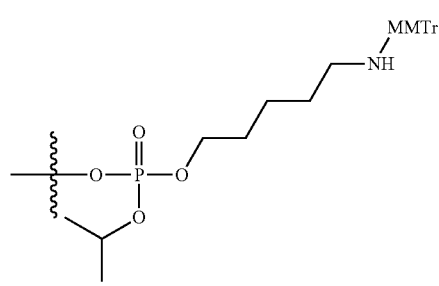

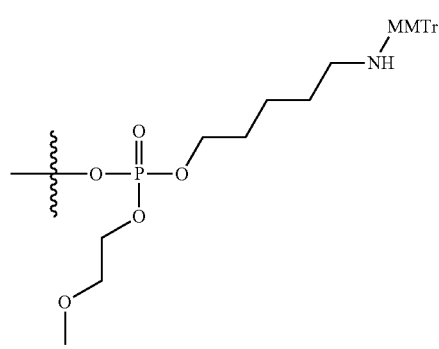

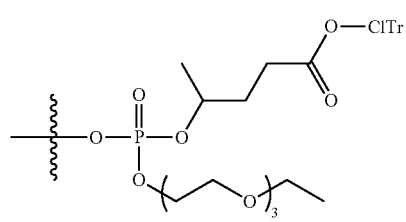

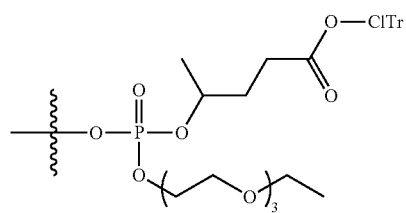

-continued

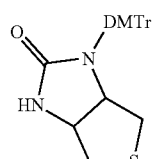

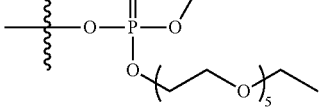

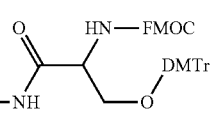

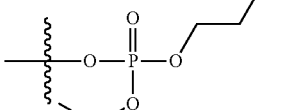

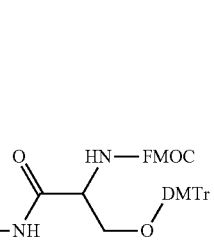

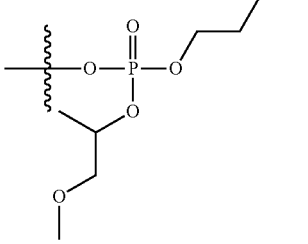

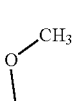

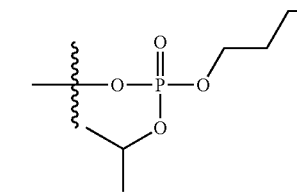

49
-continued
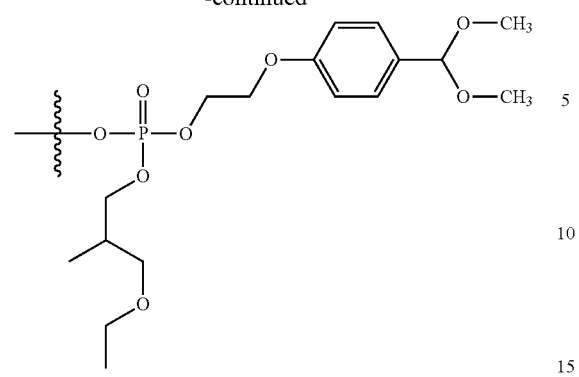
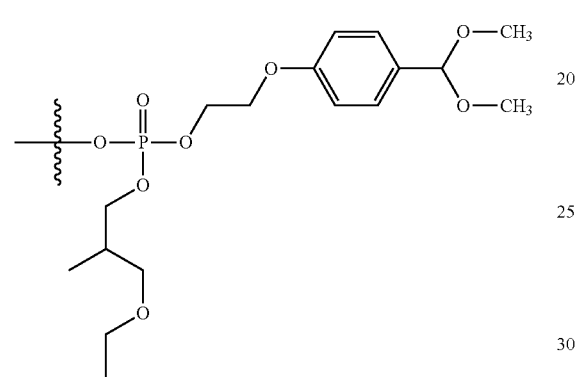
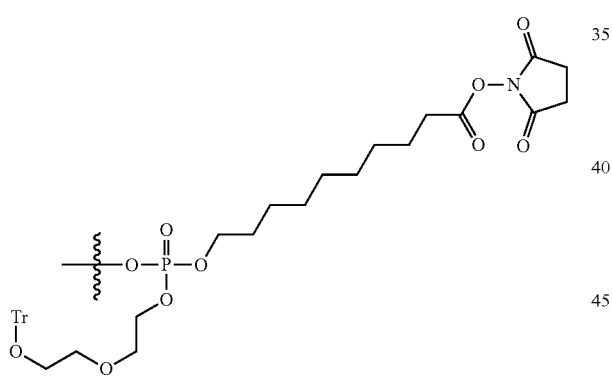
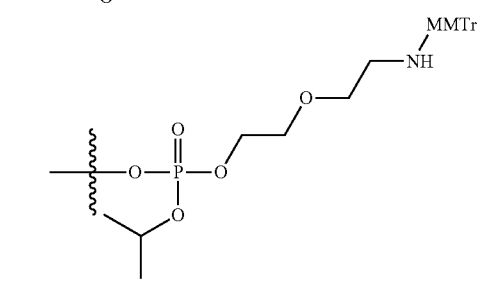
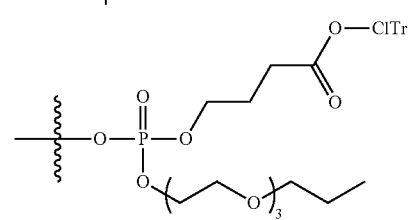
50
-continued
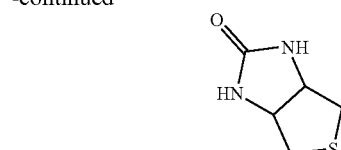
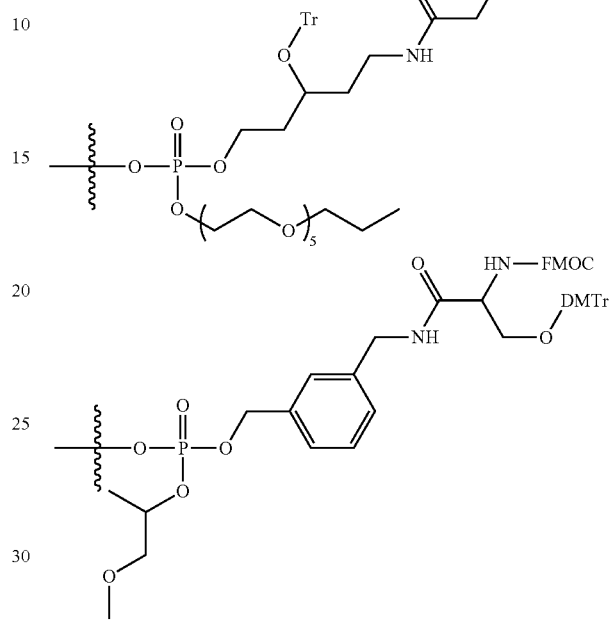
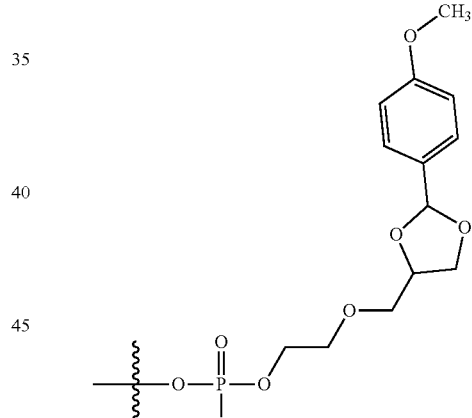
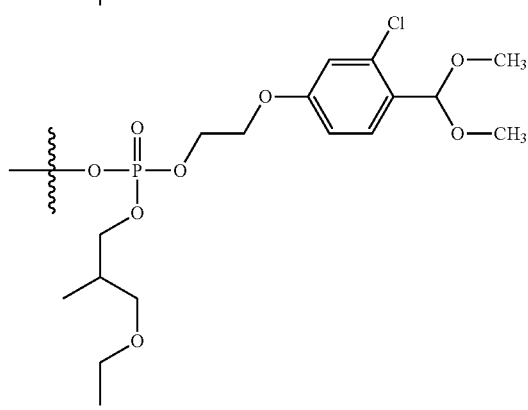

-continued
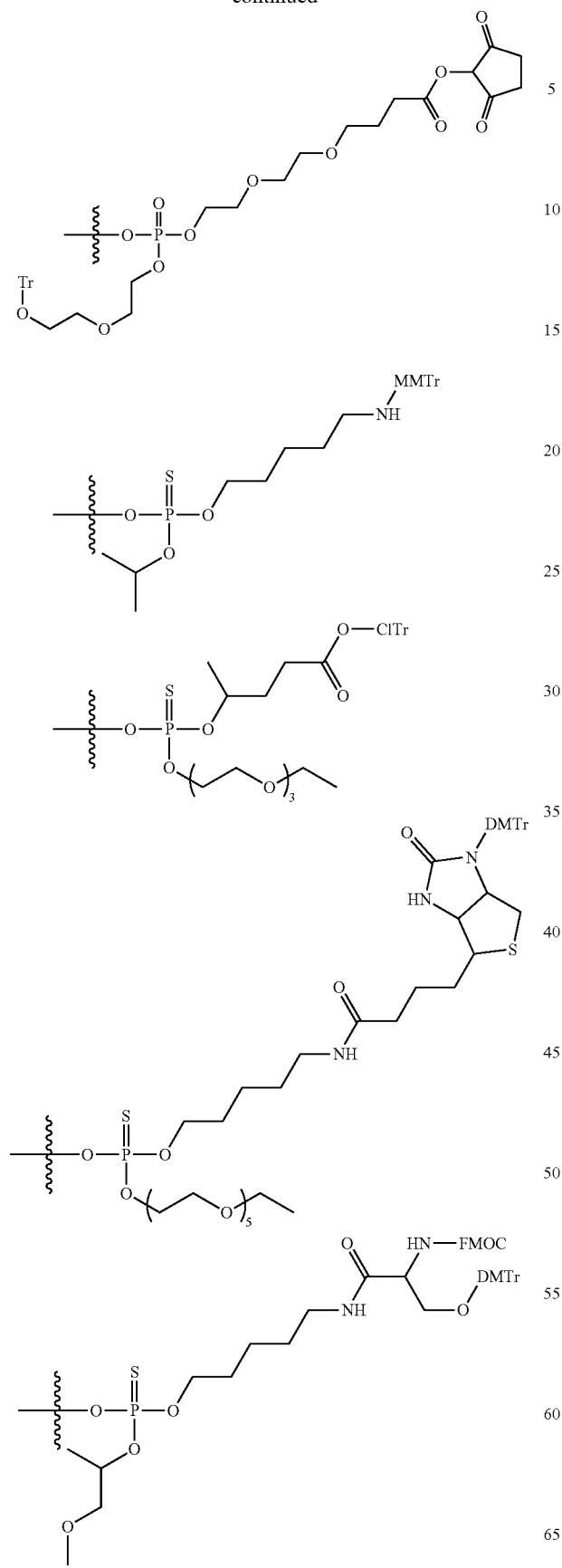
-continued
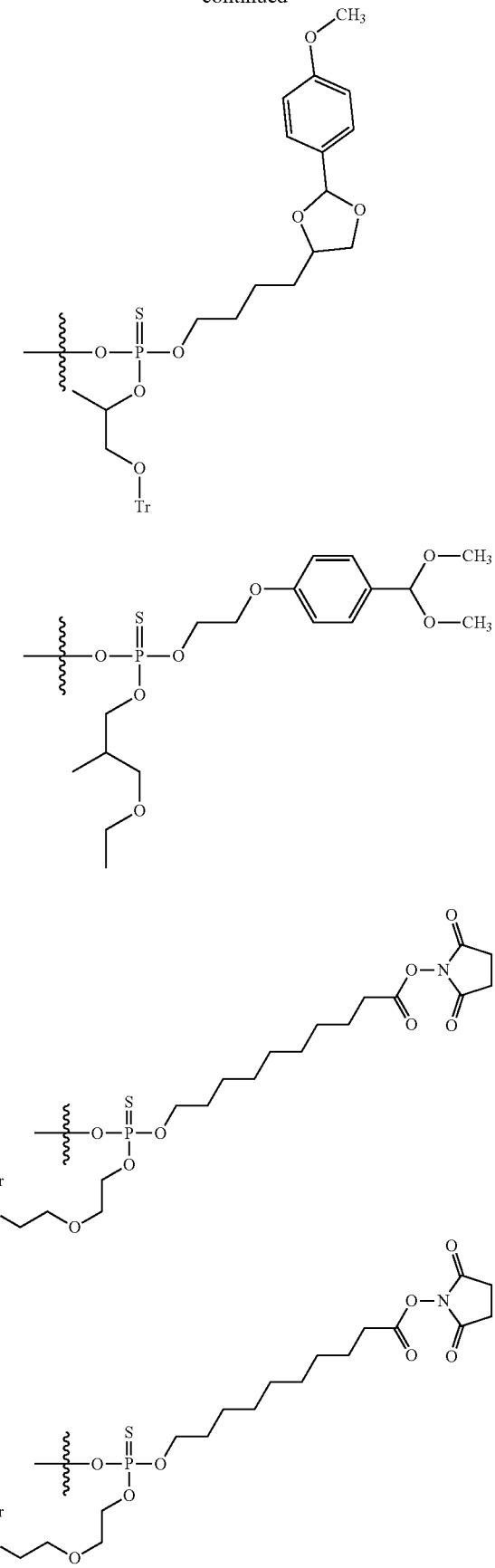

53
-continued
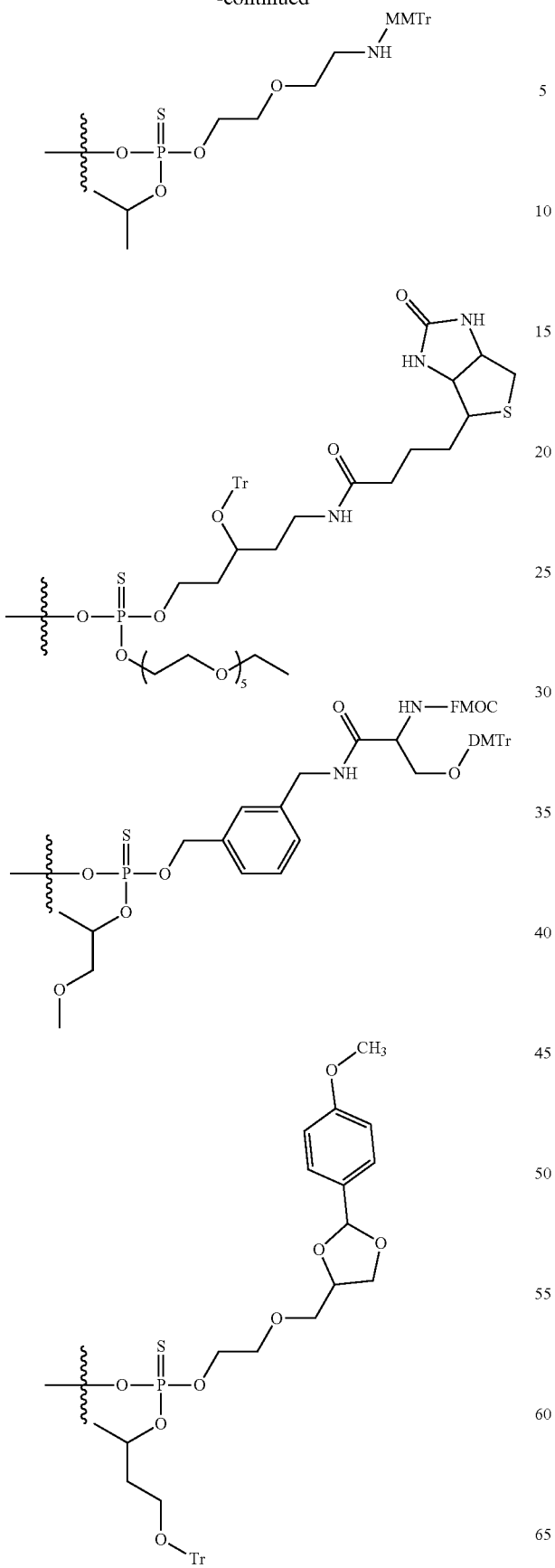
54
-continued
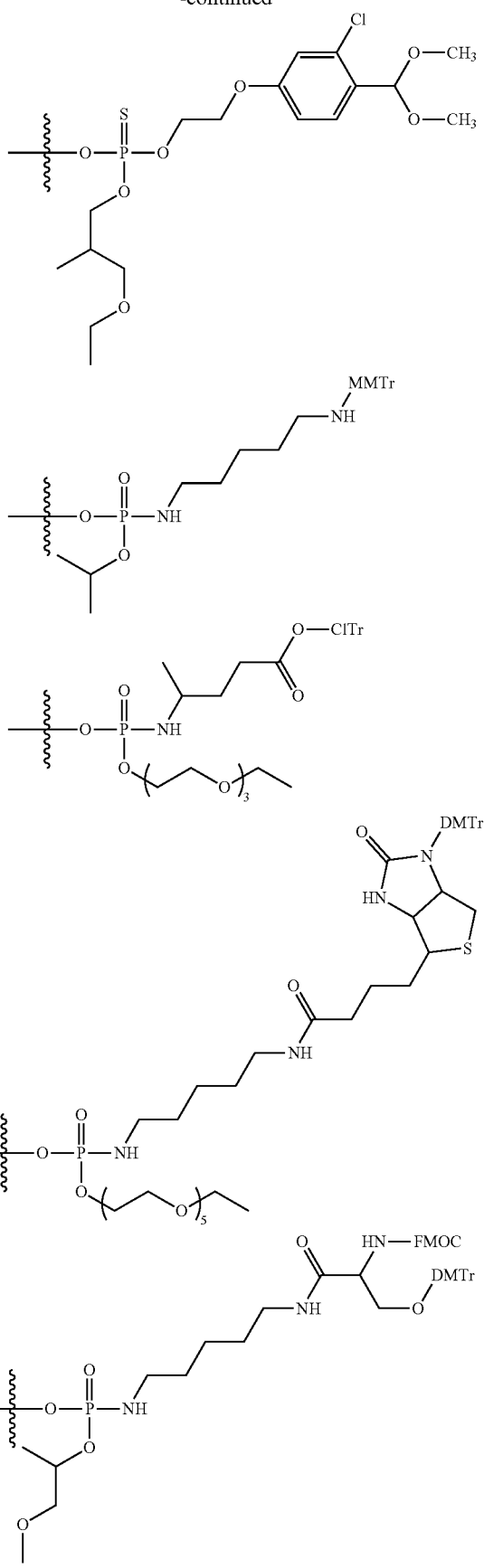

55
-continued
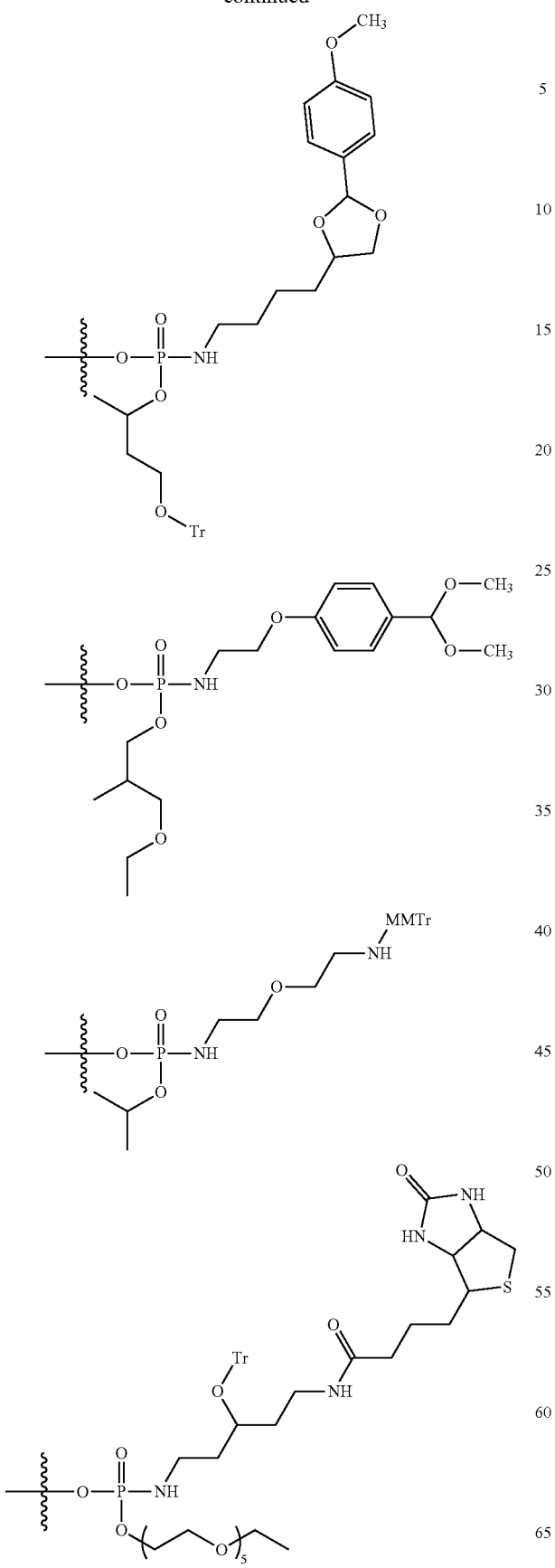
56
-continued
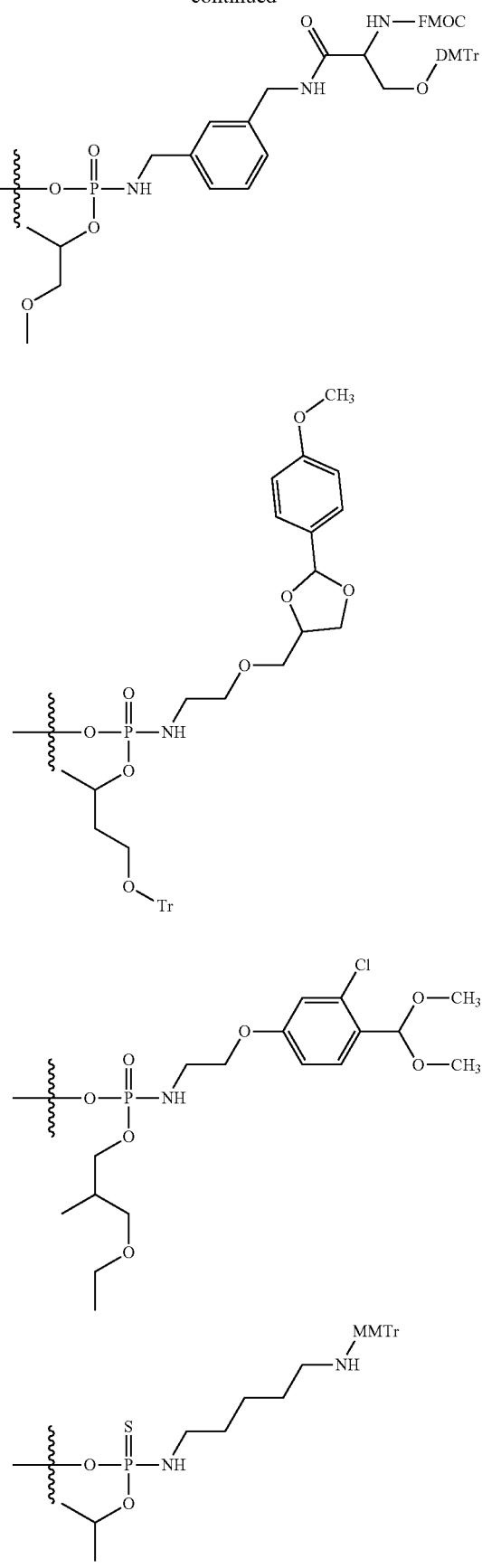

57
-continued
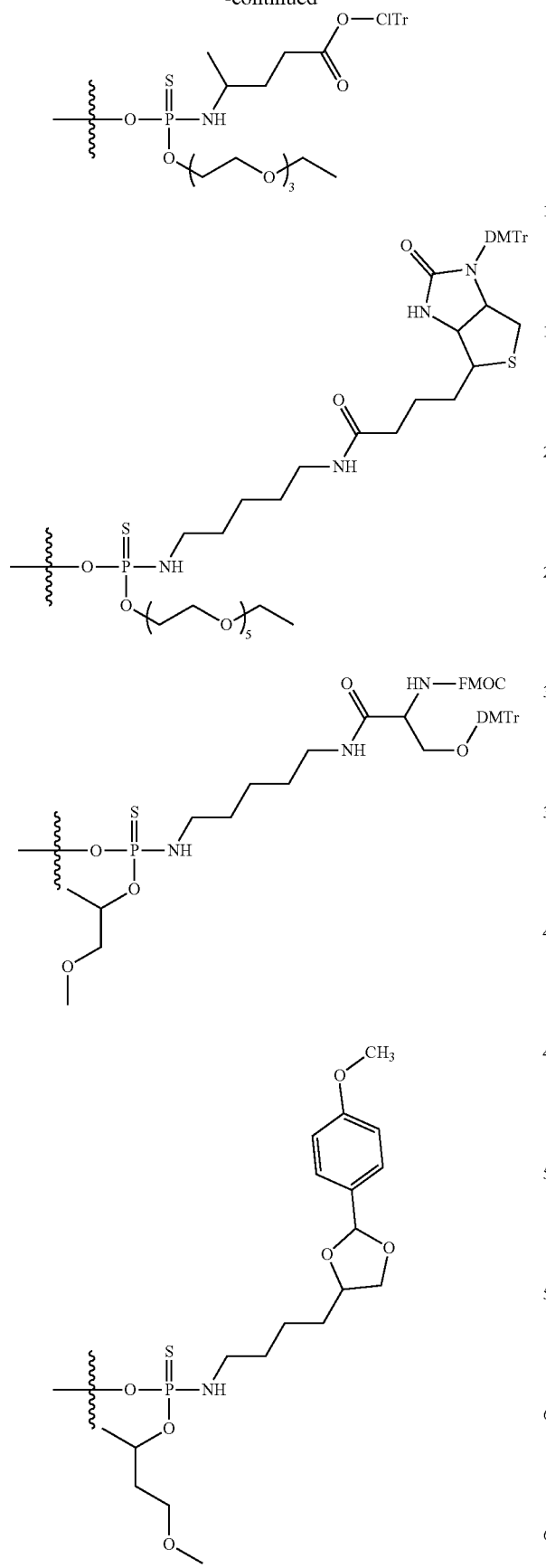
58
-continued
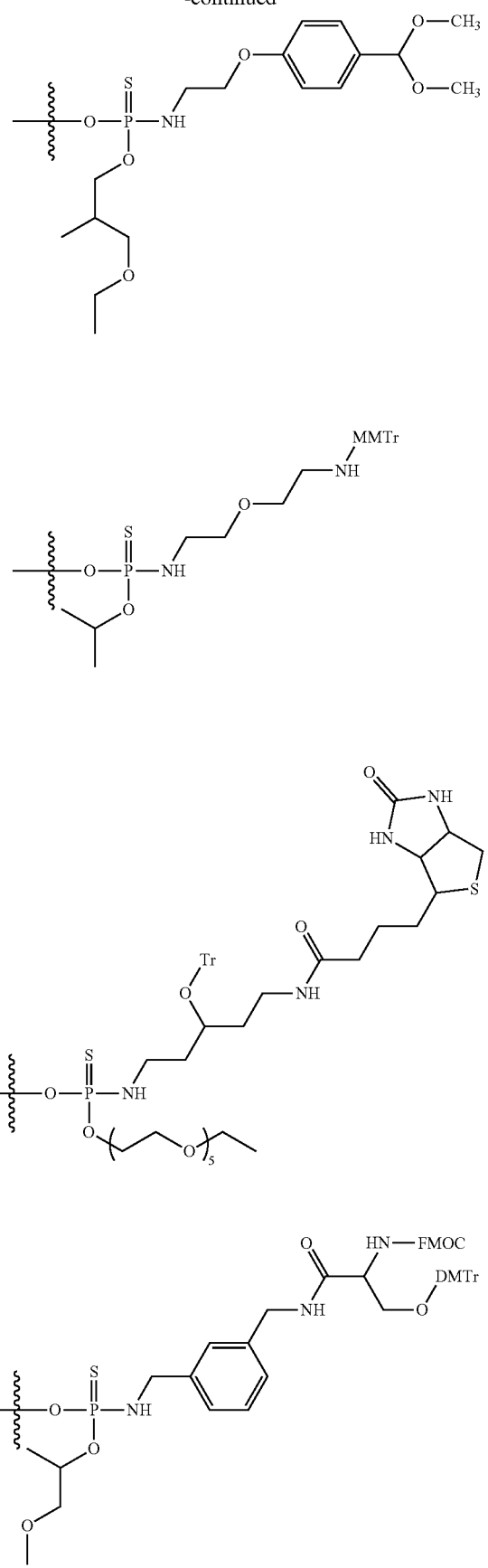

59
-continued
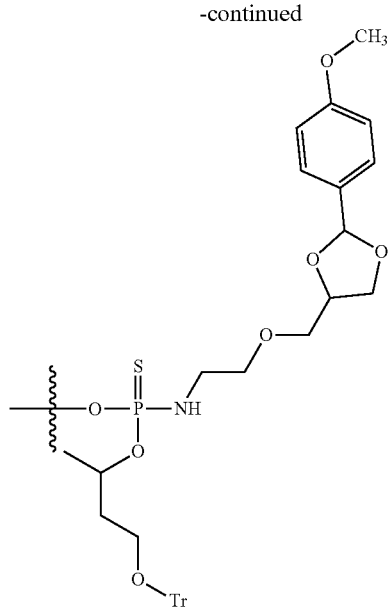
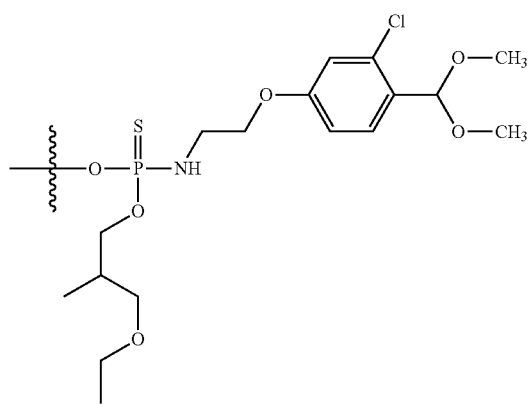 [SMILES: *OP(=S)(NCC(C)COCC)OCCOc1ccc(C(OC)OC)c(Cl)c1]
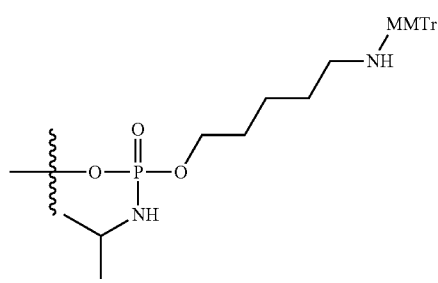
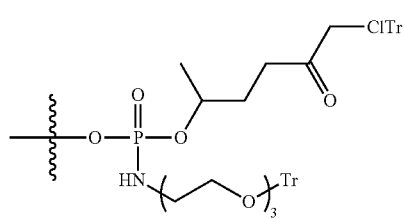
60
-continued
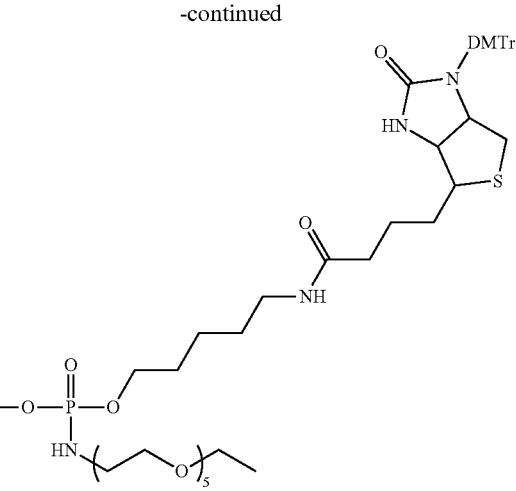
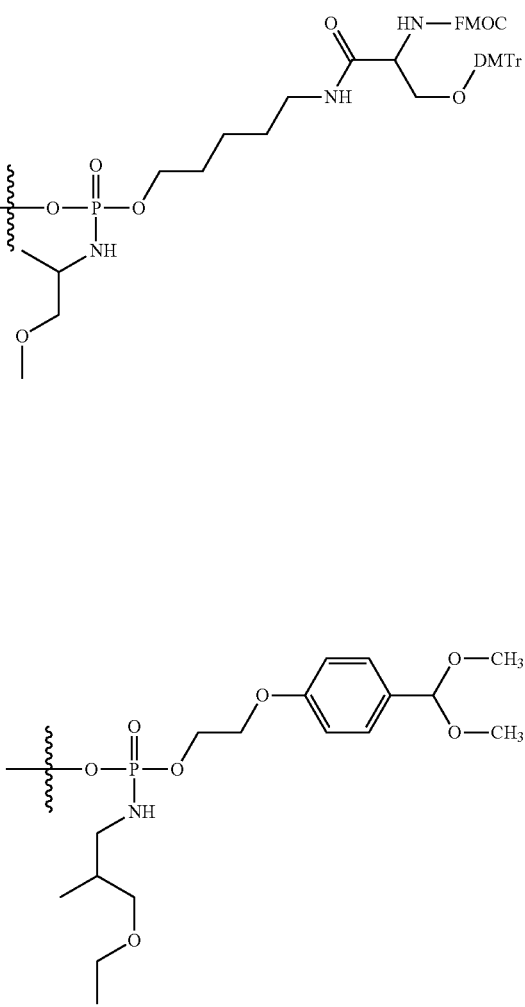

61
-continued
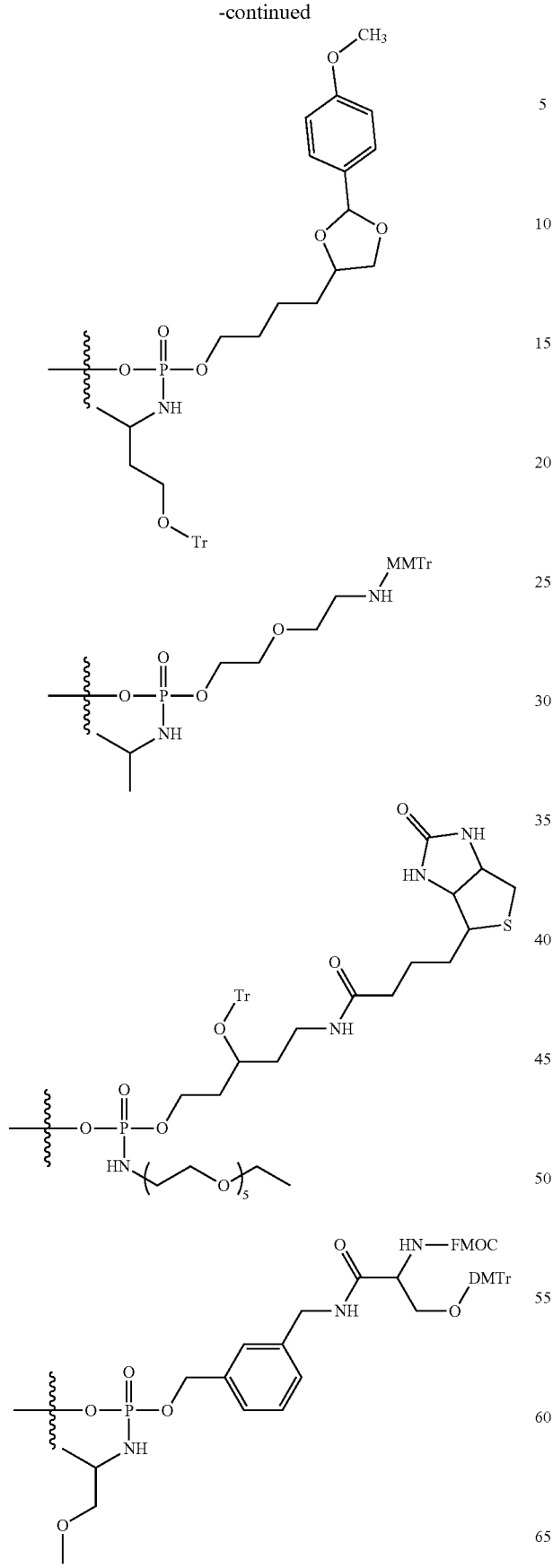
62
-continued
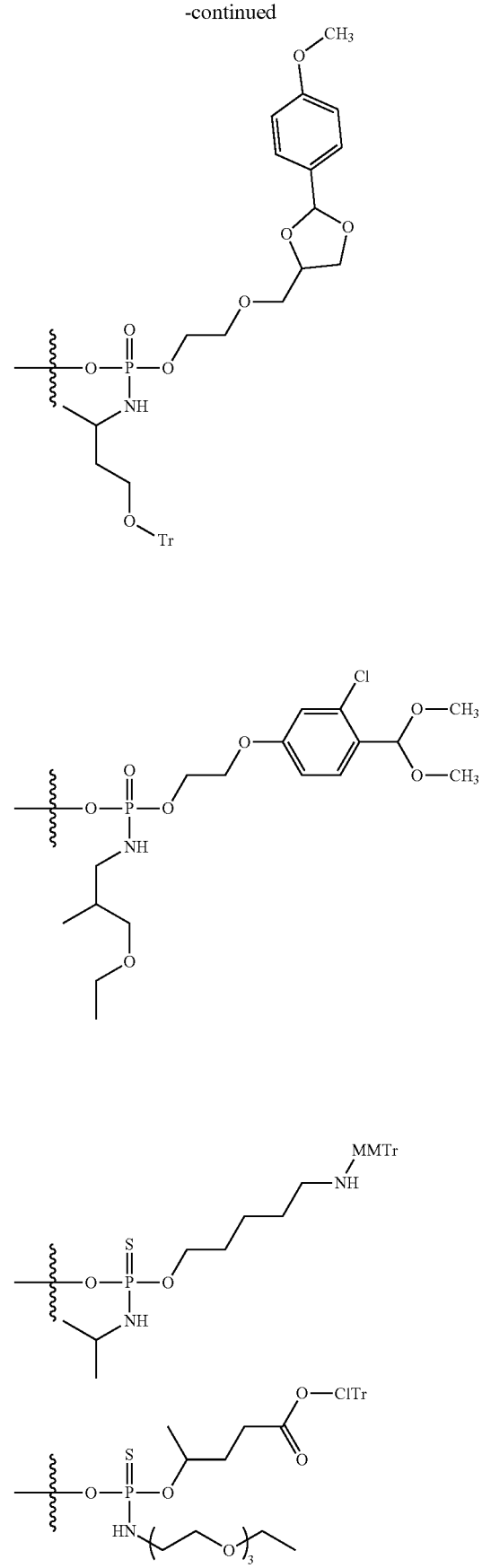

63
-continued
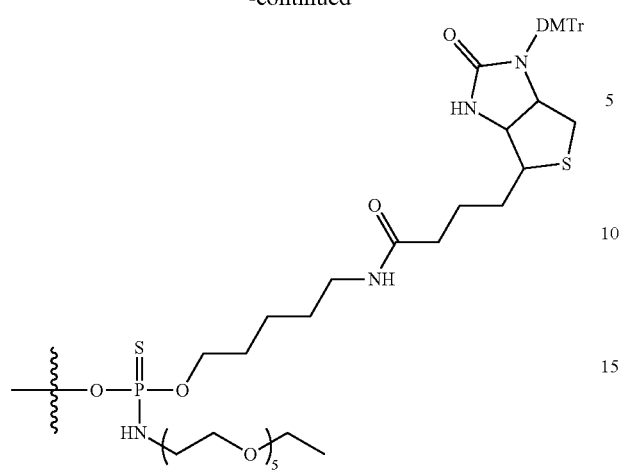
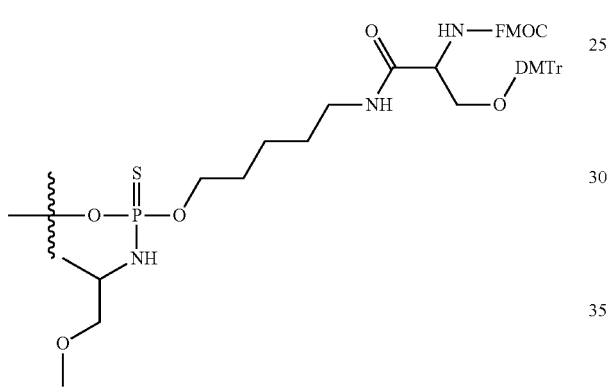
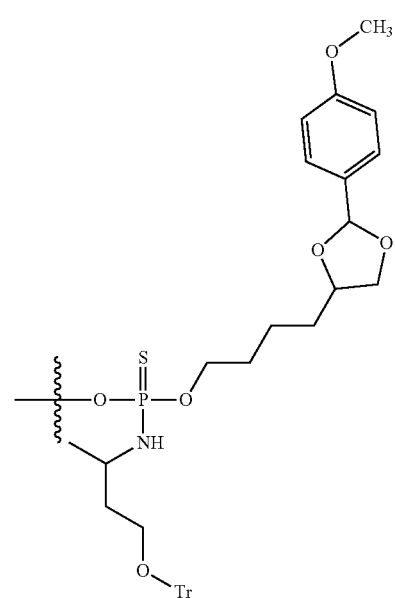
64
-continued
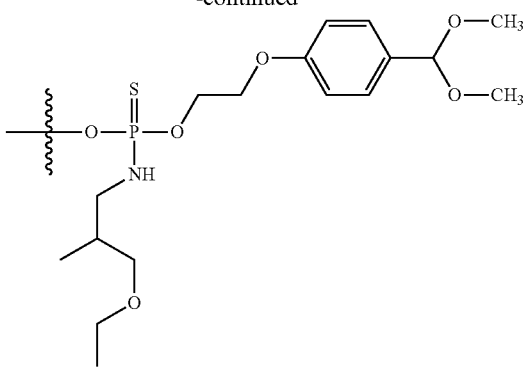
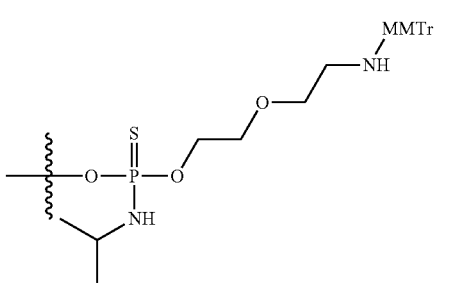
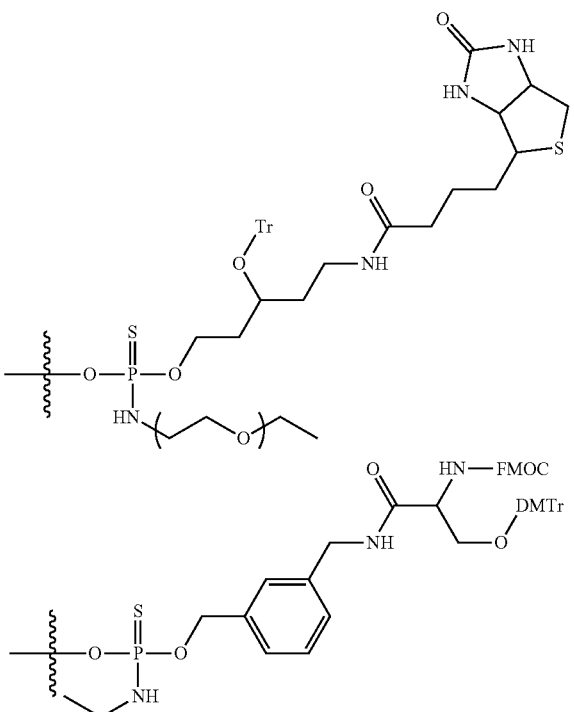

-continued

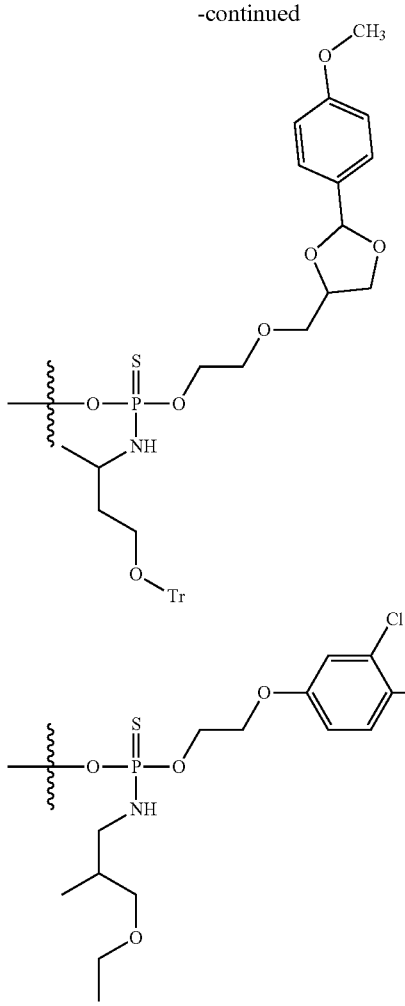

Provided herein is a new type of functional, water-soluble polymer, not belonging to the classes of polypeptides or nucleotides and containing the structure of formula (1) that can be conjugated to a biologically active molecule or a derivative thereof:

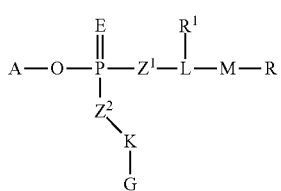

In this schematic picture of such a modified polymer, A is the point of bonding to the terminus of the polymer backbone, E is an oxygen or sulfur atom, K is selected from the group consisting of alkylene, alkyleneoxyalkylene, or an oligomeric form of alkyleneoxyalkylene, G is hydrogen or is selected from the group consisting of an alkoxy and a hydrophobic separation handle, $Z^1$ and $Z^2$ can be oxygen or nitrogen, in such way that both $Z^1$ and $Z^2$ may be oxygen, but when $Z^1$ is NH then $Z^2$ is oxygen, and when $Z^2$ is NH then $Z^1$ is oxygen, L is selected from the group consisting of a divalent radical of a nucleoside, linear alkylene, branched alkylene, alkyleneoxyalkylene, oligomeric form of alkyleneoxyalkylene, arylene, and substituted arylene, M is a protected group that when deprotected is reactive with a biologically active molecule or a derivative thereof or is a group reactive with a biologically active molecule or a derivative thereof, R is a protecting group, activating group, hydrogen or absent. Thus the L-M-R fragment is linked to a terminus of the polymer via a phosphotriester, thiophosphotriester or amidophosphotriester group.

One characteristic of a compound provided herein is that the functional group M, via the group L, is connected to the chain of the polymer via a phosphotriester group or amido phosphodiester, known also as phosphoramidate group. In addition, a derivatized polymer may exist both in an oxy and a thio form. Non-limiting examples of such groups include:

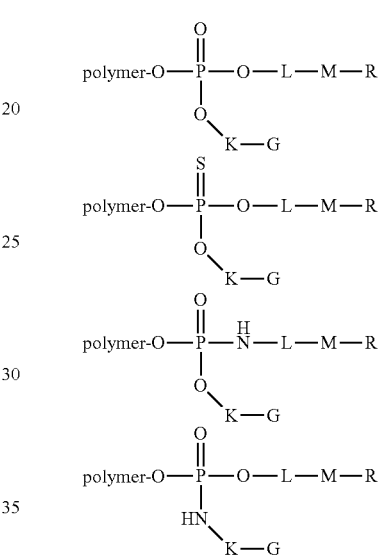

An important class of polymers provided herein, polyethylene glycols (PEG), were previously used in the synthesis of phosphoramidites of the formula: DMTr-O-PEG-O—P(OCE)N(iPr)$_2$. These compounds were used for direct coupling of PEG molecules to synthetic nucleic acids or to a surface of a solid phase. In all reactions, the reactive phosphoramidite group was present at the terminal of the polymer. A polymer substituted with a phosphoramidite group is, however, not a subject of the present disclosure, as the phosphorous atom in the phosphoramidite group is the part of the reactive functionality and not a part of the linker as in the compounds provided herein.

This formal distinction can have a deeper chemical importance. A phosphoramidite group can be designed to work in a completely water-free environment. Upon activation with certain protonating agents/activators a phosphoramidite group can become extremely reactive, and in the presence of water, this reactive function can decompose instantaneously, making this function inappropriate for conjugation to a biologically active molecule or a derivative thereof in aqueous solution. Additionally, published PEG phosphoramidites can contain a specially designed, labile protecting group adjacent to the phosphorous atom to convert the intermediate phosphotriester to a phosphodiester. The present document is based, at least in part, on the observation that phosphodiesters are unstable in aqueous biological media such as blood, plasma or cellular extracts, due to the presence of phosphatases and phosphodiesterases. This can preclude phosphodiester linkages as a linking group within a structure of a conjugate, as long as it is aimed for use in biological media. This document, contrary to the existing literature, and contrary to all normal procedures, recommends keeping the phosphate in the form of a phosphotriester or in the form of its amide in order to gain stability of the linking group/conjugate.

Phosphotriester bonds are very rare in nature, existing in most of the cases as cyclic products of RNA transformations. As non-charged variants of nucleotides they gained some attention from those who hoped that it could be possible to use this form of nucleotides as predrugs, which would be transformed in vivo to the active phosphodiester forms. However, acyclic phosphotriesters, lacking specially designed internal features facilitating deprotection, were found completely stable, both chemically at the physiological pH range, and enzymatically in the presence of the most active phosphate hydrolytic enzymes: McGuigan et al., *Nucl. Acids Res.* 1989, 17 (15), 6065-6075; Hecker and Erion, *J. Med. Chem.* 2008, 51, 2328-2345; Conrad et al. *Chem. Bio. Interactions* 1986, 60, 57-65; and Fidanza et al., *Methods in Molecular Biology* 1994, 26, 121-143.

The proposed way of linking a functional group to the polymeric molecule can include combining chemistry typical for nucleic acids with chemistry of polymers and their conjugates. Moreover, this combination can be performed in a way to yield a product with distinctly better characteristics than if this combination of chemistries would proceed following the standard path.

This document also provides methods and materials for introducing of a useful separation handle on the derivatized polymer. This separation handle can be introduced simultaneously with the functional group, so the presence of the separation handle becomes an indicator of successful introduction of the reactive group. If chromatographic properties of a particular separation handle are properly chosen, it is possible to discriminate between non-derivatized, monoderivatized and multiderivatized (e.g., bis-derivatized) polymers. Most of the separation handles used herein introduce hydrophobic properties to the polymer, as the preferred method for separation of the modified polymers is based on reverse-phase analytical and preparative chromatography. The choice of a proper separation handle comes from consideration of several practical aspects such as:

a) The hydrophobic separation handle can be removed from the polymer after purification in order to liberate the group reactive with a biologically active molecule and to avoid uncontrolled hydrophobic interactions within the conjugate—or more generally to avoid uncontrolled hydrophobic interactions during the interaction of the conjugate with the biological environment. This can preclude work with analogues of mPEG which contain a long hydrophobic alkyl ether chain instead of a methoxy group at one of the polymer termini. For the same reason, protection of an amino group as long chain fatty acid amides is not practical, as this group can be removed only under very extreme conditions.

b) As most of polymers and functional groups lack chromophoric properties, the chromatographic separation of polymers can be difficult. It is, therefore, advantageous if the separation handle introduces additionally some chromophore properties to the polymer. This can make protection of a terminal hydroxyl or thiol group by means of a long chain aliphatic fatty acid ester less interesting.

c) Chemical stability of the hydrophobic separation handle can be easy to control depending on an actual situation. This aspect is related mostly to the stability of other functional groups present in the derivatized polymer.

d) Chromatographic properties of the hydrophobic separation handle, and hence the properties of the derivatized polymer, can be easy to control by chemical modification of the hydrophobic separation handle.

e) Since even relatively stable phosphotriester bonds are slightly labile under high pH conditions, it can be preferred to avoid hydrophobic separation handles that can only be removed under such conditions.

Examples of hydrophobic separation handles that fulfill all these criteria belong to the group of acid labile protecting groups and are known as trityls, substituted trityls (e.g., monomethoxytrityl (MMTr), dimethoxytrityl (DMTr), trimethoxytrityl (TMTr), and p-bromophenacyloxytrityl (BPTr), pixyls and substituted pixyls (see, for example, U.S. Publication No. 2007/0276139). They are all acid labile, with distinct UV chromophore properties. Their acid stability can be easily controlled by the presence of different electron donating or electron withdrawing groups. Introduction of alkoxy chains of different length to the trityl structure is a convenient method for modification of their hydrophobic properties. Most of the Examples presented herein utilize, therefore, trityl groups both for protection of reactive functions and for introduction of an efficient separation handle. This should not be seen as a limitation of this disclosure, as other groups, even those which do not fulfill all the above criteria, may be useful in the present methodology as hydrophobic separation handles. Thus, a general description of a potential hydrophobic separation handle provided herein is: a hydrophobic group that withstands the presence of trivalent phosphorus present in a phosphoramidite or in an activated H-phosphonate, and which can also be employed for chromatographic resolution of modified polymer from the unmodified starting material.

With a few exceptions, there are few limits on the type and character of a functional group M. These exceptions appear in cases when the functional group is very sensitive to reducing conditions and becomes destroyed by the trivalent phosphoramidite group, with concomitant oxidation of phosphorus to the pentavalent oxidation state. The azido group is an example of such a reactive function that cannot be converted to the appropriate phosphoramidite. In fact, trivalent phosphorus of triphenylphosphine is used as an efficient reagent for conversion of an azido group to an amine. The activated dithio group, for example, as in a dithiopyridyl group, is another example that belongs to this category, although simple dithiols could be successfully converted to and delivered in the form of a phosphoramidites. Nevertheless, this disclosure presents also a variant of the above phosphoramidite method that omits the mentioned stability problem, and provides the ability to prepare polymers containing even an azido or activated dithio group.

This method is known as H-phosphonate methodology followed by oxidation of $P^{+3}$ by carbon tetrachloride/amine, and is similar to the phosphoramidite method in the sense that the incoming reagent contains reactive $P^{+3}$ phosphorus, and the phosphorus atom is oxidized during the reaction process to its pentavalent stage. The H-phosphonate methodology will be described in more detail later on in this text.

Many groups reactive with a biologically active molecule or a derivative thereof need to be protected in order to exist within the structure of phosphoramidite reagent. Examples include, without limitation, amino, aminoxy, hydrazo, hydroxyl, thio, certain fluorophores and carboxy groups. Some of these groups, like biotin, do not demand protection, but can be used in a protected form to obtain some additional effects. In some cases, trityl, substituted trityl, pixyl, and substituted pixyl can be used as protecting groups. One reason for this choice of a protecting group is the possibility for simultaneous introduction of a protecting group that also can be used as a hydrophobic separation handle in a reverse phase (RP) based chromatographic separation process. If separation is not demanded, like in the case where the polymer has only one reactive terminus (e.g., when using mPEG as a polymer backbone), and incorporation of a phosphoramidite may be forced to completion, any protecting group can be used for protection of the group reactive with a biologically active molecule. In particular, trifluoroacetamido and FMOC groups may be used for the protection of amino, aminoxy and hydrazo groups in such phosphoramidites.

The use of phosphoramidites containing a protected group, that when unprotected is reactive with a biologically active molecule or a derivative thereof, having a hydrophobic protecting group for derivatization of polymers has a clear advantage over other methods. For example, the starting polymer does not have to be partially protected in order to obtain pure, monofunctionalized polymers. The methods work with fully unblocked polymers and improved yield is obtained using an excess of such a non-expensive polymer (e.g., non-derivatized PEG) over the amidite. One value of this method is in the fact that the formed mixture consisting of mono-, bis-, or multi-derivatized polymers can be efficiently separated from each other.

Certain functional groups do not offer a straightforward possibility for introduction of a desired hydrophobic protecting group. To this group belong NETS-esters, most of the fluorophores, iodoacetamido and maleimido groups. Amidites containing these functional groups are not optimal for derivatization of diol-polymers, since the separation of the reaction mixtures can be impossible.

In some cases, polymer diols can be easily converted to certain monoprotected derivatives, and this protection can offer the possibility for using chromatography to obtain pure, temporarily blocked monoderivatized polymers. Even here the separation can be based on hydrophobic interactions between a hydrophobic support and a polymer derivatized with a hydrophobic protecting group acting as a hydrophobic separation handle. Examples of handles used for this purpose include, without limitation, substituted or unsubstituted tritylated hydroxyls, tritylated thiols, and tritylated amines. Introduction of a trityloxy or pixyloxy group onto the terminus of a polymer is straightforward as these polymers usually contain free hydroxyl groups. Introduction of a tritylthio group requires activation of the hydroxyl group by its conversion to a mesylate, tosylate, or by substitution with a halogen. In some cases, this last alternative can be used, as its implementation in the form of a Velsmeier reaction can be economically attractive. The activated polymer can then react with tritylmercaptan as described by Conolly and Rider in *Nucleic Acids Res.* 1985, 13, (12), 4485-4502. A polymer substituted with a thiol group also can be obtained by any of the other described methodologies, and then the thio group can be selectively tritylated in an acidic environment, utilizing the much higher affinity of the thio group over hydroxyl to carbocations. There are two ways to obtain polymers protected on one site with a tritylated amine group. A process is described for direct alkylation of tritylamine with alkyl halides so this method could be used directly in analogy to the above alkylation of tritylmercaptan. On the other hand any appropriate method for partial amination like alkylation of the phthalimide, alkylation of the trifluoracetamide or a Mitsunobu procedure can be applied for preparation of a monoamino polymer. This starting material, even in unpurified form, can be used for obtaining the tritylated amino polymer in a two-step process, starting with silylation of all free hydroxyls in a pyridine solution. All mentioned tritylated or pixylated polymers can be preoperatively purified by RP chromatography to isolate the pure monosubstituted polymer. The described earlier mono-protected polymer derivatives, made by reacting a polymer with a selected phosphoramidite, offer an interesting alternative as a mono-protected polymeric starting material for additional derivatization. Such a polymer can react next with a phosphoramidite to incorporate another functional group, so the final product can contain, for example, two separate phosphotriester linkages.

Monomethoxy PEG (mPEG), or generally monoalkylated polymers, can be used for the same purpose. Methoxy PEG's are used to guarantee monofunctionalization of a polymer. The problem is that such polymers can be contaminated by an unknown and variable amount of bis hydroxyl (diol) polymer. In the case of PEG the existence of the diol form is a consequence of moisture present during the polymerization of the ethyleneoxide, and this can be hard to avoid on an industrial scale. Even the slightest amount of water can result in formation of a hydroxyl anion—an undesired starting point of polymerization. Thus mPEG is not an optimal polymer for preparation of pure monofunctionalized polymers.

Once a polymer is properly monoprotected, however, its conversion to a reactive monofunctional derivative is straight-forward. Phosphoramidite chemistry allows incorporation of a reactive functionality with yield and speed that is beyond the competition of other chemical processes, including all sorts of hydroxyl alkylation reactions. Using the proper excess of these reagents, the reported yields exceed 98% for every step in a multistep process and are often nearly quantitative. In cases where only a single incorporation of a phosphoramidite takes place, this reaction can be expected to be quantitative.

There exists also an interesting alternative process to the described above functionalization following the previously described monoprotection. Groups reactive with a biologically active molecule or a derivative thereof that lack the possibility of carrying a hydrophobic separation handle can be incorporated into a trisubstituted unit having the reactive group of choice, the hydrophobic separation handle and the phosphoramidite group. There are several such units or molecules that can be used as carriers (scaffolds) for the construction of such trisubstituted block reagents. One of the simplest molecules, due to the ease of the chemical manipulations, is the uridine-based scaffold described by Hovinen and Hakala in *Organic Lett.* 2001, 3(16) 2473-2476, where R denotes a reactive group and L is an aliphatic linker to the uridine ring.

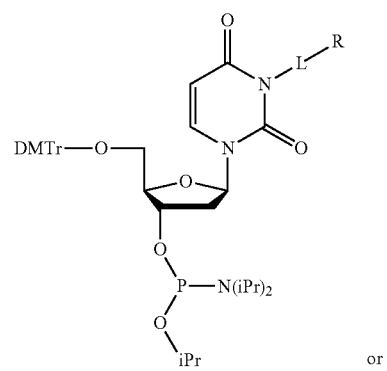

or

-continued

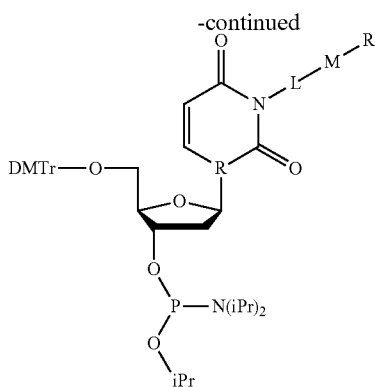

For instance, using reagents belonging to this category, it is possible to prepare, in a single reaction step, polymers covalently bonded to different fluorescent functionalities that can be isolated as a monosubstituted polymeric product.

The chemistry of phosphoramidites is mostly associated with the chemistry of nucleic acids. The very high demands of this multistep process require rather large excess of incoming amidites, and efficient catalysts. Examples of activators includes, without limitation, 1H-tetrazole, 5-(ethylthio)-1H-tetrazole (ETT), 5-(benzylthio)-1H-tetrazole (BTT), Activator 42 (5-(3,5-bis(trifluoromethyl)phenyl)-1H-tetrazole), and 4,5-dicyanoimidazole (DCI). Those are often expensive, and if applied to the synthesis of polymers, as in this disclosure, they would noticeably increase the price of the final reagent. However, as the chemistry in the present disclosure can have a single coupling step, and the quantitative yield of the reaction is not always necessary, it is possible to use other less expensive catalysts. The use of pyridinium hydrochloride or even buffered carboxylic acids for activation of phosphoramidites is described and proved, offering high reaction rate, albeit with minimally lower coupling yield.

The choice of an oxidizing reagent is another factor for consideration. Iodine is the simplest alternative, as this reagent can be prepared by dissolving iodine in a mixture of pyridine, tetrahydrofuran and water. Elemental sulfur can be used for phosphite oxidation combined with formation of sulfurized product, but it can be poorly soluble in organic solvents which can be used in the procedures described herein. Other, better soluble and more reactive reagents, like 3H-1,2-benzothiazol-3-one 1,1-dioxide (Beaucage reagent), phenylacetyl disulfide (PADS) or dimethylthiuram (DTD) were developed for this purpose. Thiophosphotriester linkages do not offer very much advantage over the normal phosphotriester linkages, as the latter can already be sufficiently stable, but may offer additional possibilities, e.g. the ability of chemical cleavage of this linkage. Peroxides exemplified by t-butyl hydrogen peroxide or m-chlorobenzoyl peroxide can be used as alternatives for $P^{+3}$ to $P^{+5}$ oxidations. They are colorless, can work under water-free conditions and are often applicable in situations where iodine promoted oxidations may lead to some unwanted side reactions.

It was mentioned earlier that groups reactive with a biologically active molecule which do not tolerate a coexistence with the phosphoramidite group can be attached to the polymer by H-phosphonate chemistry. This method takes advantage of the fact that $P^{+3}$ of the H-phosphonate is actually tetracoordinated, and as such this group can be more stable for oxidation than a phosphate triester or phosphoramidite. The particularly important point is that H-phosphonate does not interact with an azido group like most $P^{+3}$ containing compounds. The use of this methodology for incorporation of the azido group can be, however, combined with the incorporation of a useful hydrophobic separation handle allowing for discrimination between the product and unreacted starting material. Application of a trifunctional reagent, similar to the mentioned uridine derivative, but using a H-phosphonate instead of a phosphoramidite group, could be an alternative. In this case, the activation of the starting H-phosphonate reagent and its reaction with the polymer can be followed by addition of an excess of an appropriate alcohol (e.g., isopropanol) to convert the formed H-phosphonate diester to the desired H-phosphonate triester. The Examples below describe a slightly different procedure. Here, the procedure of introducing an azido group and a hydrophobic separation handle has been divided into two steps, instead of making it in a single step, using a trifunctional reagent. This is not an optimal approach, but it was possible due to very high yield of each reaction. Polymer was first reacted with H-phosphonate of tritylated diethyleneglycol. It is important to use a starting glycol containing more than two carbons; otherwise, the free OH group in the final product, after removal of the trityl group, may destabilize the phosphotriester linkage. Oxidation of $P^{-3}$ to $P^{+5}$ was combined with the introduction of the azido group into the polymer, and it was done according to the described $CCl_4$/pyridine/amine procedure, using 1-amino-6-azido-hexane as a source of the azido group. The opposite order of incorporation of reactive groups using H-phosphonate chemistry is also feasible. It is also recognized that H-phosphonate chemistry could be applied for the incorporation of any of existing reactive groups, if other factors of interest like hydrolytic stability of the starting reagents, or costs of syntheses, are deciding.

Conjugates

This document also provides conjugates that include a functionalized polymer as provided herein and a biologically active molecule.

In some embodiments, a biologically active molecule is a TNF inhibitor or a derivative thereof. As used herein, the term "TNF inhibitor" includes antibodies or fusion proteins that bind to TNF alpha (e.g, human TNF alpha). Non-limiting examples of include etanercept (Enbrel®, Amgen and Pfizer); infliximab (Remicade®, Janssen Biotech, Inc.); adalimumab (Humira®, Abbott Laboratories); certolizumab pegol (Cimzia®); and Golimumab (Simponi®, Janssen Biotech, Inc.).

In some embodiments, a biologically active moleculs is insulin or a derivative thereof. Derivatives of insulin include, for example, insulin analogs that contain one or more amino acid substitutions, and modifications to insulin or insulin analogs to include, for example, a moiety reactive with M or R on the polymer (as described above for compounds (1), (2), and (3)). Insulin and analogs can be recombinantly produced (e.g., in a non-pathogenic organism). Non-limiting examples of suitable insulin analogs include insulin lispro (HUMALOG, sold by Eli Lilly), insulin aspart ("NovoLog/NovoRapid" sold by Novo Nordisk), insulin detemir (Levemir® sold by Novo Nordisk), Insulin glargine (Lantus®, sold by Sanofi-Aventis), and insulin glulisine (Apidra®, sold by Sanofi-Aventis).

Insulin lispro is a rapid-acting human insulin analog used to lower blood glucose levels, and contains a substitution of lysine for proline at position B28, and a substitution of proline for lysine at position B29.

Insulin aspart is a rapid-acting human insulin analog used to lower blood glucose levels, and contains a substitution of an aspartic acid for proline at position B28.

Insulin detemir is a long-acting insulin analog used for maintaining the basal level of insulin. Insulin determir contains myristic acid is bound to the lysine at position B29.

Insulin glargine is a long-acting insulin analog used for lower blood glucose, and contains a substitution of a glycine for asparagine at position A21 and contains two arginines added to the C-terminus of the B-chain.

Insulin glulisine is a rapid acting human insulin analog used to lower blood glucose levels, and contains a substitution of a lysine for asparagine at position B3 and the substitution of a glutamic acid for lysine at position B29.

In some embodiments, a biologically active molecule is omalizumab or a derivative thereof. Omalizumab is sold under the trade name Xolair (Novartis Pharmaceuticals, East Hanover, N.J.; Genentech Inc., South San Francisco, Calif.), and is a recombinant humanized monoclonal antibody having a molecular weight of approximately 150,000 Da. See Substance Identifier 47206967. See also U.S. Pat. No. 6,267,958.

"Antibody" as the term is used herein refers to a protein that generally comprises heavy chain polypeptides and light chain polypeptides. Antigen recognition and binding occurs within the variable regions of the heavy and light chains. Single domain antibodies having one heavy chain and one light chain and heavy chain antibodies devoid of light chains are also known. A given antibody comprises one of five types of heavy chains, called alpha, delta, epsilon, gamma and mu, the categorization of which is based on the amino acid sequence of the heavy chain constant region. These different types of heavy chains give rise to five classes of antibodies, IgA (including IgA1 and IgA2), IgD, IgE, IgG (IgG1, IgG2, IgG3 and IgG4) and IgM, respectively. A given antibody also comprises one of two types of light chains, called kappa or lambda, the categorization of which is based on the amino acid sequence of the light chain constant domains. Omalizumab is an IgG1 antibody and contains kappa chains. IgG antibodies generally contain two identical heavy chains and two identical light chains and two antigen combining domains, each composed of a heavy chain variable region ($V_H$) and a light chain variable region ($V_L$).

"Humanized antibody" refers to an antibody that has been engineered to comprise one or more human framework regions in the variable region together with non-human (e.g., mouse, rat, or hamster) complementarity-determining regions (CDRs) of the heavy and/or light chain. In some embodiments, a humanized antibody comprises sequences that are entirely human except for the CDR regions. Humanized antibodies are typically less immunogenic to humans, relative to non-humanized antibodies, and thus offer therapeutic benefits in certain situations. For Omalizumab, the CDRs are derived from the parent murine monoclonal antibody and the constant regions of Omalizumab are derived from $IgG_1$.

Derivatives of Omalizumab include, for example, modifications to Omalizuabinsulin or insulin analogs to include, for example, a moiety reactive with M or R on the polymer (as described above for compounds (1), (2), and (3)) or a fragment of Omalizumab. A fragment of Omalizumab refers to a polypeptide derived from the heavy or light chain of Omalizumab that lacks all of part of at least one chain of Omalizumab. As the term is used herein encompasses fragments that comprise single polypeptide chains derived from antibody polypeptides (e.g., a heavy or light chain antibody polypeptide), it will be understood that an antibody fragment may not, on its own, bind an antigen. For example, an antibody fragment may comprise that portion of a heavy chain antibody polypeptide that would be contained in a Fab fragment; such an antibody fragment most commonly will not bind an antigen unless it associates with another antibody fragment derived from a light chain antibody polypeptide (e.g., that portion of a light chain antibody polypeptide that would be contained in a Fab fragment) and reconstitutes the antigen-binding site. Non-limiting examples of antibody fragments can include, for example, polypeptides that would be contained in Fab fragments, F(ab')2 fragments, or scFv (single chain Fv) fragments.

In some embodiments, a biologically active molecule is a clotting factor or a derivative thereof. Derivatives of a clotting factor include, for example, a clotting factor analog that contains one or more amino acid substitutions relative to the corresponding human clotting factor, and modifications to the clotting factor or clotting factor analog to include, for example, a moiety reactive with M or R on the polymer (as described above for compounds (1), (2), and (3)). Clotting factors and analog thereof s can be recombinantly produced (e.g., in a non-pathogenic organism).

In some embodiments, a polypeptide that boosts red or white blood cell production. Examples of polypeptides that boost red blood cell production include epoetin alpha (Epogen®, Amgen), epoetin beta (NeoRecormon®, Roche), epoetin theta (Eporatio®), epoetin zeta and darbepoetin alpha (Aranesp®, Amgen)). Examples of polypeptides that boost white blood cell production include filgrastim (e.g., Neupogen®). Such polypeptides can be recombinantly produced. Derivatives of a polypeptide that boosts red or white blood cell production include, for example, an analog that contains one or more amino acid substitutions relative to the corresponding human polypeptide, and modifications to the polypeptide or analog to include, for example, a moiety reactive with M or R on the polymer (as described above for compounds (1), (2), and (3)).

This document also provides conjugates that include a functionalized polymer as provided herein and a biologically active molecule such as an antibody or a derivative thereof. Non-limiting examples of antibodies that can be conjugated to a functionalized polymer include, abatacept (Orencia®), alemtuzumab (marketed as Campath, MabCampath or Campath-1H); basiliximab (Simulect®), belimumab (Benlysta®), besilesomab (Scintimun®), bevacizumab (Avastin®), canakinumab (Ilaris®), catumaxomab (Removab®), cetuximab (Erbitux®), denosumab (Prolia®, Xgeva®), eculizumab (Soliris®), ipilimumab (also known as MDX-010 or MDX-101, Yervoy®), natalizumab (Tysabri®), ofatumumab (Arzerra®), palivizumab (Synagis®), panitumumab (Vectibix®), ranibizumab (Lucentis®), rituximab (Rituxan®, MabThera®), tocilizumab (Actemra®, RoActemra®), trastuzumab (Herceptin®), and ustekinumab (Stelara®).

Abatacept is sold under the trade name Orencia® by Bristol-Myers Squibb Company, and is a fusion protein of the Fc region of IgG1 fused to the extracellular domain of CTLA-4. It is a selective T cell costimulation modulator indicated for the treatment of adult rheumatoid arthritis and for juvenile idiopathic arthritis (JIA) in pediatric patients six years of age and older.

Alemtuzumab is sold under the trade name Campath®, MabCampath®, or Campath-1H® by Genzyme. Alemtuzumab is a recombinant DNA-derived humanized monoclonal antibody that is directed against the 21-28 kD cell surface glycoprotein, CD52. It is an IgG1 kappa antibody with human variable framework and constant regions, and complementarity-determining regions from a murine (rat) monoclonal antibody (Campath-1G). Campath is produced in mammalian cell (Chinese hamster ovary) suspension culture in a medium containing neomycin, and is used in the treatment of chronic lymphocytic leukemia (CLL), cutaneous T-cell lymphoma (CTCL) and T-cell lymphoma. It is also used in some conditioning regimens for bone marrow transplantation, kidney transplantation and islet cell transplantation.

Basiliximab is sold under the trade name Simulect® by Novartis Pharmaceuticals. It is a chimeric mouse-human monoclonal antibody to the α chain (CD25) of the IL-2 receptor of T cells. It is used to prevent rejection in organ transplantation, especially in kidney transplants.

Belimumab is sold under the trade name Benlysta® (Human Genome Sciences, Inc. and The GlaxoSmithKline Group of Companies). It is a monoclonal antibody that inhibits Beta cell activating factor (BAFF), and is used to treat adults with active systemic lupus erythematosus (SLE or lupus).

Besilesomab is sold under the trade name Scintimun® (CiS Bio International). It is a mouse monoclonal antibody labeled with the radioactive isotope technetium-99m. It is used to detect inflammatory lesions and metastases. It binds to $IgG_1$.

Bevacizumab is sold under the trade name Avastin® by Genentech/Roche. It is a humanized monoclonal antibody that inhibits VEGF-A and slows angiogenesis. It is used to treat various cancers, including colorectal, lung, breast, glioblastoma, kidney, and ovarian cancer.

Canakinumab is sold under the trade name Ilaris® by Novartis. It is a human monoclonal antibody targeted at interleukin-1 beta. It has no cross-reactivity with other members of the interleukin-1 family, including interleukin-1 alpha. Canakinumab is used to treat autoinflammatory syndromes including familial cold autoinflammatory syndrome, Muckle-Wells syndrome, and neonatal-onset multisystem inflammatory disease.

Catumaxomab is sold under the trade name Removab® by TRION Pharma GmbH. It is a rat-mouse hybrid monoclonal antibody that is used to treat malignant ascites, which typically occurs in patients with metastasizing cancer. Catumaxomab has two binding specificities directed at epithelial cell adhesion molecule (EpCAM) and the T-cell antigen CD3. See Sebastian et al., *Drugs Today* (Barc). 45(8):589-97 (2009).

Cetuximab is sold under the trade name Erbitux® by Bristol-Myers Squibb and Eli Lilly and Company. It is a chimeric (mouse/human) monoclonal antibody that binds to the epidermal growth factor receptor (EGFR) and acts as an inhibitor. Cetuximab can be used for treatment of metastatic colorectal cancer and head and neck cancer.

Denosumab is sold under the trade name Prolia® and Xgeva® by Amgen. It is a fully human monoclonal antibody that targets RANKL (RANK ligand), a protein that acts as the primary signal for bone removal, and is used for the treatment of osteoporosis, treatment-induced bone loss, bone metastases, rheumatoid arthritis, multiple myeloma, and giant cell tumor of bone.

Eculizumab is sold under the trade name Soliris® by Alexion Pharmaceuticals. It is a recombinant humanized monoclonal antibody that contains human constant regions from human $IgG_2$ sequences and human $IgG_4$ sequences and murine complementarity-determining regions grafted onto the human framework light- and heavy-chain variable regions. Eculizumab is composed of two 448 amino acid heavy chains and two 214 amino acid light chains and has a molecular weight of approximately 148 kDa. Eculizumab specifically binds the complement protein C5. Eculizumab has been shown to be effective in treating paroxysmal nocturnal hemoglobinuria (PNH), a rare and sometimes life threatening disease of the blood. Binding of Eculizumab to C5 inhibits its cleavage by the C5 convertase, and prevents the generation of the terminal complement complex C5b-9. It is this terminal complement complex that causes intravascular hemolysis in people with PNH.

Ipilimumab (also known as MDX-010 or MDX-101) is sold under the trade name Yervoy® by Bristol-Myers Squibb. It is a fully human monoclonal antibody that binds to CTLA-4 (cytotoxic T lymphocyte-associated antigen 4), and is used to treat melanoma (e.g., metastatic melanoma or unresectable melanoma).

Natalizumab is sold under the trade name Tysabri® by Biogen Idec and Élan. It is a humanized monoclonal antibody against the cell adhesion molecule α4-integrin. Natalizumab is used in the treatment of multiple sclerosis and Crohn's disease.

Ofatumumab is sold under the trade name Arzerra® by Genmab. It is a human monoclonal antibody that specifically binds the CD20 protein and inhibits early-stage B lymphocyte activation. Ofatumumab is used for treating chronic lymphocytic leukemia, follicular non-Hodgkin's lymphoma, diffuse large B cell lymphoma, rheumatoid arthritis, and relapsing remitting multiple sclerosis.

Palivizumab is sold under the trade name Synagis® by MedImmune. It is a humanized monoclonal antibody ($IgG_1$ kappa) directed against an epitope in the A antigenic site of the F protein of RSV. Palivizumab is a composite of human (95%) and murine (5%) antibody sequences.

Panitumumab is sold under the trade name Vectibix® by Amgen. It is a fully human monoclonal antibody specific to the epidermal growth factor receptor (also known as EGF receptor, EGFR, ErbB-1 and HER1 in humans), and is used to treat metastatic colorectal cancer.

Ranibizumab is sold under the trade name Lucentis® by Novartis. It is a monoclonal antibody fragment (Fab) derived from the same parent mouse antibody as bevacizumab and targets VEGF-A. Ranibizumab is an anti-angiogenic and can be used to treat age-related macular degeneration (e.g., AMD and ARMD).

Rituximab is sold under the trade names Rituxan® and MabThera® by Biogen Idec and Genentech. It is a chimeric monoclonal antibody against the protein CD20, which is primarily found on the surface of B cells. Rituximab can be used to treat lymphomas, leukemias, transplant rejection and some autoimmune disorders.

Tocilizumab is sold under the trade names Actemra® and RoActemra® by Hoffmann-La Roche and Chugai. It is a humanized monoclonal antibody that binds the interleukin-6 receptor (IL-6R) and is used as an immunosuppressive to treat rheumatoid arthritis (RA) and systemic juvenile idiopathic arthritis.

Trastuzumab is sold under the trade name Herceptin® by Genentech. It is a humanized monoclonal antibody that binds domain IV of the extracellular segment of the HER2/neu receptor. It typically is used to treat breast cancer.

Ustekinumab is sold under the trade name Stelara® by Centocor. It is human monoclonal antibody that is directed against interleukin 12 and interleukin 23, and is used to treat psoriasis.

In certain embodiments, "Chimeric antibody" as the term is used herein refers to an antibody that has been engineered to comprise a human constant region. Chimeric antibodies are typically less immunogenic to humans, relative to non-chimeric antibodies, and thus offer therapeutic benefits in certain situations.

Derivatives of an antibody include, for example, modifications to the antibody to include, for example, a moiety reactive with M or R on the polymer (as described above for compounds (1), (2), and (3)) or a fragment of the antibody. A fragment of the antibody refers to a polypeptide derived from the heavy or light chain of the antibody that lacks all of part of at least one chain of the antibody. As the term as used herein encompasses fragments that comprise single polypeptide chains derived from antibody polypeptides (e.g., a heavy or light chain antibody polypeptide), it will be understood that an antibody fragment may not, on its own, bind an antigen. For example, an antibody fragment may comprise that portion of a heavy chain antibody polypeptide that would be contained in a Fab fragment; such an antibody fragment most commonly will not bind an antigen unless it associates with another antibody fragment derived from a light chain antibody polypeptide (e.g., that portion of a light chain antibody polypeptide that would be contained in a Fab fragment) and reconstitutes the antigen-binding site. Non-limiting examples of antibody fragments can include, for example, polypeptides that would be contained in Fab fragments, F(ab')2 fragments, or scFv (single chain Fv) fragments.

This document also provides conjugates that include a functionalized polymer as provided herein and a biologically active molecule such as therapeutic agents, small molecules such as synthetic drugs, oligo- and polypeptides, oligonucleotides, coding DNA sequences, antisense DNA sequences, mRNAs, antisense RNA sequences, RNAIs, and siRNAs, carbohydrates, lipids, growth factors, enzymes, transcription factors, toxins, antigenic peptides (as for vaccines), antibodies, and antibody fragments. For example, a biologically active molecule can be agalsidase alfa (Replagal®), agalsidase beta (Fabrazyme®), alglucosidase alfa (Myozyme®), anakinra (Kineret®), bortezomib (Velcade®), conestat alfa (Ruconest®), choriogonadotropin alfa (e.g., Ovidrel®), cinacalcet (Sensipar®), Corifollitropin alfa (Elonva®), dibotermin alfa (InductOs®), eltrombopag (Promacta®), eptotermin alfa (Osigraft®), erlotinib (Tarceva®), follitropin alfa/lutropin alfa, follitropin beta, galsulfase (Naglazyme®), Gefitinib (Iressa®), Human normal immunoglobulin, human normal immunoglobulin (ivig), human normal immunoglobulin (SCIg), idursulfase (Elaprase®), Imiglucerase (Cerezyme®), interferon alfa-2b, interferon beta-1a, interferon beta-1b, Lapatinib (Tykerb®, Tyverb®), Laronidase (Aldurazyme®), Pazopanib (Votrient), pegaptanib, pegfilgrastim, peginterferon alfa-2b, Rasburicase (Elitek®), Reteplase (Retavase®), Somatropin, Sorafenib (Nexavar®), Tenecteplase (TNKase), thyrotropin alfa, Vandetanib (Caprelsa®), and Vemurafenib (Zelboraf®).

Agalsidase alfa and Agalsidase beta (Fabrazyme®) are recombinant human α-galactosidase A enzymes, and can be used for long-term enzyme replacement therapy in patients with Fabry's disease, which is caused by the lack of alpha-galactosidase A.

Aglucosidase alfa is recombinant alpha glucoside, and can be used for enzyme replacement therapy in patients with Pompe's disease.

Anakinra (Kineret®) is an interleukin 1 receptor antagonist, and can be used to reduce the pain and swelling associated with rheumatoid arthritis.

Bortezomib (Velcade®) is an N-protected dipeptide used to treat people with multiple myeloma Conestat alfa is a recombinant human C1 obtained from the milk of transgenic rabbits. It can be used to treat hereditary angioneurotic edema.

Choriogonadotropin alfa (Ovidrel®) is human chorionic gonadotropin (HCG), and can be used to help produce mature eggs during in vitro fertilization and stimulate ovulation (release of an egg).

Cinacalcet is a calcimimetic agent that increases the sensitivity of the calcium-sensing receptor to activation by extracellular calciumcinacalcet. See e.g., U.S. Pat. No. 6,211,244. It can be used to treat secondary hyperparathyroidism.

Corifollitropin alfa (Elonva®) is a modified follicle stimulating hormone (FSH), and can be used to stimulate egg production during infertility treatments.

Dibotermin alfa (InductOs®) is recombinant human bone morphogenetic protein 2 and can be used to promote new bone formation and for the treatment of bony defects.

Eltrombopag (Promacta®) is a small molecule agonist of the c-mpl (TpoR) receptor, and is used to increase the number of platelets (cells that help the blood clot) in order to decrease the risk of bleeding in people who have chronic idiopathic thrombocytopenic purpura.

Eptotermin alfa (Osigraft®) is recombinant human bone morphogenetic protein 7 (hrBMP-7) (also referred to as Osteogenic protein-1 (OP-1)) and is used to aid healing of bone.

Erlotinib (Tarceva®) is a reversible tyrosine kinase inhibitor that acts on the epidermal growth factor receptor (EGFR). It is used for treatment of nonsmall cell lung cancer and pancreatic cancer (in combination with gemcitabine).

Follitropin alfa/lutropin alfa contains a recombinant follicle stimulating hormone (FSH) and recombinant luteinizing hormone (LH). Follitropin beta is another recombinant FSH.

Galsulfase is a recombinant form of human N-acetylgalactosamine 4-sulfatase (Naglazyme®; BioMarin) and is used for treatment of mucopolysaccharidosis type VI Gefitinib (Iressa®) is an EGFR inhibitor that is used for treatment of cancer (e.g., nonsmall cell lung cancer).

Idursulfase (Elaprase®) is the recombinant lysosomal enzyme iduronate-2-sulfatase, and is used to treat Hunter syndrome (Mucopolysaccharoidosis II)).

Imiglucerase (Cerezyme®) is a recombinant analog of human β-glucocerebrosidase, and is used to treat Gaucher's disease.

Lapatinib (Tykerb®, Tyverb®) is a dual tyrosine kinase inhibitor that interrupts the $HER_2$ growth receptor pathway, and is used to treat breast cancer.

Laronidase (Aldurazyme®) is a recombinant polymorphic variant of the human enzyme α-L-iduronidase enzyme, and is used to treat mucopolysaccharoidosis.

Pazopanib (Votrient) is a potent and selective multi-targeted receptor tyrosine kinase inhibitor of VEGFR-1, VEGFR-2, VEGFR-3, PDGFR-α/β, and c-kit that blocks tumor growth and inhibits angiogenesis.

Rasburicase (Elitek®) is a recombinant version of urate oxidase, an enzyme which occurs in many mammals but not in humans. It can be used to treat hyperuricemia in patients after cancer treatment.

Reteplase (Retavase®) is a recombinant non-glycosylated form of human tissue plasminogen activator, which has been modified to contain 357 of the 527 amino acids of the original protein. It is a thrombolytic drug and used to treat heart attacks.

Rilonacept (Arcalyst®) is a dimeric fusion protein consisting of the extracellular domain of human interleukin-1 receptor and the FC domain of human IgG1 that binds and neutralizes IL-1. It can be used to treat gout.

Sorafenib (Nexavar®) is a small molecular inhibitor of several tyrosine protein kinases (VEGFR and PDGFR) and Raf kinases. It can be used to treat renal cell carcinoma and liver cancer.

Tenecteplase (TNKase) is a recombinant tissue plasminogen activator analog, and is used as a thrombolytic drug.

Vandetanib (Caprelsa®) is an an antagonist of the vascular endothelial growth factor receptor (VEGFR) and the epidermal growth factor receptor (EGFR), and can be used to treatment of thyroid cancer.

Vemurafenib (Zelboraf®) is a B-Raf enzyme inhibitor and used for treatment of melanoma.

Numerous other examples of biologically active molecules will be apparent to the skilled artisan.

Derivatives of a biologicaly active molecule include modifications to the biologically active molecule to include, for example, a moiety reactive with M or R on the polymer (as described above for compounds (1), (2), and (3))

Preparation of conjugates between a functionalized polymer provided herein and a biologically active molecule or a derivative thereof occurs through a coupling reaction between the reactive group on the polymer with a biologically active molecule or derivative thereof. One of skill in the art would appreciate that there are many ways to couple a biologically active molecule or a derivative thereof with the functional polymers described herein. For example, a biologically active molecule can be modified to introduce thiols at the places of reactive amino groups (e.g., at lysine residues) that can subsequently react with a maleimido or iodoacetamido-group activated functionalized polymer described herein.

A biologically active molecule also can be derivatized to incorporate hydrazo functions that can subsequently react with an aldehyde/keto functionalized polymer described herein.

In another method, a biologically active molecule is reacted with a reagent that introduces an azido function at amino groups. The resulting azido modified biologically active molecule (e.g., antibody, polypeptide) then can be further reacted with an alkyne-derivatized functionalized polymer to obtain a conjugate via the Click-reaction.

In another method, a biologically active molecule can be reacted with a reagent introducing a diene/dienophile that can subsequently react with a diene/dienophile activated functionalized polymer described herein to produce a conjugate after the Diels-Alder reaction.

In another method, the functionalized polymer is directly linked to a biologically active molecule or a derivative thereof. For example, a functional polymer (e.g., PEG) containing a carboxyl group that is previously activated by a reactive ester group like N-hydroxysuccinimide (NHS) can be conjugated to a biologically active molecule or a derivative thereof.

Generally, a functionalized polymer described herein can include an activated ester as M-R, and can react randomly with protein amino groups (e.g., lysines) to form covalent linkages. Many activating groups are available commercially as a wide variety of leaving groups are known. Non-limiting examples of leaving groups include p-nitrophenol and NHS. Attaching of PEGs to antibodies is often made randomly because the IgG molecule often demands several polymers to be efficiently protected.

In another method, aldehyde-containing functionalized polmers can form a Schiff's base with amino groups on the protein. The Schiff's base is further selectively reduced with sodium cyanoborohydride in a well known reaction.

In another method, periodate can be used to oxidize carbohydrates on a biologically active molecule to aldehydes, followed by addition of hydrazo derivatized PEG to be attached. The hydrazo group reacts with the aldehydes to produce a stable hydrazide link.

In one embodiment, a biologically active molecule conjugate, or a pharmaceutically acceptable salt thereof includes a water-soluble, non-peptidic, and non-nucleotidic polymer backbone as in a structure of formula (9):

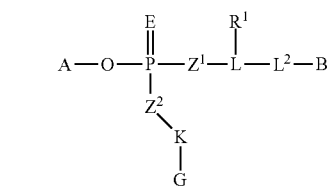

or a salt thereof,
wherein:
A is the point of covalent bonding to one terminus of the polymer backbone; E is O or S; K is selected from the group consisting of: alkylene, alkyleneoxyalkylene, and oligomeric alkyleneoxyalkylene; G is selected from the group consisting of: hydrogen, alkoxy, and a hydrophobic separation handle; $Z^1$ and $Z^2$ are independently selected from O and NH, wherein only one of $Z^1$ and $Z^2$ can be NH; L is selected from the group consisting of: a divalent radical of a nucleoside, alkylene, alkyleneoxyalkylene, oligomeric alkyleneoxyalkylene, and unsubstituted and substituted arylene; $R^1$ is absent or a hydrophobic separation handle, wherein only one of $R^1$ and G can be a hydrophobic separation handle; $L^2$ is a covalent linking moiety between L on the polymer backbone and B (e.g., amide, carbamide, ester, oxime, thioether, dithioether, secondary amine, 1,2,4-triazol, or hydrazide linking moiety); and B is a biologically active molecule or a derivative thereof.

Such a conjugate can be prepared by reacting a biologically active molecule or a derivative thereof with a preparation comprising a water-soluble, non-peptidic, and non-nucleotidic polymer backbone having at least one terminus covalently bonded to a structure of formula (1) (as described above) under conditions suitable for group M to react with a biologically active molecule or the derivative thereof. The group M can be hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, or iodoacetamide. In some embodiments, the group reactive with a biologically active molecule or derivative thereof is carboxyl and R is absent or is N-hydroxysuccinimidyl, p-nitrophenyl, or pentachlorophenyl.

In one embodiment, a conjugate, or a pharmaceutically acceptable salt thereof, has a structure of formula (10):

(10)

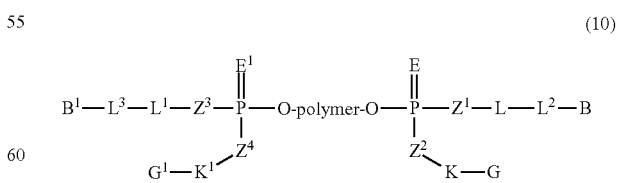

or a salt form thereof,
wherein polymer has a linear, water-soluble, non-peptidic, and non-nucleotidic polymer backbone (e.g., PEG), wherein each linking group is bonded at a different terminus of the polymer; E and $E^1$ are independently O or S; K and $K_1$ are independently selected from the group consisting of: alkylene, alkyleneoxyalkylene, and oligomeric alkyleneoxyalkylene; G and $G_1$ are independently absent or are selected from the group consisting of: alkoxy and a hydrophobic separation handle; each pair of $Z^1$ and $Z^2$ and $Z^3$ and $Z^4$ are independently selected from O and NH, wherein only one of each pair of $Z^1$ and $Z^2$ and $Z^3$ and $Z^4$ can be NH; L and $L^1$ are independently selected from the group consisting of: a divalent radical of a nucleoside, alkylene, alkyleneoxyalkylene, oligomeric alkyleneoxyalkylene, and unsubstituted and substituted arylene; $L^2$ is a covalent linking moiety (e.g., amide, carbamide, ester, oxime, thioether, dithioether, secondary amine, 1,2,4-triazol, or hydrazide linking moiety); between L on the polymer backbone and B; $L^3$ is a covalent linking moiety (e.g., amide, carbamide, ester, oxime, thioether, dithioether, secondary amine, 1,2,4-triazol, or hydrazide linking moiety) between L on the polymer backbone and $B^1$; and B and $B^1$ are independently a biologically active molecule or a derivative of a biologically active molecule (e.g., a TNF inhibitor, a derivative of a TNF inhibitor, insulin, a derivative of insulin a clotting factor, a derivative of a clotting factor, omalizumab, a derivative of malizumab, a polypeptide that boosts red or white cell production, or a derivative of a polypeptide that boosts red or white cell product, an antibody, or a derivative of an antibody), a biologic other than the biologically active molecule (e.g., an antibody or a polypeptide other than the biologically active molecule), a drug, a detectable group, or a separation moiety, wherein at least one of B and $B^1$ is a biologically active molecule or a derivative of a biologically active molecule. For example, B can be selected from the group consisting of a TNF inhibitor, insulin, omalizumab, a clotting factor, a polypeptide that boosts red or white cell production, or an antibody; and $B^1$ can be a derivative of a biologically active molecule selected from the group group consisting of a TNF inhibitor, insulin, omalizumab, a clotting factor, a polypeptide that boosts red or white cell production, and an antibody; B and $B^1$ can both be a biologically active molecule; one of B and $B^1$ is a biologically active molecule and the other is a separation moiety; one of B and $B^1$ is a biologically active molecule and the other is a different biologic; one of B and $B^1$ is a biologically active molecule and the other is a detectable group; or one of B and $B^1$ is a biologically active molecule and the other is a drug.

Such a conjugate can be prepared by reacting a biologically active molecule or a derivative thereof with a preparation comprising a compound of formula (2) (as described above) under conditions suitable for group M to react with a biologically active molecule or the derivative thereof. The group M can be hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, or iodoacetamide. In some embodiments, the group reactive with a biologically active molecule or derivative thereof is carboxyl and R is absent or is N-hydroxysuccinimidyl, p-nitrophenyl, or pentachlorophenyl.

In one embodiment, a conjugate, or a pharmaceutically acceptable salt thereof, has a structure of formula (11):

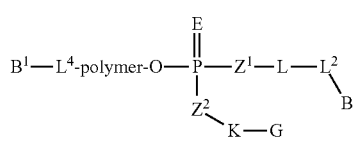

(11)

or a salt form thereof, wherein polymer is a linear, water-soluble, non-peptidic, and non-nucleotidic polymer backbone (e.g., a PEG polymer), wherein $M^2$ and the phosphonate-derived functional group are bonded at a different terminus of said polymer; E and $E^1$ are independently O or S; K is selected from the group consisting of: alkylene, alkyleneoxyalkylene, and oligomeric alkyleneoxyalkylene; G is selected from the group consisting of: hydrogen, alkoxy, and a hydrophobic separation handle; $Z^1$ and $Z^2$ are independently selected from O and NH, wherein only one of $Z^1$ and $Z^2$ can be NH; L is selected from the group consisting of: a divalent radical of nucleoside, alkylene, alkyleneoxyalkylene, oligomeric alkyleneoxyalkylene, and unsubstituted and substituted arylene; $L^2$ is a covalent linking moiety (e.g., amide, carbamide, ester, oxime, thioether, dithioether, secondary amine, 1,2,4-triazol, or hydrazide linking moiety); between L on the polymer backbone and B; $L^4$ is a covalent linking moiety (e.g., amide, carbamide, ester, oxime, thioether, dithioether, secondary amine, 1,2,4-triazol, or hydrazide linking moiety); between L on the polymer backbone and $B^1$; and B and $B^1$ are independently a biologically active molecule or a derivative of a biologically active molecule (e.g., a TNF inhibitor, a derivative of a TNF inhibitor, insulin, a derivative of insulin, omalizumab, a derivative of omalizumab, a clotting factor, a derivative of a clotting factor, a polypeptide that boosts red or white cell production, a derivative of a polypeptide that boosts red or white cell production, an antibody, or a derivative of an antibody), a biologic other than a biologically active molecule, a drug, a detectable group, a separation moiety, wherein at least one of B and $B^1$ is a biologically active molecule or a derivative of a biologically active molecule. For example, B can be a biologically active molecule and $B^1$ can be a derivative of a biologically active molecule; B and $B^1$ can both be a biologically active molecule; one of B and $B^1$ is a biologically active molecule and the other is a separation moiety; one of B and $B^1$ is a biologically active molecule and the other is a different biologic; one of B and $B^1$ is a biologically active molecule and the other is a detectable group; or one of B and B1 is a biologically active molecule and the other is a drug.

Preparations

Also provided herein are preparations that include a compound or conjugate provided herein. In some embodiments, a preparation can include at least 50% of a compound or conjugate by weight. For example, a preparation can include at least 60%, at least 65%, at least 70%, at least 75% at least 77%, at least 80%, at least 85%, at least 87%, at least 89%, at least 90%, at least 92%, at least 94%, at least 95%, at least 96%, at least 97%, at least 98%, and at least 99% by weight of the compound or conjugate. In some embodiments, the compound or conjugate is essentially pure in the preparation.

A preparation can be a solution, a reaction mixture, a chromatographic eluent, a solid (e.g., a power or crystalline form of the preparation), or any other mixture that includes a compound or conjugate in the appropriate amount or level or purity.

Pharmaceutically Acceptable Salts and Compositions

This document also provides pharmaceutically acceptable salts of the compounds and conjugates provided herein. Examples of pharmaceutically acceptable salts of a compound or a conjugate provided herein include acid addition salts and base salts of the same.

Suitable acid addition salts are formed from acids which form non-toxic salts. Examples include, without limitation, the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, oxalate, palmitate, pamoate, phosphate/hydrogen, phosphate/phosphate dihydrogen, pyroglutamate, saccharate, stearate, succinate, tannate, D- and L-tartrate, 1-hydroxy-2-naphthoate tosylate, and xinafoate salts.

Suitable base salts are formed from bases which form non-toxic salts. Examples include, without limitation, the aluminium, arginine, benzathine, calcium, choline, diethylamine, diolamine, glycine, lysine, magnesium, meglumine, olamine, potassium, sodium, tromethamine, and zinc salts.

Hemisalts of acids and bases may also be formed, for example, hemisulphate and hemicalcium salts.

A conjugate, as provided herein, can be formulated into a pharmaceutical composition that includes an effective amount of a conjugate and a pharmaceutically acceptable excipient. Also provided herein are pharmaceutical compositions that include an effective amount of a compound as provided herein, wherein M is a detectable functional group, and a pharmaceutically acceptable excipient.

Non-limiting examples of pharmaceutical excipients suitable for administration of the conjugates and compounds provided herein include any such carriers known to those skilled in the art to be suitable for the particular mode of administration. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of a compound or conjugate provided herein. In some embodiments, the excipient is a physiologically acceptable saline solution.

A pharmaceutical composition can be, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal ointments, creams, gels, and patch preparations and dry powder inhalers (see, e.g., *Ansel Introduction to Pharmaceutical Dosage Forms, Fourth Edition* 1985, 126).

The concentration of a compound or conjugate in a pharmaceutical composition will depend on absorption, inactivation, and excretion rates of the compound or conjugate, the physicochemical characteristics of the compound or conjugate, the dosage schedule, and amount administered as well as other factors known to those of skill in the art.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or conjugates. The pharmaceutically therapeutically active compounds or conjugates are, in one embodiment, formulated and administered in unit-dosage forms or multiple-dosage forms. Unit-dose forms as used herein refer to physically discrete units suitable for human and animal patients and packaged individually as is known in the art. Each unit-dose contains a predetermined quantity of the therapeutically active compound or conjugate sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing a compound or conjugate as provided herein and optional pharmaceutical adjuvants in a carrier, such as, for example, water, saline, aqueous dextrose, glycerol, glycols, ethanol, and the like, to thereby form a solution or suspension. If desired, a pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Dosage forms or compositions containing a compound or conjugate provided herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Pharmaceutical compositions suitable for the delivery of a compound or conjugate provided herein and methods for their preparation will be readily apparent to those skilled in the art. Such compositions and methods for their preparation may be found, for example, in *Remington's Pharmaceutical Sciences,* 19th Edition (Mack Publishing Company, 1995).

Methods of Treatment

Conjugates of a biologically active molecule or a derivative thereof and a functionalized polymer as provided herein, and combinations thereof (e.g., two or more conjugates of a biologically active molecule or a derivative thereof) can be used to treat a patient as appropriate for the particular biologically active molecule (e.g., a patient having a disorder selected from the group consisting of an inflammatory disease; diabetes; asthma; hemophilia (e.g., hemophilia A or hemophilia B), a deficiency in a clotting factor (e.g., factor VII deficiency) or other disorder affecting coagulation or clotting; with anemia, e.g., a human patient having anemia resulting from chemotherapy or kidney disease).

In some embodiments, conjugates of TNF inhibitors or a derivative thereof and a functionalized polymer as provided herein, and combinations thereof (e.g., two or more conjugates of a TNF inhibitor or a derivative thereof) can be used to treat a patient having an inflammatory disease, e.g., rheumatoid arthritis, psoriasis such as plaque psoriasis or chronic psoriasis, psoriatic arthritis, juvenile idiopathic arthritis, ankylosing spondylitis, Crohn's disease, or ulcerative colitis. As used herein, treating inflammatory disease refers to reducing the severity of the disease or slowing progression of the disease.

The methods described herein include administering to the patient an effective amount of the conjugate. An effective amount of conjugate(s) or a pharmaceutical formulation containing a conjugate can be any amount that reduces the severity of the disease or slows progression of the disease while not inducing significant toxicity in the patient. Effective amounts of conjugates or a pharmaceutical composition can be determined by a physician, taking into account various factors that can modify the action of drugs such as overall health status, body weight, sex, diet, time and route of administration, other medications, and any other relevant clinical factors.

In some embodiments, conjugates of insulin or a derivative thereof and a functionalized polymer as provided herein, and combinations thereof (e.g., two or more conjugates of insulin or a derivative thereof) can be used to treat a patient having diabetes, e.g., a human patient having type 1 or type 2 diabetes. As used herein, treating diabetes refers to helping to control blood glucose levels. The methods described herein include administering to the patient an effective amount of the conjugate or combinations of conjugates. An effective amount of conjugate(s) or a pharmaceutical formulation containing a conjugate can be any amount that helps reduce or maintain blood glucose levels while not inducing significant toxicity in the patient. Effective amounts of conjugates or a pharmaceutical composition can be determined by a physician, taking into account various factors that can modify the action of drugs such as overall health status, body weight, sex, diet, time and route of administration, other medications, and any other relevant clinical factors.

A conjugate or a pharmaceutical formulation containing a conjugate can be administered by any route, including, without limitation, oral or parenteral routes of administration such as intravenous, intramuscular, intraperitoneal, subcutaneous, intrathecal, intraarterial, nasal, transdermal (e.g., as a patch), or pulmonary absorption. A conjugate described herein can be formulated as, for example, a solution, suspension, or emulsion with one or more pharmaceutically acceptable excipients suitable for the particular route of administration. Subcutaneous administration is particularly useful.

In some embodiments, conjugates of omalizumab or a derivative thereof and a functionalized polymer as provided herein, and combinations thereof (e.g., two or more conjugates of omalizumab or a derivative thereof) can be used to treat a patient having asthma. As used herein, treating asthma refers to reducing the severity of the disease (e.g., reducing the incidence of asthma exacerbations). Treatment with Omalizumab limits the release of mediators of the allergic response and reduces the number of FcεRI receptors on basophils in atopic patients. Treatment with Omalizumab also can increase the expiratory volume in the first second of a forced expiration ($FEV_1$), which is an indicator of the ability to exhale rapidly and completely.

The methods described herein include administering to the patient an effective amount of the conjugate. An effective amount of conjugate(s) or a pharmaceutical formulation containing a conjugate can be any amount that reduces the severity of asthma while not inducing significant toxicity in the patient.

In some embodiments, conjugates of a clotting factor or a derivative thereof and a functionalized polymer as provided herein can be used to treat a patient (e.g., a human patient) diagnosed with hemophilia (e.g., hemophilia A or hemophilia B), a deficiency in a clotting factor (e.g., factor VII deficiency) or other disorder affecting coagulation or clotting. As used herein, treating refers to reducing the severity of the disease or disorder.

Eptacog alfa (activated) (sold by Novo Nordisk) can be used to replace missing factor VII in patients with factor VII deficiency and also can be used in hemophilia patients who have developed inhibitors to factor VIII or IX.

Factor VIII deficiency results in hemophilia A and Factor IX deficiency causes hemophilia B. Moroctocog alfa (glycoprotein (trade name ReFacto®, Xyntha®) are commercially available for Factor VIII replacement therapy. Factor VIII replacement therapy is limited due to development of high-titer inhibitory factor VIII antibodies in some patients. Nonacog alfa (Benefix®) is a human recombinant factor IX product used in treating hemophilia B patients.

Antithrombin is a small glycoprotein that inactivates several enzymes of coagulation system. Its activity enhanced by heparin. Antithrombin alfa (e.g., ATryn®) is commercially available.

In some embodiments, conjugates of a polypeptide that boosts red or white blood cell production or a derivative thereof and a functionalized polymer as provided herein can be used to treat a patient with anemia, e.g., a human patient having anemia resulting from chemotherapy or kidney the group consisting of an inflammatory disease. Conjugates of a polypeptide that boosts white blood cell production or a derivative thereof and a functionalized polymer as provided herein, and combinations thereof (e.g., two or more conjugates of a polypeptide that boosts red or white blood cell production or a derivative thereof) can be used to treat a patient with neutropenia (e.g., neutropenia resulting from chemotherapy or bone marrow transplantation) or to increase the number of hematopoietic stem cells in the blood before collection. As used herein, treating anemia or neutropenia refers to reducing the severity of the disease.

The methods described herein include administering to the patient an effective amount of the conjugate. An effective amount of a conjugate or a pharmaceutical formulation containing a conjugate can be any amount that reduces the severity of the disease or disorder while not inducing significant toxicity in the patient.

Conjugates of an antibody or a derivative thereof and a functionalized polymer as provided herein, and combinations thereof (e.g., two or more conjugates of an antibody or a derivative thereof) can be used to treat a patient, e.g., a human patient. For example, a conjugate that includes Abatacept can be used for the treatment of arthritis (e.g., adult rheumatoid arthritis or JIA). A conjugate that includes Alemtuzumab can be used for treatment of CLL, CTCL, and T-cell lymphoma, or in a conditioning regimen for bone marrow transplantation, kidney transplantation, or islet cell transplantation. A conjugate that includes Basiliximab can be used to prevent rejection in organ transplantation, (e.g., during kidney transplants). A conjugate that includes Belimumab can be used to treat adults with active SLE. A conjugate that includes Besilesomab can be used to detect inflammatory lesions and metastases. A conjugate that includes Bevacizumab can be used to treat various cancers, including colorectal, lung, breast, glioblastoma, kidney, and ovarian cancer. A conjugate that includes Canakinumab can be used to treat autoinflammatory syndromes including familial cold autoinflammatory syndrome, Muckle-Wells syndrome, and neonatal-onset multisystem inflammatory disease. A conjugate that includes Catumaxomab can be used to treat malignant ascites. A conjugate that includes Cetuximab can be used for treatment of metastatic colorectal cancer and head and neck cancer. A conjugate that includes Denosumab can be used for the treatment of osteoporosis, treatment-induced bone loss, bone metastases, rheumatoid arthritis, multiple myeloma, and giant cell tumor of bone. A conjugate that includes Eculizumab can be used to treat paroxysmal nocturnal hemoglobinuria (PNH). A conjugate that includes Ipilimumab can be used to treat melanoma (e.g., metastatic melanoma or unresectable melanoma). A conjugate that includes Natalizumab can be used in the treatment of multiple sclerosis and Crohn's disease. A conjugate that includes Ofatumumab can be used for treating chronic lymphocytic leukemia, follicular non-Hodgkin's lymphoma, diffuse large B cell lymphoma, rheumatoid arthritis, and relapsing remitting multiple sclerosis. A conjugate that includes Panitumumab can be used to treat metastatic colorectal cancer. A conjugate that includes Ranibizumab can be used to treat age-related macular degeneration (e.g., AMD and ARMD). A conjugate that includes Rituximab can be used to treat lymphomas, leukemias, transplant rejection and some autoimmune disorders. A conjugate that includes Tocilizumab can be used to treat rheumatoid arthritis (RA) and systemic juvenile idiopathic arthritis. A conjugate that includes Trastuzumab can be used to treat breast cancer. A conjugate that includes Ustekinumab can be used to treat psoriasis. As used herein, treating a particular disease or disorder refers to reducing the severity of the disease or slowing progression of the disease.

Methods described herein can include monitoring the patient to, for example, determine if the severity or progression of the disease is improving with treatment.

Synthesis

Compounds and conjugates provided herein, including salts thereof, can be prepared using known organic synthesis techniques and can be synthesized according to any of numerous possible synthetic routes. In some embodiments, a compound or conjugate is prepared using a method as provided herein.

The reactions for preparing compounds and conjugates provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry*, 1$^{st}$ Ed., Oxford University Press, 2000; *March's Advanced Organic chemistry: Reactions, Mechanisms, and Structure*, 5$^{th}$ Ed., Wiley-Interscience Publication, 2001; and Peturssion, S. et al., "Protecting Groups in Carbohydrate Chemistry," *J. Chem. Educ.*, 74(11), 1297 (1997) (each of which is incorporated herein by reference in their entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS) or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6) (2004), which is incorporated herein by reference in its entirety) and normal phase silica chromatography.

EXAMPLES

Example 1

Synthesis of isopropyl phosphorodichloridite was performed according to the modified literature procedure of Zwierzak and Koziara, Tetrahedron (1967), 23, 2243-2252.

Dry isopropanol (2 mole) in 100 mL of dry diethyl ether was added dropwise to the vigorously stirred mixture of phosphorus trichloride (4 mole) in 200 mL of diethyl ether at −20° C. The mixture was allowed to warm up to room temperature, and was stirred at this temperature for 4 hours. The mixture was fractionally distilled at normal pressure to obtain the title product by collecting a colorless fraction having bp. 120-125° C.

Example 2

Synthesis of isopropyl, N,N-diisopropylphosphoramidochloridite

Isopropyl phosphorodichloridite (56.5 g, 0.5 mole) in dry diethyl ether (300 mL) was placed in a 1 L round bottom flask and cooled to −30° C. To this vigorously stirred solution, dry diisopropyl amine (109 g, 1 mole) in diethyl ether (200 mL) was added dropwise (2 hr) at the above low temperature. The mixture was then allowed to warm to room temperature and was left at this temperature overnight. The thick white cake of diisopropylammonium hydrochloride was filtered off on a large filter funnel and washed with two portions of ether. The combined ether phase was evaporated and the residue was distilled at lowered pressure collecting a fraction boiling at 83-85° C. (15 Torr).

Example 3

The following is a general procedure used to prepare different phosphoramidite reagents.

An appropriately protected alcohol (1 eq.) was placed in a round bottom flask and dried by coevaporation with toluene. The residue was dissolved in dry dichloromethane (DCM) (5 mL/mmole), and dry triethylamine (TEA) (4 eq.) was added in one portion. To this solution, stirred at room temperature, isopropyl, N,N-diisopropylphosphoramidochloridite (1.5 eq.) in DCM (2 mL/mmole) was added dropwise. The mixture was stirred an additional 30 minutes and when TLC (DCM:Methanol:TEA 95:4:1) showed a complete consumption of the starting alcohol, methanol (5 eq.) was added in one portion and the mixture was stirred further for 30 minutes. The reaction mixture was partitioned between dichloromethane and an aqueous solution of sodium bicarbonate. The organic extracts were combined, evaporated, dried by coevaporation with toluene, and purified by flash column chromatography on silica gel using a gradient of ethyl acetate in hexane with addition of 2% TEA as an eluent. The appropriate fractions were collected, and evaporated. The residual solvents were removed under high vacuum, yielding products in the form of thick oils.

The following starting alcohols were prepared according to the published literature and converted to the respective isopropyl phosphoramidites using the procedure outlined above:

1) An amidite useful for introduction of an amino group was prepared by modification of the method of Gaur, *Nucleosides, Nucleotides & Nucleic Acids* (1991), 10, (4), 895-909:

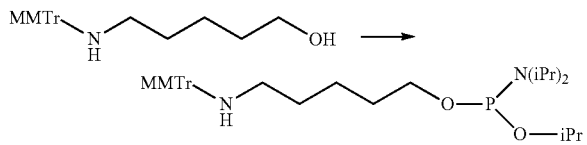

2) An amidite useful for introduction of an aminoxy group was prepared in a process similar to the synthesis of described above for aminating an amidite. The starting aminoxy alcohol was prepared from 6-bromhexanol according to Khomutov, *Zhurnal Obshch Khimyi* 1961, 31, 1992-1995:

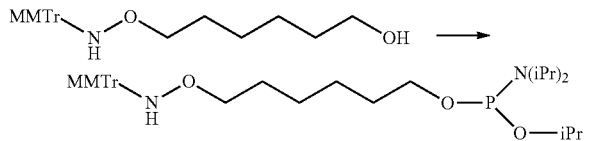

3) An amidite useful for introduction of a hydrazo group was prepared using a modified method of Raddetz et al., *Nucleic Acids Res.* 30, (21), 4793-4802:

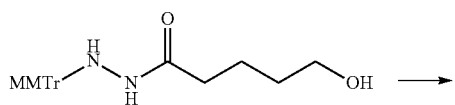

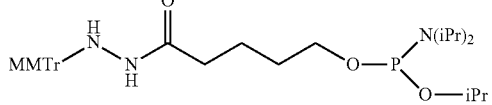

4) An amidite useful for introduction of a thiol was obtained following the procedure described by Connolly and Rider in *Nucleic Acids Res.* 1985, 13, (12), 4485-4502:

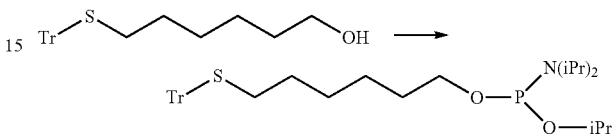

5) An amidite useful for introduction of a carboxyl group was prepared utilizing a chlorotrityl group for protection of a carboxyl group as was described by Kachalova et al. *Helv. Chim. Acta* 2002, 85, 2409-2416:

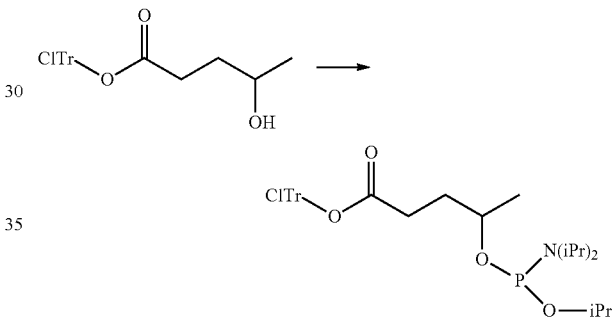

6) An amidite useful for introduction of biotin was prepared following the methodology described by Krempsky et al., *Tet. Lett.*, (1996), 37, (12), 4313-4316:

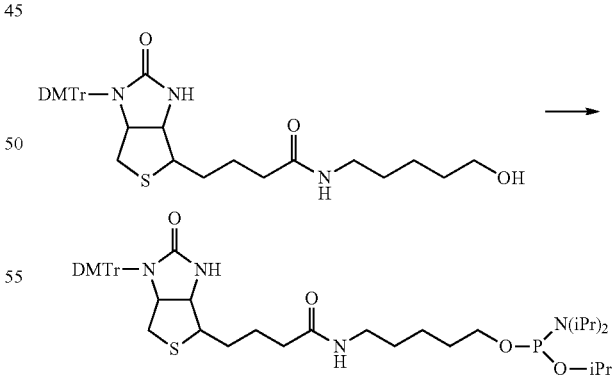

7) The following amidite, prepared in a method analogous to one described by Singh et al. *J. Org. Chem.* 2004, 69, 8544-8546, was used for incorporation of an aliphatic aldehyde group. The aldehyde (as an amide of glyoxalic acid) was obtained after oxidative cleavage of the cis-amine alcohol group:

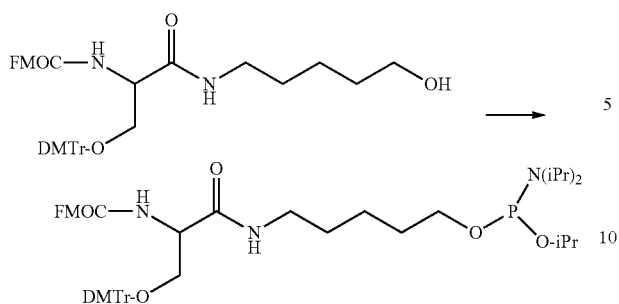

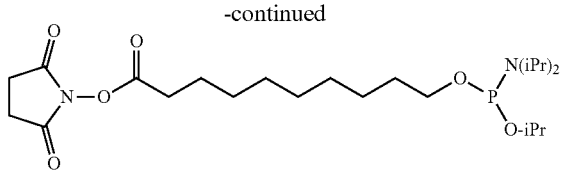

8) The following amidite can be used for incorporation of an aliphatic aldehyde group. This reagent was made in analogy to Spinelli et al. *Nucleosides, Nucleotides and Nucleic Acids* 2007, 26, 883-887. The aldehyde was obtained after acidic hydrolysis of the acetal bond and oxidation of the cis diol system:

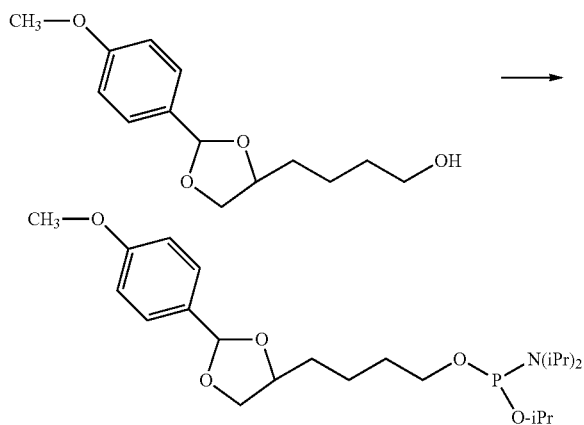

9) The following amidite, prepared by modification of method of Podyminogin et al., *Nucl. Acids Res.* 2001, 29, (24), 5090-5098, can be used for incorporation of an aromatic aldehyde group:

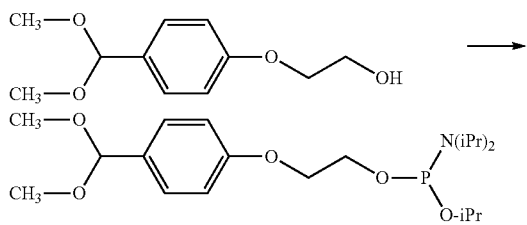

10) An amidite allowing for introduction of an active ester in a single chemical step was prepared analogously to the method described in U.S. Pat. No. 6,320,041:

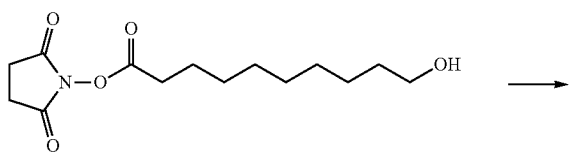

Example 4

The following is a general procedure that was used for the synthesis of pure monosubstituted PEG polymers.

This method utilizes non-derivatized PEG used in excess over the selected phosphoramidite reagent in order to obtain better selectivity. Amidites containing a hydrophobic moiety, like trityl, substituted trityl, long chain fatty esters, or acetals introduce a separation handle that can be used for reversed-phase based chromatographic separation of the product.

Thus PEG 6000 (60 g, 10 mmole, 2 eq.) was dried by double coevaporation with toluene (heating was applied in order to dissolve all material). The residue was dissolved in dry acetonitrile (50 mL) and an appropriate phosphoramidite (5 mmole, 1 eq.) in dry acetonitrile (30 mL) was added in one portion. To this clear solution, stirred at room temperature, a solution of 4,5-dicyanoimidazole (5.9 g, 50 mmol, 10 eq.) in acetonitrile was added in a single portion and the mixture was stirred for 15 minutes. Reaction was stopped by addition of a solution of iodine (0.1 M, 1.2 eq.) in THF:pyridine:water (10:10:1) and the brownish solution was stirred for 3 minutes. Aqueous solution of sodium bisulfite was added in small portions until decolorization of the reaction mixture. After evaporation of most of the volatile matter, the residue was dissolved in dichloromethane and extracted with a saturated aqueous solution of sodium bicarbonate. The evaporated organic phase was dried by coevaporation with toluene, and the residue was crystallized from isopropanol. The isolated crystals were dissolved in a small amount of dichloromethane and precipitated by addition of diethyl ether. The final mixture, being a composition containing a free non-derivatized PEG, mono- and bis-derivatized PEG, was preperatively purified by reverse-phase chromatography. Fractions containing the desired product were evaporated, dried and precipitated from diethyl ether. When removal of the acid labile separation handle was required the polymer is dissolved in isopropanol (with slight heating) and a 5% solution of trichloracetic acid in isopropanol was added. The mixture is cooled down in the freezer to obtain a deprotected crystalline product. If a TLC test (silicagel plates in 10% MeOH:DCM) for the purity of the product still showed the presence of the trityl protecting group, the procedure of acidic deprotection was repeated. Deprotection of other functionalities were performed following the literature procedures as far as was possible, but with some modifications:

1) Trityl protected thiol modified polymer was deprotected with a silver nitrate solution in water. After 30 minutes the solution was treated with dithiotreithiol (2 eq. to the amount of silver ions added) and the pH was raised to 9.0 by addition of potassium carbonate. After 30 minutes, the mixture was filtered through a pad of celite and extracted by dichloromethane. The organic phase was evaporated and thiolated PEG was crystallized from isopropanol.

2) Polymers modified with different aldehyde-introducing phosphoramidites were first treated with acid to remove the trityl or the acetal function. In the case of reagent 7 (Example 3) the FMOC group was removed by treatment of the polymer with 10% piperidine in DCM for 4 hours, followed by quick evaporation of the volatile matter and crystallization of the residue from isopropanol. The final conversion of the cis-amino alcohol or cis-diol to the aldehyde was done by means of 10 mM sodium periodate.

Example 5

Pure, mono-substituted PEG molecules used for further derivatization were prepared as follows.

Certain PEG derivatives can be prepared in a large scale and at reasonably low cost. These derivatives can be regarded by themselves as valuable modifications, but also as a good monovalent starting material, well suited for further derivatization. This Example provides for the preparation of three such derivatives:

1) Mono DMTr-O— Substituted, Linear PEG.

An appropriate PEG (100 g, 2 eq.) was dried by double coevaporation with dry pyridine, dissolved in pyridine (100 mL), and DMTrCl (1 eq.) was added to the stirred mixture at room temperature. The yellow solution was stirred for 24 hours and methanol (10 mL) was added. The reaction mixture was stirred for an additional 60 minutes, evaporated, dissolved in dichloromethane, and treated with an aqueous solution of sodium bicarbonate. The organic phase was evaporated, dried by coevaporation with toluene, and all PEG was isolated after precipitation from diethyl ether. The collected mixture of PEG's was purified by reverse-phase chromatography.

2) Mono MMTr-NH— Substituted, Linear PEG.

A commercial monoamino substituted PEG (1 eq.) or a material prepared according to any of existing procedures, was dried by double coevaporation with dry pyridine. The residue was dissolved in pyridine (10 mL/mmole of PEG) and trimethylchlorosilane (TMSCl) (4 eq.) was added. The mixture was stirred at room temperature for 4 hours and MMTrCl (1.5 eq.) was added. The reaction mixture was stirred overnight, and then methanol (50 eq.) was added and the mixture was stirred for an additional two hours. The total PEG was isolated after evaporation, drying by coevaporation with toluene, crystallization from isopropanol and precipitation from diethylether. The collected mixture of PEG's was purified by reverse-phase chromatography.

3) Mono Tr-S-Substituted, Linear PEG.

An appropriate, non-derivatized PEG was dried by coevaporation with toluene and dissolved in dry DMF (5 mL/mmole). To this stirred solution at room temperature a preformed solution of phosphoroxychloride (0.4 eq.) in dry DMF (5 mL/mmole) was added and stirring was continued for 6 hours. Most of the solvent was then evaporated, and the residue was treated using a saturated aqueous sodium bicarbonate solution. Polyethylene glycol was extracted with dichloromethane and concentrated by evaporation of all volatile matter. The reaction mixture, containing the monochloro-derivatized PEG was dissolved in ethanol (10 mL/mmole). Triphenylmethyl mercaptan (1.3 eq. to the starting PEG) was suspended in ethanol (10 mL/mmole) and converted to the sodium salt by addition of an equivalent amount of sodium hydroxide dissolved in a small amount of water. The salt was combined with the ethanolic solution of PEG and the mixture was stirred overnight. After evaporation of ethanol, the residue was partitioned between dichloromethane and aqueous sodium bicarbonate. The organic phase was evaporated and the residue was crystallized from isopropanol, followed by precipitation of total PEG from diethyl ether. The collected mixture of PEG's was purified by reverse-phase chromatography.

Example 6 a) Conversion of monosubstituted PEG to bis-derivatized PEG was performed using the following method.

A one equivalent of commercial methyl PEG (mPEG), (or any of partially protected PEG's from the Examples 4 or 5), was dried by coevaporation with toluene, and the polymer was dissolved in dry acetonitrile (5 mL/mmole). The modifying phosphoramidite (2-3 eq.) in dry acetonitrile (3 mL/mmole) was added, followed by a suitable activator (10-15 eq.) and the reaction mixture was stirred at RT for 15 minutes. At this point all reactions were analyzed by fast reversed-phase analytical chromatography that showed disappearance of all starting material and formation of more hydrophobic product. Reaction was quenched by addition of an oxidizing iodine solution (1.5 eq. to the amount of the phosphoramidite) or t-butylhydrogenperoxide (4 eq. to the amount of the phosphoramidite) in cases when the synthesized product did not tolerate iodine or water. The iodine-treated reaction mixtures were evaporated, dissolved in dichloromethane, decolorized with bisulfite, and the organic phase was evaporated. The t-butylhydrogenperoxide treated mixtures were evaporated directly. Both mixtures were partially purified by crystallization from isopropanol, followed by precipitation from diethyl ether to obtain a pure, mono-functionalized, bis-substituted PEG.

b) An azeotropically dried PEG was dissolved in dry acetonitrile (5 mL/mmole). The modifying phosphoramidite (1.0 eq.) in dry acetonitrile (3 mL/mmole) was added, followed by a suitable activator (10-15 eq.) and the reaction mixture was stirred at RT for 30 minutes. Reaction was quenched by addition of an oxidizing iodine solution (1.5 eq. to the amount of the phosphoramidite) or t-butyl hydrogenperoxide (4 eq. to the amount of the phosphoramidite) in cases when the synthesized product did not tolerate iodine or water. The iodine-treated reaction mixtures were evaporated, dissolved in dichloromethane, decolorized with bisulfite, and the organic phase was evaporated. The t-butylhydrogenperoxide treated mixtures were evaporated directly. Both mixtures were partially purified by crystallization from isopropanol, followed by precipitation from diethyl ether to obtain reaction mixture free of low molecular components. This mixture was separated on an analytical and on a preparative RP chromatographic system which allow for isolation of pure monosubstituted product. This methodology could be easy applied for amidites introducing amino, hydroxylamino, hydrazo, carboxyl, aldehyde and the biotin group. The isolated products could be deprotected upon treatment with appropriate acidic conditions, followed by precipitation of the deprotected PEG from diethylether, or the non-deprotected material could be used in preparation of hetero-bis-functionalized polymer as presented below.

c) Using the above idea of conversion of PEG diol into a pure, mono-functionalized product from Example 6 b) with subsequent derivatization with another reagent, the following compounds were prepared.

1) MMTr-NH—$(CH_2)_5$—O—PO—(O-iPr)O-PEG-O(O-iPr)-PO—O—$(CH_2)_6$—O—NH-MMTr

2) MMTr-NH—$(CH_2)_5$—O—PO—(O-iPr)O-PEG-O(O-iPr)-PO—O—$CH(CH_3)(CH_2)_2$—COO-ClTr.

The second derivatization were performed as in Example 6a) using excess of the second reagent over PEG to insure quantitative conversion to the double functionalized product The final compound was analyzed by HPLC, but any preparative chromatography at this stage was not needed.

Example 7

The following describes methods used to introduce functional groups which were not stable in the presence of the phosphoramidite group.

Diethylene glycol protected on one end with a DMTr group, and containing a H-phosphonate group at the other end, was synthesized from a tritylated diol by a standard PCl$_3$/triazole method according to Garegg et al., *Chem. Scr.* 1986, 26, 59-62.

The above H-phosphonate (3 eq.) and mPEG (1 eq.) were dried by repeated coevaporation with dry pyridine. The residue was dissolved in pyridine (10 mL/mmole) and treated with pivaloyl chloride (9 eq.). The mixture was stirred at room temperature for 2 hours and the reaction was quenched by addition of triethylammonium bicarbonate (TEAB) (1 M, 5 mL/mmole). The reaction mixture was concentrated and partitioned between dichloromethane and diluted TEAB. The organic phase was evaporated, the residue was dried by repeated coevaporation with toluene, and total PEG was purified by precipitation from diethyl ether. The isolated precipitate was filtered, dissolved in pyridine/carbon tetrachloride 2:1 and 1-amino-6-azido-hexane (4 eq.) was added. The stirred mixture was left overnight at room temperature. The mixture was evaporated, coevaporated with water, and the residual material was treated with an aqueous ammonia solution (25%, 20 mL/mmole) for 4 hours at room temperature in order to cleave the residual non-oxidized H-phosphonate dimer. Ammonia was evaporated and the resulting crude product was purified by means of preparative reverse-phase chromatography. Final removal of the DMTr group and precipitation of the PEG gave the pure azido modified product.

Example 8. Conjugation of Omalizumab

The following describes methods used to conjugate omalizumab with a modified PEG 20K polymer.
Selective DMTr Protection of One End of the PEG Chain.

Commercial PEG 20,000 (20K) (20 g, 1 mmol) was dried by repeated co-evaporation with toluene (3×200 mL) followed by co-evaporation with dichlormethane (200 mL). The residue was dissolved in DCM and dimethylaminopyridine DMAP (0.2 mmol), dry triethylamine (5 mmol) and DMTrCl (1 mmol) were added. The mixture was stirred overnight at room temperature and all volatile matters were evaporated under reduced pressure. The solidified products were dissolved in a minimal volume of acetonitrile (25 mL) and cold (−20 deg C.) isopropanol (200 mL) was gradually poured into this solution with magnetic stirring. The crystallized mixture of PEG derivatives was vacuum filtered, washed with cold isopropanol, and dried overnight at reduced pressure.

A 3 gram portion of this material was dissolved in 10 mL of water/EtOH (4:1) and applied on a manually packed Hamilton PRP-1 Polystyrene column (3×10 cm), washed with ethanol, and equilibrated with 20% EtOH/water containing 0.2% cone ammonia solution.

In order to ensure that all non-derivatized PEG has been eluted out from the column, elution of all products was done using a gradient of ethanol in water: Solvent A: 20% EtOH+0.2% ammonia; solvent B: 100% EtOH+0.2% ammonia. The run was done very slowly and the starting, non-derivatized PEG came out at a solvent mixture of 22-25% of B, while the broad peak of mono tritylated product came within a solvent mixture of 46-55% of B. It should be noted that only the first part of this broad peak: at a solvent mixture of 46-50% of B was used in further synthetic steps. It implies, most probably, that reverse phase (RP) separation of tritylated PEG fractionates the PEG molecules according to their molecular wight, with larger molecules coming first. All runs were performed at the flow of 2 mL/min.

The collected fractions were examined for the presence of PEG using a colorimetric test using a barium chloride and KI/iodine solution. This test together with the chromatogram showing the absorbance of the DMTr group indicated that the isolated product was the mono-DMTr protected PEG. This material was free of bis-tritylated product and free of non-derivatized PEG. The purity of the isolated material was confirmed by a separate HPLC analysis on a C-18 RP column. The product was concentrated to dryness, dissolved in a minimal amount of acetonitrile (1 mL), precipitated from diethyl ether (50 mL) and dried under vacuum.
Synthesis of the Hetero Bi-Functional Active Ester Form of PEG

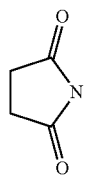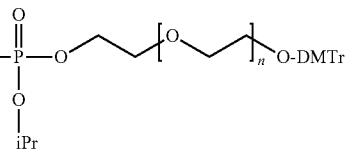

Mono-DMTr protected PEG (1.0 g, 0.05 mmol) was dried by double coevaporation with dry acetonitrile (2×30 mL) and previously synthesized amidite (See Example 3) that introduces NHS-ester function (0.25 mmol, 125 mg) was added followed by addition of tetrazol solution (0.1 M) in dry acetonitrile (13 mL, 1.3 mmol, 5 eq per amidite).

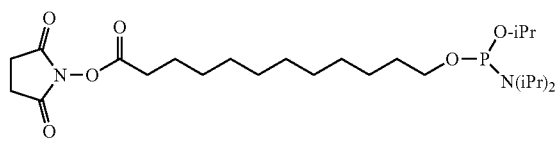

The mixture was stirred at RT for 30 min and an oxidizing agent t-butyl hydrogen peroxide solution in dry toluene (1M, 2 mL, 8 eq) was added in a single portion. Stirring was continued for an additional 30 minutes and the volatile components were evaporated at reduced pressure. The residue was dissolved in 2 mL of acetonitrile and the non-solubilized tetrazole was spun down. The clear upper solution was transferred to a larger 50 mL Falcon tube and cold isopropanol (−20° C.) was gradually added causing crystallization of the PEG molecule. This material was spun down, washed again with cold isopropanol, and dried under vacuum (oil pump). The product was obtained in the form of white fluffy crystals.

Conjugation of Omalizumab to PEG Reagent.

Conjugation of PEG to IgG omalizumab was performed following the methodology described in J. Decruex, R. Vanbever and, P. R. Crocker, *Bioconjugate Chem.* (2008) 19: 2088-2094.

Briefly, omalizumab (300 mg; SEQ ID NO:1) was dissolved in water (5 ml) and portionized into separate Sörsted tubes containing 15 mg of IgG each. One of the tubes was diluted with (PBS) phosphate buffer (0.2 M, pH 7.3) to 1 mL and placed on a NAP 10 desalting column previously equilibrated with the same buffer. The desalted protein was isolated with 1.5 mL of the buffer. To a portion of the desalted IgG (0.5 ml, 5 mg, 0.033 micromol), PEG reagent (20 mg, ca 5 micromol, 30 eq) was added and the mixture was left for 180 min with occasional shaking. After this time a solution of glycine (0.1 M) in phosphate buffer (0.2 mL) was added to quench any non-reacted PEG reagent.

The conjugate was analyzed by the following methods:

1) SDS electrophoresis 7.5% acrylamide gel for 90 min and 180 V. Proteins were stained with Coomassie blue (see FIG. 2).

Figure 3:
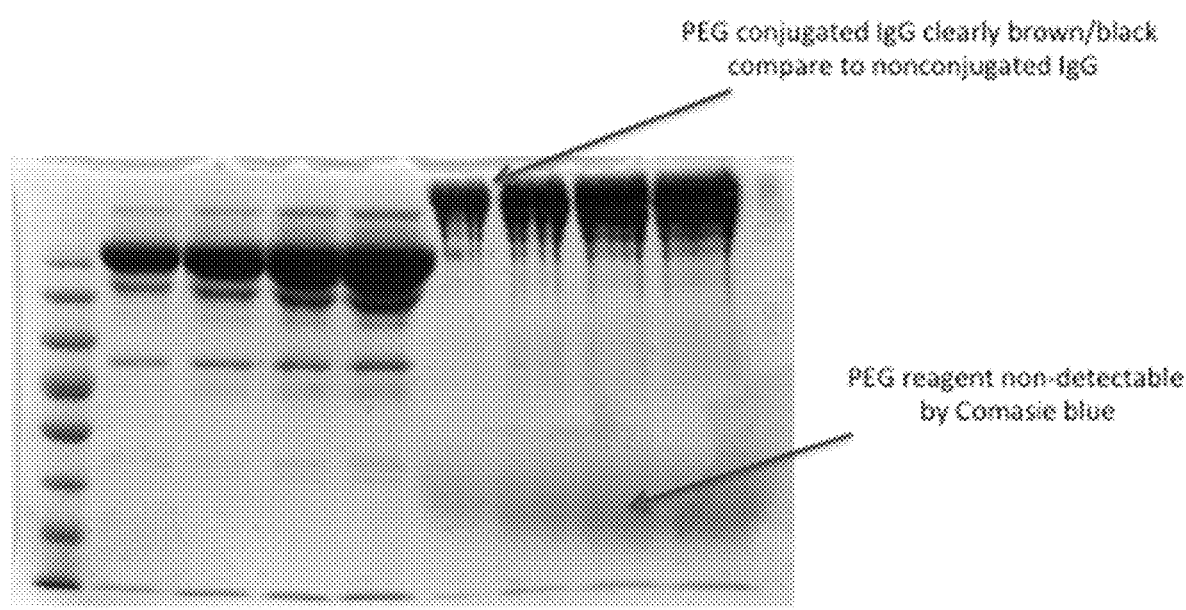
FIG. 3 provides a photograph of a SDS electrophoresis gel of the product of the conjugation of omalizumab to a PEG reagent as provided herein stained with barium chloride and iodine.

2) The above gel was additionally stained by using a solution of barium chloride and iodine which is known to selectively label PEG containing molecules in a brown to black color dependent on the amount of PEG (this is the main method for detection of non-derivatized PEG). During this step the previously Coomassie stained proteins did not change their color (see FIG. 3).

Figure 4:
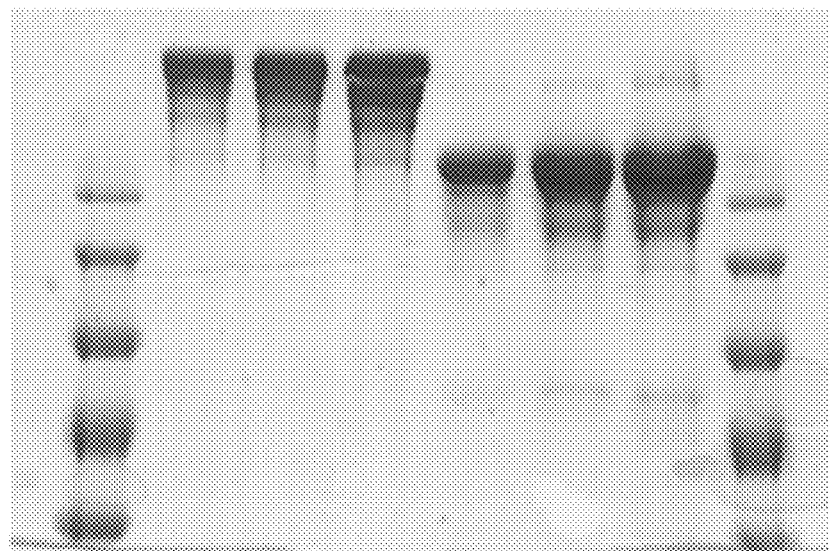
FIG. 4 provides a photograph of a SDS electrophoresis gel of the product of the conjugation of omalizumab to a PEG reagent as provided herein stained with Coomassie blue.

3) SDS gel electrophoresis was also run using lower amounts of both reference IgG and conjugation reaction, and was performed for a longer time (180 min) and higher voltage (220 V) in order to achieve better conjugate separation. The gel was stained using Coomassie blue. FIG. 4 shows the conjugate on the left side and free IgG on the right.

4) Using the methodology described above, two additional conjugation reactions were also performed. Both reactions were made starting from 5 mg of omalizumab in PBS buffer. For 10 equivalents excess of PEG reagent, a portion of 7.5 mg of PEG NHS was added, and for a 5 equivalents reaction, 3.75 mg PEG was added. Both reactions were quenched after 3 hours and analyzed together alongside the previous 30 equivalents reaction by SDS gel electrophoresis using 8% acrylamide. This time runs times were 180 min to achieve better separation.

Figure 5:
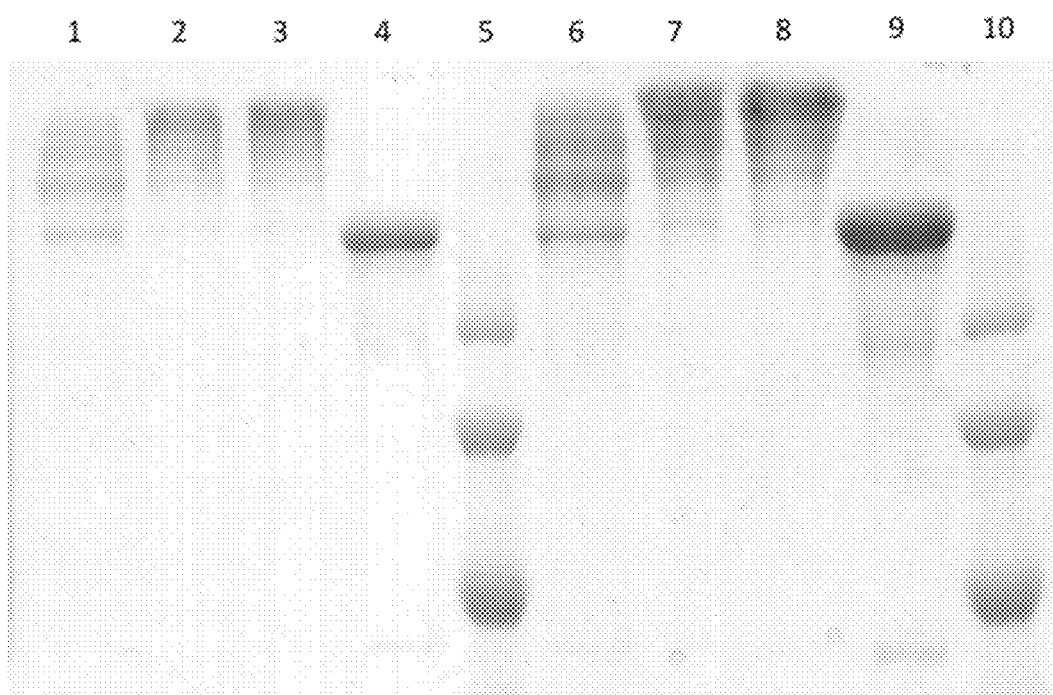
FIG. 5 provides a photograph of a SDS electrophoresis gel of the product of the conjugation of omalizumab to a PEG reagent as provided herein stained with Coomassie blue.
Figure 6:
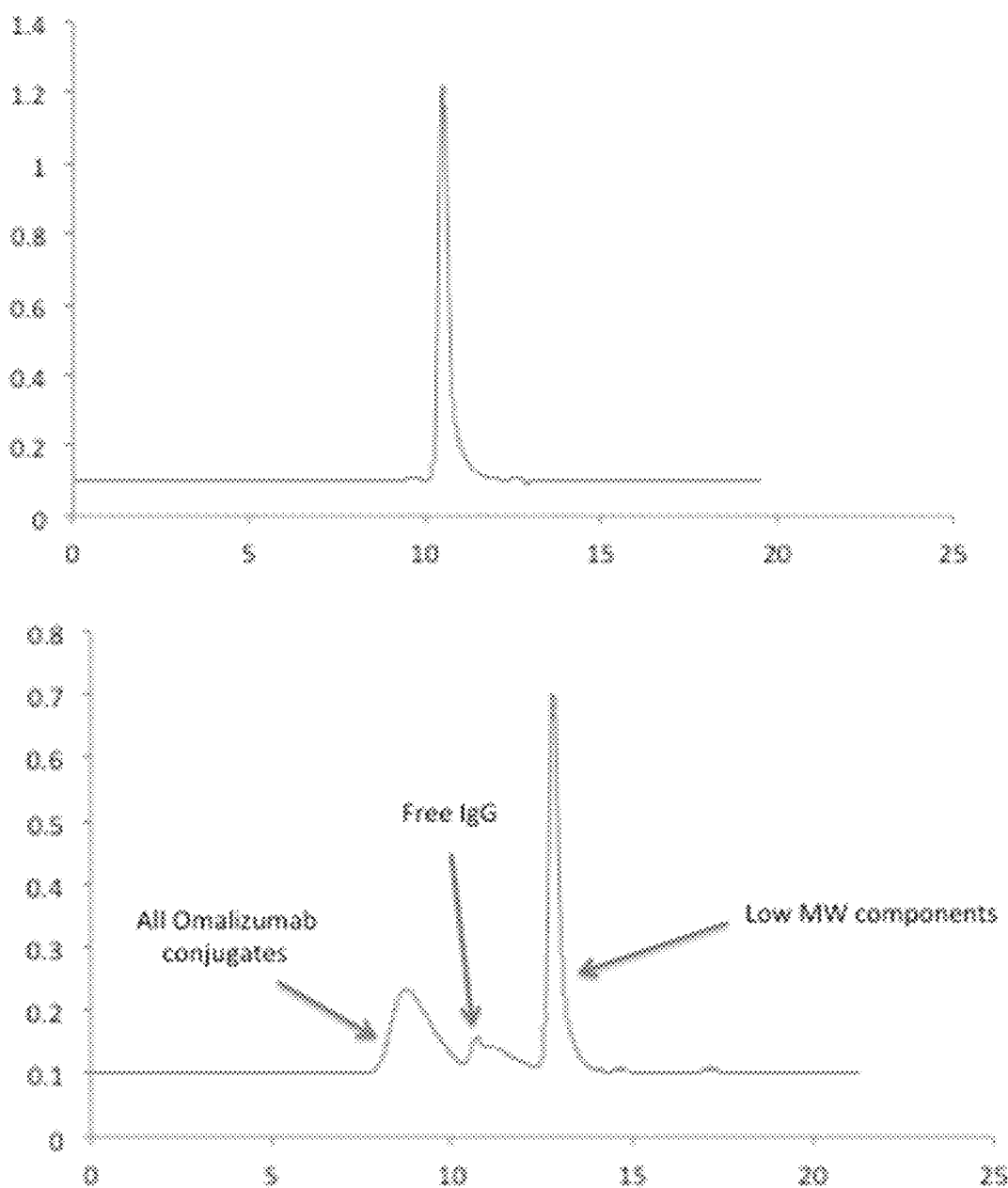
FIG. 6 shows HPLC Gel Filtration analysis of free omalizumab and reaction mixture obtained after pegylation of omalizumab.

FIG. 5 shows the results of the reactions as follows:

Lane 1—2 µg of IgG conjugate obtained by using 5 eq of PEG reagent
Lane 2—2 µg of IgG conjugate obtained by using 10 eq of PEG reagent
Lane 3—2 µg of IgG conjugate obtained by using 30 eq of PEG reagent
Lane 4—2 µg of IgG starting material
Lane 5—protein mass standards
Lane 6—5 µg of IgG conjugate obtained by using 5 eq of PEG reagent
Lane 7—5 µg of IgG conjugate obtained by using 10 eq of PEG reagent
Lane 8—5 µg of IgG conjugate obtained by using 30 eq of PEG reagent
Lane 9—5 µg of IgG starting material
Lane 10—protein mass standards 5) Analysis of the reaction mixture was also performed using gel permeation chromatography. This analysis was performed using a Zorbax GF-450 HPLC column and phosphate buffer (0.2 M, pH 7.0) as eluent using a 1.0 mL/min flow. FIG. 6 shows that the pool of omalizumab conjugates was well separated from the starting non-conjugated omalizumab.

Example 9. Pegylation of Lysozyme and Insulin 5 mg of each protein (0.35 µmol of lysozyme (Mw=14,300) and 0.86 µmol of insulin (Mw=5,808; SEQ ID NO.2)) were dissolved in phosphate buffer (0.2 M, pH 7.4) and PEGylating (in form of previously described NHS reagent—see Example 8) 20 kD was added in 5-fold excess. The reaction was kept overnight and was quenched by addition of excess glycine. A sample of both starting protein and pegylated reaction mixtures were tested on a Zorbax GF 450 gel filtration HPLC column, with 280 nm detection, to determine the degree of derivatization.

Figure 8:
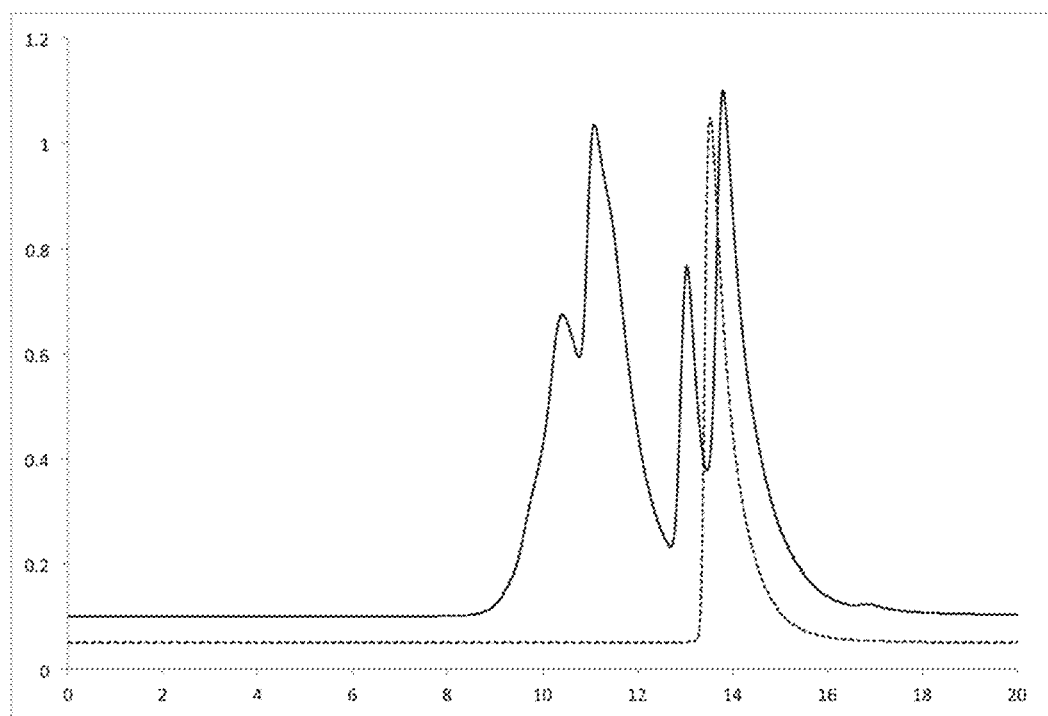
FIG. 8 illustrates the HPLC Gel Filtration chromatogram of lysozyme (dashed line) and the lysozyme pegylation reaction product (solid line).

As shown in FIG. 8, the normalized chromatogram shows lysozyme (dashed line) and lysozyme pegylation reaction (solid line). The double peak (at approximately 10-12 min) represents multiply pegylated lysozyme, the peak at 13 min is the residual PEG reagent, and the last peak represents unreacted protein.

Figure 9:
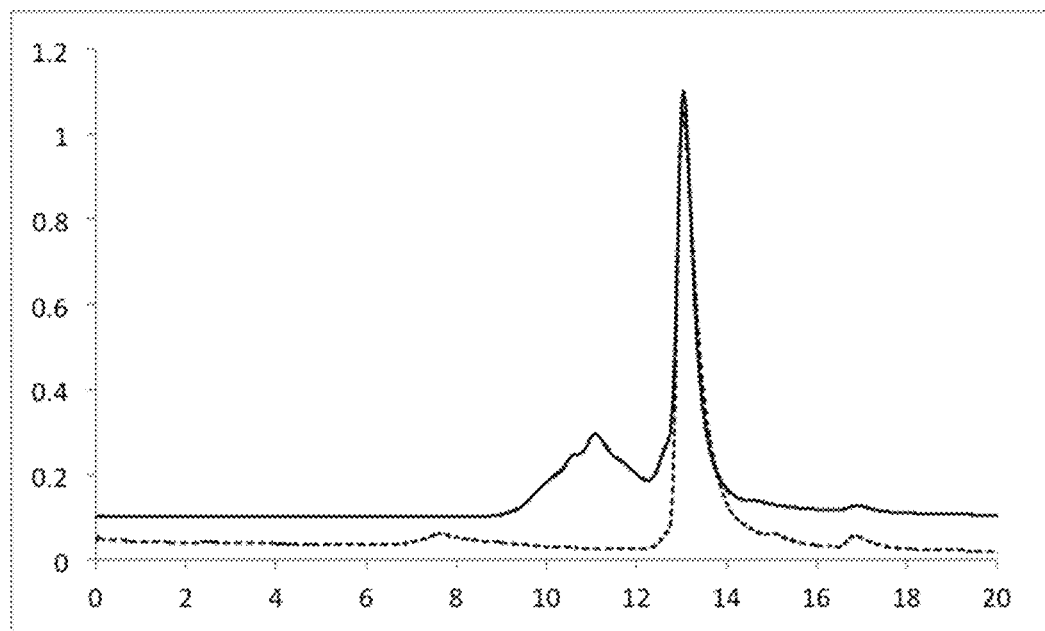
FIG. 9 illustrates the HPLC Gel Filtration chromatogram of insulin (dashed line) and insulin pegylation reaction mixture (solid line).

As shown in FIG. 9, the chromatogram shows insulin (dashed line) and insulin pegylation reaction mixture (solid line). For an unknown reason, insulin (despite its formally lower Mw) has a shorter retention time than lysosome, and it co-elutes with the residual PEG reagent. The fastest running multiple peak (10-12 min) represents pegylated insulin.

Example 10. Pegylation of Etanercept (ENBREL®)

Etanercept (SEQ ID NO:3) was pegylated in the same manner as described in Example 8. Both omalizumab and etancercept have very similar Mw, but etanercept is not a monoclonal Ab, but is instead a soluble receptor. The different shapes of these two proteins is probably the reason why in gel filtration HPLC analysis free etanercept is running closer to its pegylated conjugate than in the case of omalizumab.

Figure 11:
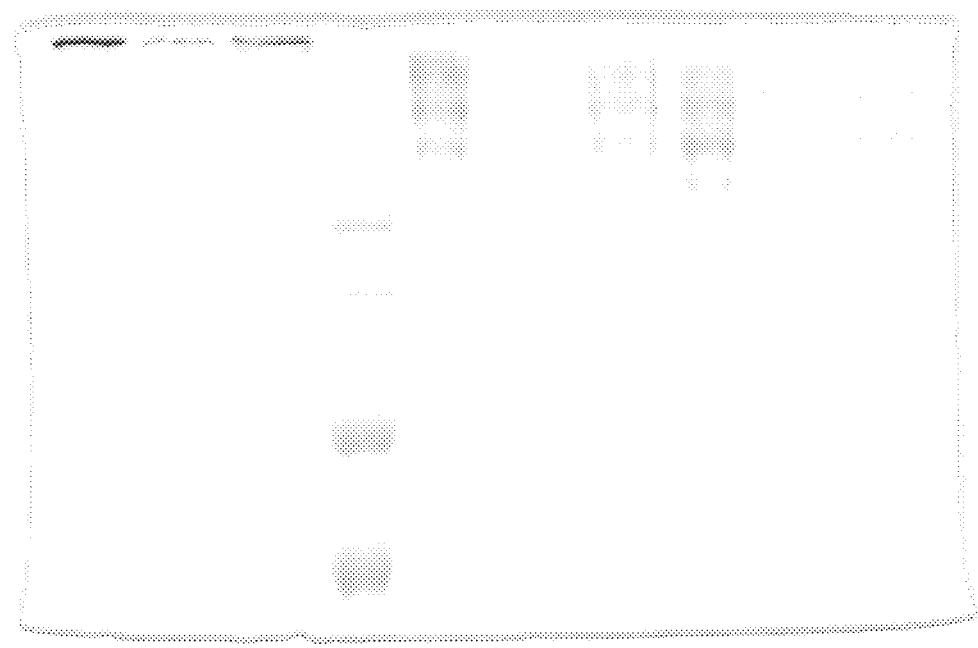
FIG. 11 provides a photograph of a SDS electrophoresis gel of the product of the conjugation of entanercept to a PEG reagent as provided herein stained with Coomassie blue.

SDS electrophoresis 7.5% acrylamide gel run for 90 min and at 180 V. Proteins were stained with Coomassie blue. FIG. 11 shows the results of the reactions as follows:

1) Lane 8 shows pegylation of etancercept using 5 eq of PEG reagent—the residual amount of free etancercept also appears in this lane.

2) Lane 5 shows pegylation using 10 eq of PEG reagent—free etancercept is not visible any longer—at least three different bands of pegylated etancercept are shown.

3) Lane 1 shows pegylation with 30 eq of PEG reagent. All etancercept is pegylated.

4) Lane 4 is a commercial protein ladder.

Figure 12:
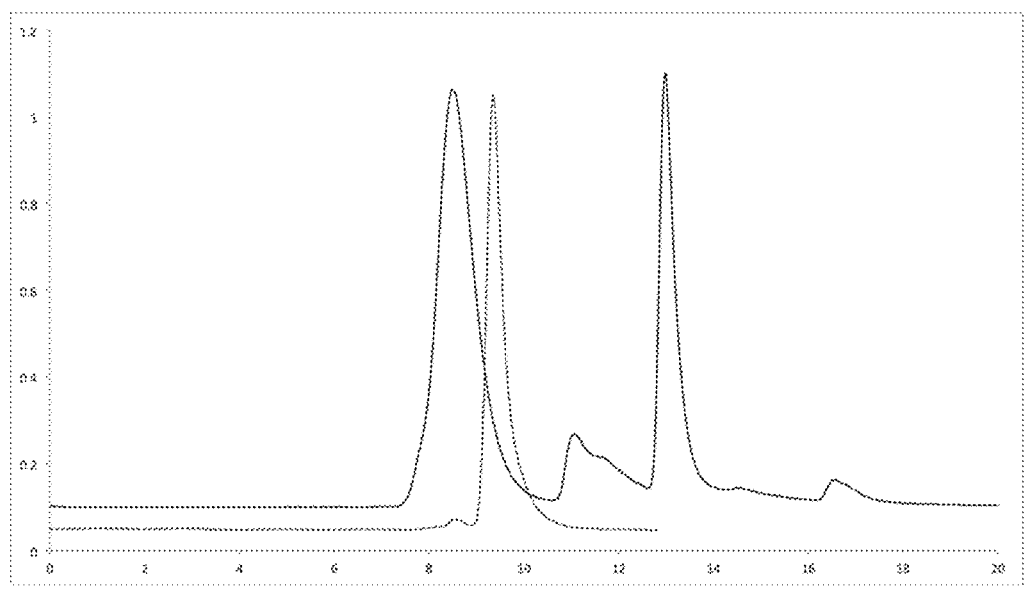
FIG. 12 illustrates the HPLC Gel Filtration chromatogram of etanercept (dashed line) and the etanercept pegylation reaction product (solid line).

FIG. 12 shows the normalized chromatogram showing free etanercept (dashed line), and pegylated etanercept after reaction with 10 equivalents of the pegylating reagent (solid line). During the preparative HPLC run, half minute long fractions were collected starting from 7.5 min, and ending at 10.0 minutes. The content of proteins was measured photometrically at 280 nm. To avoid all possible contamination of free etanercept in the conjugate fraction, a fraction from 8.0 min to 8.5 min was chosen for the further studies.

Example 11. Evaluation of Pegylated Etanercept (ENBREL®) by ELISA

Material and Methods

ENBREL® (etanercept; Wyeth Europa Ltd, Berkshire, UK) was conjugated to a 20 KDa PEG (PEG20) as described in Example 8. The 20 KDa PEG was conjugated at 5 times (5 eq) or 10 times (10 eq) molar excess compared to etanercept.

Recombinant human TNF-alpha (rhTNF-alpha; AbCam PLC, Cambridge, UK; at a fixed concentration of 2.9 ng/ml) was mixed with different concentrations (29000 ng/ml-56.6 pg/ml) of non-PEGylated etanercept, PEG20-etanercept (5 eq) or PEG20-etanercept (10 eq). The pre-incubation mixtures were incubated in a refrigerator at 4-8° C. overnight. The amount of unbound rhTNF-alpha was analysed with a sensitive enzyme-linked immunosorbent assay (ELISA). In brief, 96-well plates (MaxiSorb, Nunc, Roskilde, Denmark) were used for the ELISA. Plates were coated with two anti-TNF-alpha monoclonal antibodies (TNF3/4, Mabtech AB, Nacka Strand, Sweden) diluted in PBS, pH 7.4, to a final concentration of 2 μg/ml. The 96-well plates were incubated in a refrigerator at 4-8° C. overnight. The 96-well plates were thereafter repeatedly washed with PBS/0.05% Tween 20. rhTNF-alpha standard (dilution series 1:1) and the pre-incubation mixture containing rhTNF-alpha/PEG20-etanercept (5 or 10 eq) or rhTNF-alpha/etanercept (non-PEGylated) diluted in PBS/0.1% BSA were thereafter added to the plates and incubated for 2 hours at room temperature. The plates were repeatedly washed with PBS/0.05% Tween 20 and thereafter incubated 1 hour at room temperature with 1 μg/ml of a biotin-conjugated anti-TNF-alpha antibody (TNF5, Mabtech AB, Nacka Strand, Sweden) diluted in PBS/0.1% BSA/0.05% Tween 20. Finally, streptavidine-HRP (Mabtech AB, Nacka Strand, Sweden) diluted 1:1000 in PBS/0.1% BSA/0.05% Tween 20 was added to the plates and incubated 1 hour following a repeated wash step with PBS/0.05% Tween. A developer (3,3',5,5' tetramethylbenzidine, TMB; Sigma-Aldrich, St Louis, Mich., USA) was added after a final repeated wash with PBS/0.05% Tween 20. A blue color reaction developed and the reaction was terminated by the addition of 1 M $H_2SO_4$ 15-20 minutes. The optical density of the resultant yellow color was measured in a spectrophotometer at 450 nm.

The resulting ODs were plotted in GraphPad Prism 6.0 and fitted to a 4-parameter logistic curve fitting algorithm.

Results

Figure 13:
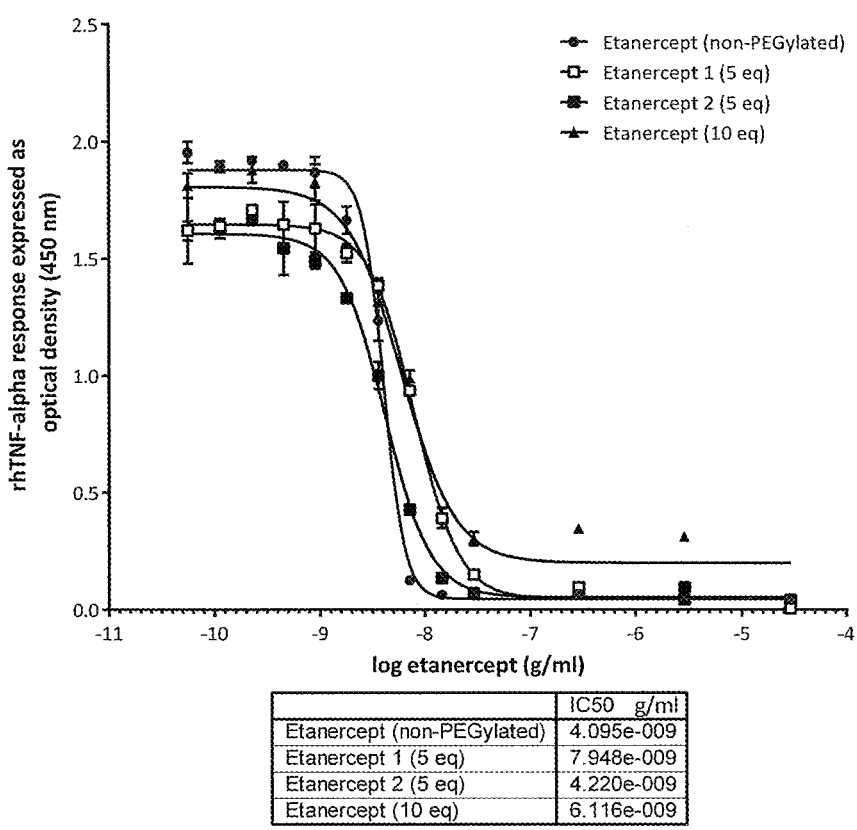
FIG. 13 shows rhTNF-alpha concentrations following over-night incubation at 4-8° C. with various concentrations of etanercept (non-PEGylated), PEG20-etanercept (5 eq), or PEG20-etanercept (10 eq). A fixed concentration of 2.9 ng/ml rhTNF-alpha was used in all incubations. PEGylation was conducted in 5 time molar excess (5 eq) or 10 time molar excess (10 eq) of PEG20 compared etanercept. $IC_{50}$ is expressed as gram etanercept per ml.
Figure 14:
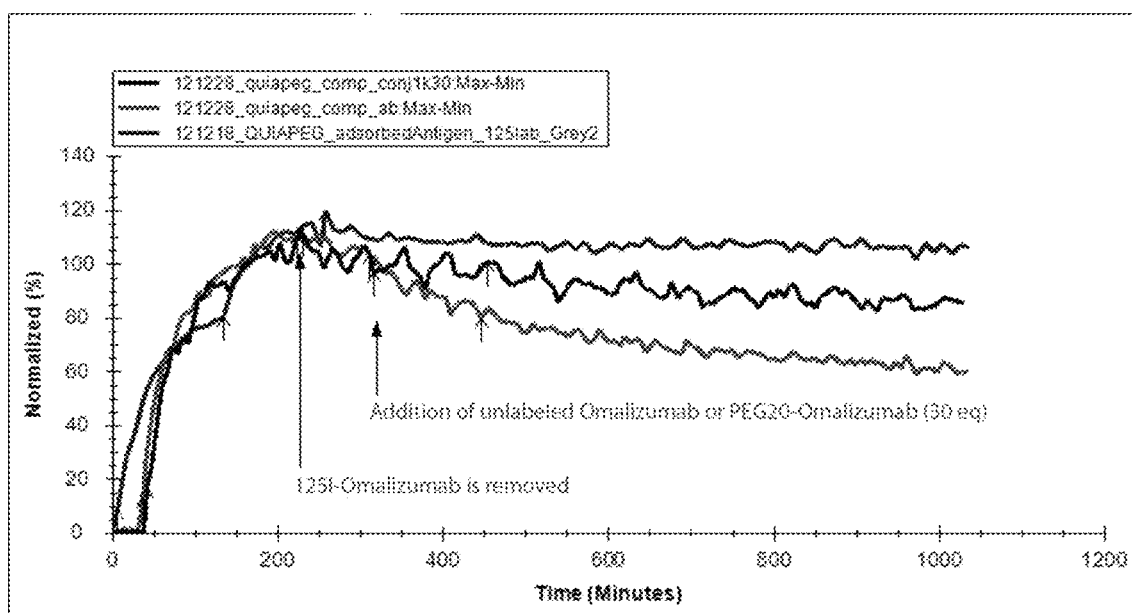
FIG. 14 illustrates the dissociation over time of $^{125}$I-omalizumab bound to human IgE with or without unlabeled omalizumab or PEGylated omalizumab.

The covalent attachment of PEG20 did not disturb etanercepts binding capacity of rhTNF-alpha. $IC_{50}$ values of etanercept (with or without PEG20) dilution curves were calculated and are shown in FIG. 13. The results demonstrate that the $IC_{50}$ values of PEG20-etanercept (5 or 10 eq) are less than 2-fold higher compared to non-PEGylated etanercept (FIG. 13).

The $IC_{50}$ concentrations of non-PEGylated and PEGylated etanercept clearly indicate that a 20 KDa PEG does not significantly impair the binding and neutralization of TNF-α by etanercept. In addition, the use of 5 or 10 equivalents of 20 KDa PEG during the conjugation process to etanercept does not deteriorate the inhibition of TNF-α.

Example 12. Biosensor Evaluation of the Binding of Pegylated Omalizumab to Human IgE The method was based on LigandTracer technology developed by RidgeView Instruments AB, Uppsala, Sweden (www.ridgeview.eu).

The experiment was performed on rotated petri dishes. 2 μg of human IgE (AbCam, Cambridge, UK) was adsorbed on the plastic surface and allowed to dry over-night. 100 μg omalizumab (Genentech, Calif., USA) was labeled with $^{125}I$ (13.1 MBq/100 μg) according to the chloramine T method. $^{125}I$-labeled omalizumab (10 nM) was then added to the IgE on the rotating petri dish. After approximately 3½ hour the labeled antibody was exchanged with a buffer (see FIG. 14). Unlabeled omalizumab or PEG20-omalizumab (approx. 200 nM; see Example 8) was added to evaluate the ability to compete and displace $^{125}I$-labeled omalizumab bound to IgE. The upper curve (blue) shows the binding of $^{125}I$-labeled omalizumab to IgE without competition (FIG. 14). The lower curve (red) shows how $^{125}I$-labeled omalizumab bound to IgE is displaced and competed out by unlabeled omalizumab. The curve in between (black) demonstrates that PEG20-omalizumab (30 eq) has the ability to displace and partially compete out $^{125}I$-labeled omalizumab bound to IgE.

Example 13. Synthesis of a Reagent for Introduction of an Aminoxy Group, Containing a Linker Unit Similar to the Polyethylene Glycol Chain 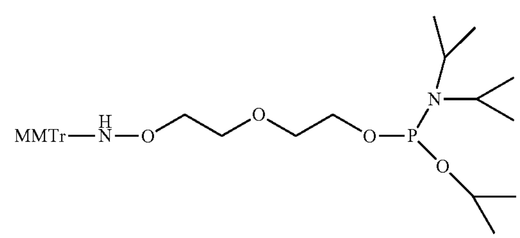 Monotosylate of diethylene glycol. To an ice chilled solution of diethyleneglycol (19 mL, 200 mmol) in anhydrous pyridine (8.1 mL, 100 mmol) and dichlormethane (50 ml), was added in a single portion of a solution of p-toluenesulfonyl chloride (7.6 g, 40 mmol) in dichlormethane (30 mL). The mixture was stirred at room temperature overnight and partitioned between a saturated solution of sodium bicarbonate and dichloromethane (2×200 mL). The combined organic phases were evaporated and coevaporated with toluene (2×100 mL) to remove pyridine and traces of water. The remaining yellow oil was purified using flash silica gel chromatography, yielding the title product in the form of colorless oil in a 67% yield.

N-2-(2-Hydroxyethoxy)ethoxyphtalimide. To a stirred solution of N-hydroxyphtalimide (4.3 g, 26.2 mmol) in dry DMF (mL) was added DBU (4.0 g, 26.2 mmol). To this dark red solution was added monotosylate of diethylene glycol (6.8 g, 26.2 mmol). The reaction mixture was heated at 80° C. overnight, concentrated in vacuo, dissolved in ethyl acetate (200 mL) and extracted with saturated sodium bicarbonate until the aqueous phase was colorless. The organic phase was evaporated and dried by coevaporation with toluene. The title product was obtained after purification by flash silica gel chromatography as white solid. Yield 74%.

Hydrazinolysis of N-2-(2-Hydroxyethoxy)ethoxyphtalimide. To a stirred solution of N-2-(2-Hydroxyethoxy)ethoxyphtalimide (4.85 g, 19.3 mmol) in ethanol was added hydrazine hydrate (25 mmol) and the mixture was stirred at room temperature for 1 hr. The white solid formed during this reaction was filtered and the filtrate was evaporated to dryness and coevaporated with toluene (3×50 mL) yielding an oil, which was used further without purification.

Tritylation of alkoxy amine. The oily compound obtained above was dissolved in dry pyridine (100 mL) and to this stirred solution trimethylchlorosilane (4.9 mL, 38.6 mmol) was added in one portion. The mixture was stirred for 30 min and monomethoxy trityl chloride (MMTrCl) (8.9 g, 29 mmol) was added. This mixture was stirred at room temperature overnight and was desilylated by addition of methanol (50 mL). The clear mixture was stirred for 2 hr., concentrated at reduced pressure and the residue was partitioned between saturated sodium bicarbonate and chloroform. The combined chloroform extracts (2×200 mL) were evaporated, coevaporated with toluene (2×100 mL), and the residual oil was purified by flush silica gel chromatography, yielding the product in form of oil. Yield 77%.

Synthesis of the title phosphoramidite. The N-MMTr protected aminoxy alcohol (5.55 g, 14.8 mmol) was dried by coevaporation with toluene (2×50 mL), dissolved in dry dichloromethane (100 mL) and dry triethylamine (6.0 mL, 59.2 mmol) was added followed by isopropyl, N,N-diisopropylphosphoramidochloridite (22.2 mmol). The rest of this reaction was made in accordance with the general description of phosphitylation process as in Example 3. The final product was obtained in 81% yield in the form of a slightly yellow oil.

Example 14

This example provides a process for preparing a reagent which introduces an aliphatic aldehyde group to a previously monofunctionalized polyethylene glycol (e.g., a DMTr containing polymer). The fully derivatized PEG is deprotected in a single step upon treatment with diluted hydrochloric acid.

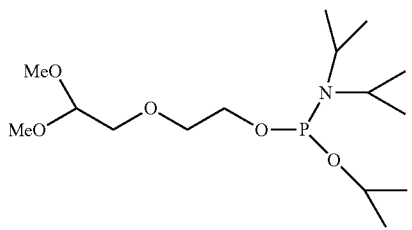 [SMILES: COC(COCCOP(OC(C)C)N(C(C)C)C(C)C)OC]

2-(2,2-Dimethoxy-ethoxy)-ethanol. This compound was obtained from ethylene glycol and 2-chloro-1,1-dimethoxyethane following procedure described by Lei Tao et al. *J. Am. Chem. Soc.* 2004, 126, 13220-13221. The final product was taken to the following reaction without purification.

The hydroxyl acetal was converted to the title product following the methodology from Example 3, yielding, upon silica gel purification the product in a 61% yield as colorless oil.

1) An essentially pure, modified polymer, comprising a water soluble, non peptidic and non nucleotidic, linear or branched polymer backbone, containing from 2 and up to 100 termini, and having at least one terminus being covalently bonded to the structure:

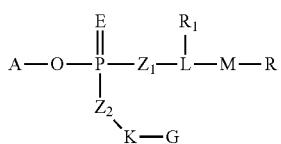

wherein:
A is the point of bonding to the terminus of the polymer backbone;
E is oxygen or sulfur;
K is selected from the group consisting of linear alkyl, branched alkyl, alkyloxyalkyl, or oligomeric form of alkyloxyalkyl;
G is none, or is selected from the group consisting of an alkoxy, trityloxy or substituted trityloxy group;
$Z_1$ and $Z_2$ are O or NH in such a way that both $Z_1$ and $Z_2$ may be O, but when $Z_1$ is NH then $Z_2$ is O, and when $Z_2$ is NH then $Z_1$ is O.
L is selected from the group consisting of linear alkyl, branched alkyl, nucleoside, alkyloxyalkyl, oligomeric form of alkyloxyalkyl, aryl and substituted aryl;
M is a group reactive with a biologically active molecule or detectable functional group;
R is selected from a group consisting of protecting groups, hydrophobic separation handles, activating groups, hydrogen or none, $R_1$ is a hydrophobic separation handle or none, and both R and $R_1$ can coexist providing that there is only one hydrophobic separation handle within the molecule or the hydrophobicity of either of these groups is substantially higher than the other;

2) The modified polymer of claim 1, wherein the functional group M is selected from the group consisting of hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide, biotin or a fluorophore.

3) The modified polymer of claim 1, wherein the group K is selected from the group consisting of methyl, ethyl, propyl, isopropyl, butyl, isobutyl, sec-butyl, tert-butyl, hexyl, or a residue from diethylene glycol, triethylene glycol, tetraethylene glycol or hexaethylene glycol.

4) The modified polymer of claim 1, wherein the group L is $C_1$-$C_{12}$ alkyl or substituted alkyl.

5) The modified polymer of claim 1, wherein the group R is selected from trityl, monoalkoxytrityl, dialkoxytrityl, pixyl, alkoxypixyl, FMOC, trifluoroacetyl, acetal, cyclic acetal or combinations thereof.

6) The modified polymer of claim 1, wherein, for the functional group M being carboxyl, the group R is selected from the group consisting of chlorotrityl, trityl, N-hydroxysuccinimidyl, p-nitrophenyl, pentachlorophenyl, simple non-activating alkyls selected from the group of $C_1$-$C_{18}$ alkyls or none.

7) The modified polymer of claim 1, wherein the non peptidic and non nucleotidic polymer backbone is selected from the group consisting of poly(alkylene glycol), poly(oxyethylated polyol), poly(olefinic alcohol), poly(α-hydroxy acid), poly(vinyl alcohol), polyoxazoline, and copolymers and mixtures thereof.

8) The modified polymer of claim 1, wherein the non peptidic and non nucleotidic polymer backbone is poly(ethylene glycol).

9) The modified polymer of claim 8, wherein the poly(ethylene glycol) has an average molecular weight from about 500 Da to about 100000 Da.

10) An essentially pure, linear form of modified polymer of claim 1, wherein the two termini of the polymer are modified non-symmetrically with two different functional groups and wherein the two functional groups are linked to the polymer as in the structure:

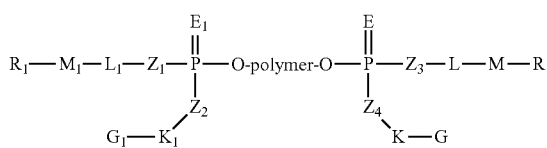

wherein:
M and $M_1$ are two different functional groups reactive with a biologically active molecule or detectable functional groups;
E and $E_1$ are independently oxygen or sulfur;
The pair $Z_1$ and $Z_2$ are independent from the pair $Z_3$ and $Z_4$ and both $Z_1$ and $Z_2$ may be O, but when $Z_1$ is NH then $Z_2$ is O, and when $Z_2$ is NH then $Z_1$ is O, similarly for a pair of $Z_3$ and $Z_4$—both $Z_3$ and $Z_4$ may be O, but when $Z_3$ is NH then $Z_4$ is O, and when $Z_4$ is NH then $Z_3$ is O;
L and $L_1$ are independently selected from the group consisting of linear alkyl, branched alkyl, alkyloxyalkyl, oligomeric form of alkyloxyalkyl, aryl and substituted aryl;
R and $R_1$ are independently protecting groups, activating groups or none;
K and $K_1$ are independently selected from the group consisting of linear alkyl, branched alkyl, alkyloxyalkyl, or oligomeric form of alkyloxyalkyl;
G and $G_1$ are independently selected from the group consisting of none, an alkoxy, trityloxy or substituted trityloxy group;
L-M-R and $L_1$-$M_1$-$R_1$ fragments are linked to the respective terminus of the said polymer via phosphotriester, thiophosphotriester or amidophosphotriester bonds;

11) The modified polymer of claim 10, wherein the two different functional groups M and $M_1$ are selected independently from the group consisting of hydroxyl, amine, thiol, carboxyl, aldehyde, glyoxal,dione, alkenyl, alkynyl, alkedienyl, azide, acrylamide, vinyl sulfone, hydrazide, aminoxy, maleimide, dithiopyridine, iodoacetamide, biotin or a fluorophore.
12) The modified polymer of claim 10, wherein the group K is selected from the group consisting of methyl, ethyl, propyl, isopropyl, butyl, isobutyl, sec-butyl, tert-butyl, hexyl, or a residue from diethylene glycol, triethylene glycol, tetraethylene glycol or hexaethylene glycol.
13) The modified polymer of claim 10, wherein the group L is $C_1$-$C_{12}$ alkyl or substituted alkyl.
14) The modified polymer of claim 10, wherein the group R is selected from trityl, monoalkoxytrityl, dialkoxytrityl, pixyl, alkoxypixyl, FMOC, trifluoroacetyl, acetal, cyclic acetal or combinations of thereof.
15) The modified polymer of claim 10, wherein, for the functional group M being carboxyl, the group R is selected from the group consisting of chlorotrityl, trityl, N-hydroxysuccinimidyl, p-nitrophenyl, pentachlorophenyl, simple non-activating alkyls selected from the group of $C_1$-$C_{18}$ alkyls or none.
16) The modified polymer of claim 10, wherein the polymer is poly(ethylene glycol).
17) The modified polymer of claim 16, wherein the poly(ethylene glycol) has an average molecular weight from about 500 Da to about 100000 Da.
18) An essentially pure, linear form of modified polymer of claim 1, wherein the two termini of the polymer are modified non-symmetrically with two different functional groups and wherein the two functional groups are linked to the polymer as in the structure:

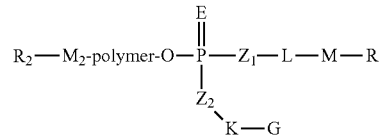

wherein:
M and $M_2$ are two different functional groups reactive with a biologically active molecules or M is a detectable functional group;
E is O or S;
K is selected from the group consisting of linear alkyl, branched alkyl, alkyloxyalkyl, or oligomeric form of alkyloxyalkyl;
G is none or is selected from the group consisting of an alkoxy, trityloxy, monoalkoxy substituted trityloxy group or dialkoxy substituted trityloxy group;
$Z_1$ and $Z_2$ are O or NH in such way that both $Z_1$ and $Z_2$ may be O, but when $Z_1$ is NH then $Z_2$ is O, and when $Z_2$ is NH then $Z_1$ is O;
L is selected from the group consisting of linear alkyl, branched alkyl, alkyloxyalkyl, oligomeric form of alkyloxyalkyl, aryl and substituted aryl;
R is a protecting group, activating group, hydrogen or none;
L-M-R fragment is linked to the first terminus of the said polymer via phosphotriester, thiophosphtriester or amidophosphotriester;
$M_2$ is O, S or NH;
$M_2$ is linked directly to the second terminus of the polymer, and not via phosphotriester, thiophosphtriester or amidophosphotriester;
$R_2$ is a protecting group or none.

19) The modified polymer of claim 18, wherein the functional group M is selected from the group consisting of hydroxyl, amine, thiol, carboxyl, aldehyde, glyoxal,dione, alkenyl, alkynyl, alkedienyl, azide, acrylamide, vinyl sulfone, hydrazide, aminoxy, maleimide, dithiopyridine, iodoacetamide or biotin.
20) The modified polymer of claim 18, wherein the group $R_2$ is selected from the group consisting of trityl, monoalkoxytrityl, dialkoxytrityl, pixyl, alkoxypixyl, FMOC, alkylcarboxyl, benzoyl, tetrahydropyranyl, methyl or none.
21) The modified polymer of claim 18, wherein the polymer is poly(ethylene glycol).
22) The conjugate of any polymer of claims 1 to 18 with a biologically active molecule wherein said biologically active molecule is selected from the group consisting of enzymes, peptides, polypeptides, nucleotides, oligonucleotides, polynucleotides and low molecular weight drugs.
23) A method of synthesizing a substantially pure, water soluble polymer of claim 1, said method comprising the steps of:
a) contacting the water soluble polymer, of non-peptidic and non-nucleotidic type, and having linear or branched polymer backbone, and containing from 2 and up to 100 termini, in a water free solvent, with a selected modifying reagent in form of the phosphoramidite derivative as in the structure:

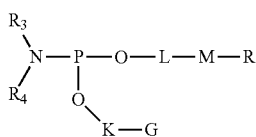

wherein:

$R_3$ and $R_4$ are isopropyls or are a part of of morpholine ring.

b) starting reaction by addition of an activating reagent.
c) oxidation of $P^{+3}$ to $P^{+5}$ by addition of an oxidizing reagent.
d) optional chromatographic purification of the protected polymer.
e) removal of the protecting groups.

24) Method of claim 23 wherein the activating reagent is selected from tetrazole, 2-ethylthiotetrazole, 2-bezylthio-tetrazole, 4,5-dicyanoimidazole, "Activator 42", pyridinium hydrochloride or pyridinium trifluoroacetate 25) Method of claim 23 wherein the oxidizing reagent is selected from a group consisting of iodine, water peroxide, t-butyl hydrogen peroxide, acetone peroxide, sulfur and thiuram disulfide.

26) Method of claim 23, wherein the ratio between the polymer and the phosphoramidite is from 1:1 to 10:1 in order to facilitate formation of monosubstituted product.

27) A method of synthesizing a substantially pure, water soluble polymer of claim 10, said method comprising the steps of:
a) reacting the water soluble polymer, of non-peptidic and non-nucleotidic type, having linear polymer backbone, and containing two reactive termini, in a water free solvent, with a selected first modifying reagent in form of the phosphoramidite derivative, under conditions that facilitate formation of monoderivatized product.
b) chromatographic isolation of the monoderivatized polymer.
c) reacting the monoderivatized product with a second modifying reagent in the form of phosphoramidite derivative, under conditions that facilitate the quantitative conversion to the double modified polymer.
d) isolation of the double modified polymer by precipitation or crystallization.

28) A method of synthesizing a substantially pure, water soluble polymer of claim 18, said method comprising the steps of:
a) reacting the substantially pure, linear polymer, substituted at the first terminus with a function $R_2$-$M_2$, with a selected modifying reagent in form of the phosphoramidite derivative under conditions facilitating the quantitative conversion of the mono substituted polymer to the double modified polymer.
b) isolation of the double modified polymer by precipitation or crystallization.

29) The use of any material of claim 1 to claim 28 for formation of a conjugate between this material and a biologically active molecule, wherein said biologically active molecule is selected from the group consisting of enzymes, peptides, polypeptides, nucleotides, oligonucleotides, polynucleotides and low molecular weight drugs.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A conjugate, or a pharmaceutically acceptable salt thereof, comprising a water-soluble, non-peptidic, and non-nucleotidic polymer backbone having at least one terminus covalently bonded to a structure of formula (9):

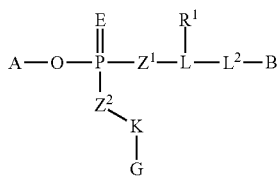

or a salt thereof,
wherein:
A is the point of covalent bonding to the terminus of the polymer backbone, wherein the polymer backbone is poly(ethylene glycol), wherein said poly(ethylene glycol) has an average molecular weight from about 500 Da to about 100,000 Da;
E is O;
K is selected from the group consisting of: alkylene, alkyleneoxyalkylene, and oligomeric alkyleneoxyalkylene;
G is selected from the group consisting of: hydrogen, alkoxy, and a hydrophobic separation handle;
$Z^1$ and $Z^2$ are O;
L is selected from the group consisting of: a divalent radical of a nucleoside, alkylene, alkyleneoxyalkylene, oligomeric alkyleneoxyalkylene, and unsubstituted and substituted arylene;
$R^1$ is absent or a hydrophobic separation handle, wherein only one of $R^1$ and G can be a hydrophobic separation handle;
$L^2$ is a covalent linking moiety between L on the polymer backbone and B; and
B is a clotting factor or a derivative of a clotting factor.

2. The conjugate of claim 1, wherein only one termini of the polymer backbone is covalently bonded to the structure of formula (9).

3. The conjugate of claim 1, wherein the polymer backbone has two termini.

4. The conjugate of claim 3, wherein only one termini of the polymer backbone is covalently bonded to the structure of formula (9).

5. The conjugate of claim 3, wherein both termini of the polymer backbone are covalently bonded to a structure of formula (9).

6. The conjugate of claim 1, wherein K is selected from the group consisting of: methylene, ethylene, propylene, isopropylene, butylene, isobutylene, sec-butylene, tert-butylene, and hexylene, or a residue from diethylene glycol, triethylene glycol, tetraethylene glycol or hexaethylene glycol.

7. The method of claim 6, wherein G is hydrogen.

8. The conjugate of claim 1, wherein G is a substituted or unsubstituted trityloxy.

9. The conjugate of claim 1, wherein L is a substituted or unsubstituted $C_1$-$C_{12}$ alkylene.

10. A conjugate, or a pharmaceutically acceptable salt thereof, comprising a structure of formula (10):

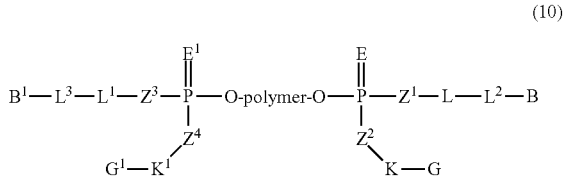

or a salt form thereof,
wherein:
polymer is poly(ethylene glycol), wherein said poly(ethylene glycol) has an average molecular weight from about 500 Da to about 100,000 Da, wherein each linking group is bonded at a different terminus of said polymer;
E and $E^1$ are independently O;
K and $K_1$ are independently selected from the group consisting of: alkylene, alkyleneoxyalkylene, and oligomeric alkyleneoxyalkylene;
G and $G_1$ are independently absent or are selected from the group consisting of: alkoxy and a hydrophobic separation handle;
each pair of $Z^1$ and $Z^2$ and $Z^3$ and $Z^4$ are O,
L and $L^1$ are independently selected from the group consisting of: a divalent radical of a nucleoside, alkylene, alkyleneoxyalkylene, oligomeric alkyleneoxyalkylene, and unsubstituted and substituted arylene;
$L^2$ is a covalent linking moiety between L on the polymer backbone and B;
$L^3$ is a covalent linking moiety between -$L^1$- on the polymer backbone and $B^1$; and
B and $B^1$ are independently a clotting factor or a derivative of a clotting factor.

11. A conjugate, or a pharmaceutically acceptable salt thereof, comprising a compound of formula (11):

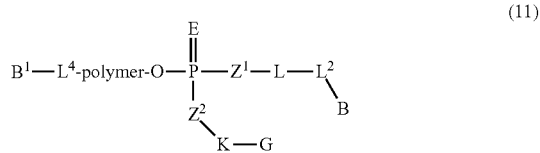

or a salt form thereof,
wherein:
polymer is poly(ethylene glycol) wherein said poly(ethylene glycol) has an average molecular weight from about 500 Da to about 100,000 Da, wherein $L^4$ and the phosphonate-derived functional group are bonded at a different terminus of said polymer;

E is O;

K is selected from the group consisting of: alkylene, alkyleneoxyalkylene, and oligomeric alkyleneoxyalkylene;

G is selected from the group consisting of: hydrogen, alkoxy, and a hydrophobic separation handle;

$Z^1$ and $Z^2$ are independently O;

L is selected from the group consisting of: a divalent radical of nucleoside, alkylene, alkyleneoxyalkylene, oligomeric alkyleneoxyalkylene, and unsubstituted and substituted arylene;

$L^2$ is a covalent linking moiety between L on the polymer backbone and B;

$L^4$ is a covalent linking moiety between the polymer backbone and $B^1$; and

B and $B^1$ are independently a clotting factor or a derivative of a clotting factor.

12. A composition comprising the conjugate of claim 1, and a pharmaceutically acceptable excipient.

13. The composition of claim 12, wherein B is a clotting factor.

14. A composition comprising the conjugate of claim 10, and a pharmaceutically acceptable excipient.

15. The composition of claim 14, wherein B is a clotting factor.

16. The composition of claim 14, wherein $B^1$ is a clotting factor.

17. A composition comprising the conjugate of claim 11, and a pharmaceutically acceptable excipient.

18. The composition of claim 17, wherein B is a clotting factor.

19. The composition of claim 17, wherein $B^1$ is a clotting factor.

20. A method of treating a patient diagnosed with hemophilia, said method comprising administering to said patient an effective amount of the conjugate of claim 1.

21. The method of claim 20, wherein B is a clotting factor.

22. A method of treating a patient diagnosed with hemophilia, said method comprising administering to said patient an effective amount of the conjugate of claim 10.

23. A method of treating a patient diagnosed with hemophilia, said method comprising administering to said patient an effective amount of the conjugate of claim 11.

* * * * *

UNITED STATES PATENT AND TRADEMARK OFFICE
CERTIFICATE OF CORRECTION

PATENT NO. : 10,806,796 B2
APPLICATION NO. : 16/544823
DATED : October 20, 2020
INVENTOR(S) : Marek Kwiatkowski Page 1 of 1

It is certified that error appears in the above-identified patent and that said Letters Patent is hereby corrected as shown below:

Column 114, Line 48, In Claim 10, delete "-L1-" and insert -- L1 --, therefor.

Signed and Sealed this
Twenty-second Day of December, 2020

Andrei Iancu
*Director of the United States Patent and Trademark Office*